US012601009B2

(12) United States Patent　　　(10) Patent No.: US 12,601,009 B2
Joung et al.　　　　　　　　　　　(45) Date of Patent: *Apr. 14, 2026

(54) HIGHLY SENSITIVE IN VITRO ASSAYS TO DEFINE SUBSTRATE PREFERENCES AND SITES OF NUCLEIC-ACID BINDING, MODIFYING, AND CLEAVING AGENTS

(71) Applicant: The General Hospital Corporation, Boston, MA (US)

(72) Inventors: J. Keith Joung, Winchester, MA (US); Vikram Pattanayak, Wellesley, MA (US); Karl Petri, Cambridge, MA (US); Jason Michael Gehrke, Cambridge, MA (US); Kanae Esther Sasaki, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/502,817

(22) Filed: Nov. 6, 2023

(65) Prior Publication Data

US 2024/0309446 A1　　Sep. 19, 2024

Related U.S. Application Data

(63) Continuation of application No. 16/852,257, filed on Apr. 17, 2020, now Pat. No. 11,845,987, which is a continuation of application No. 16/386,472, filed on Apr. 17, 2019, now Pat. No. 11,898,203.

(60) Provisional application No. 62/767,633, filed on Nov. 15, 2018, provisional application No. 62/659,073, filed on Apr. 17, 2018.

(51) Int. Cl.
　　*C12Q 1/6874*　　　(2018.01)
　　*C12N 15/10*　　　(2006.01)

(52) U.S. Cl.
　　CPC ....... *C12Q 1/6874* (2013.01); *C12N 15/1058* (2013.01); *C12Y 305/04005* (2013.01)

(58) Field of Classification Search
None
See application file for complete search history.

(56) References Cited

U.S. PATENT DOCUMENTS

| | | | |
|---|---|---|---|
| 7,803,550 | B2 | 9/2010 | Makarov et al. |
| 8,071,312 | B2 | 12/2011 | Makarov et al. |
| 8,399,199 | B2 | 3/2013 | Makarov et al. |
| 8,420,319 | B2 | 4/2013 | Mikawa |
| 8,697,359 | B1 | 4/2014 | Zhang |
| 8,728,737 | B2 | 5/2014 | Makarov et al. |
| 9,163,284 | B2 | 10/2015 | Iliu et al. |
| 9,322,006 | B2 | 4/2016 | Liu et al. |
| 9,512,446 | B1 | 12/2016 | Joung et al. |
| 9,822,407 | B2 | 11/2017 | Joung et al. |
| 9,850,484 | B2 | 12/2017 | Joung et al. |
| 9,988,674 | B2 | 6/2018 | Joung et al. |
| 10,221,436 | B2 * | 3/2019 | Hardenbol .............. C40B 20/04 |
| 10,233,490 | B2 | 3/2019 | Stapleton et al. |
| 10,501,794 | B2 | 12/2019 | Joung et al. |
| 2005/0202490 | A1 | 9/2005 | Makarov et al. |
| 2005/0221341 | A1 | 10/2005 | Shimkets et al. |
| 2006/0040297 | A1 | 2/2006 | Leamon et al. |
| 2006/0292611 | A1 | 12/2006 | Berka et al. |
| 2007/0197458 | A1 | 8/2007 | Dutreix et al. |
| 2009/0082295 | A1 | 3/2009 | Jungneli et al. |
| 2010/0076057 | A1 | 3/2010 | Sontheimer et al. |
| 2010/0317722 | A1 | 12/2010 | Lavon |
| 2011/0060493 | A1 | 3/2011 | Miura et al. |
| 2011/0189776 | A1 | 8/2011 | Terns et al. |
| 2011/0207221 | A1 | 8/2011 | Cost et al. |
| 2011/0223638 | A1 | 9/2011 | Wiedenheft et al. |
| 2011/0281736 | A1 | 11/2011 | Drmanac et al. |
| 2011/0287545 | A1 | 11/2011 | Cost |
| 2012/0157322 | A1 | 6/2012 | Myllykangas et al. |
| 2012/0208705 | A1 | 8/2012 | Steemers et al. |
| 2013/0130248 | A1 | 5/2013 | Haurwitz et al. |
| 2013/0137605 | A1 | 5/2013 | Shendure et al. |
| 2013/0143204 | A1 | 6/2013 | Von Kalle |
| 2013/0203605 | A1 | 8/2013 | Shendure et al. |
| 2013/0303461 | A1 | 11/2013 | Iafrate et al. |
| 2013/0309668 | A1 | 11/2013 | Makarov et al. |
| 2014/0024542 | A1 | 1/2014 | Richards |
| 2014/0170753 | A1 | 6/2014 | Zhang |
| 2014/0179006 | A1 | 6/2014 | Zhang |

(Continued)

FOREIGN PATENT DOCUMENTS

| | | |
|---|---|---|
| CN | 102373288 | 3/2012 |
| EP | 3530737 | 8/2019 |

(Continued)

OTHER PUBLICATIONS

Office Action in Chinese Appln. No. 201980040610.5, mailed on Nov. 7, 2024, 9 pages (with English translation).
Akhtar et al., "Using TRIP for genome-wide position effect analysis in cultured cells," Nat. Protoc., May 2014, 9(6):1255-1281.
Al-Attar et al, "Clustered Regularly Interspaced Short Palindromic Repeats (CRISPRs): The Hallmark of an Ingenious Antiviral Defense Mechanism in Prokaryotes," Biol Chem. 2011, 392(4):277-289.
Anders et al, "Structural basis of PAM-dependent target DNA recognition by the Cas9 endonuclease," Nature, Jul. 2014, 513:569-573.

(Continued)

*Primary Examiner* — Heather Calamita
*Assistant Examiner* — Jessica D Parisi
(74) *Attorney, Agent, or Firm* — Fish & Richardson P.C.

(57) ABSTRACT

Described herein are, among other things, in vitro methods of identifying double stranded DNA sequences that are cleaved by a nuclease. For example, by providing a library of defined linear dsDNA oligonucleotides of known sequences, incubating the library in the presence of a nuclease, ligating DNA adapters, amplifying cleaved oligonucleotides, and determining the sequence(s) of the amplified fragments.

6 Claims, 25 Drawing Sheets

Specification includes a Sequence Listing.

(56) References Cited

U.S. PATENT DOCUMENTS

| | | | |
|---|---|---|---|
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234289 A1 | 8/2014 | Liu et al. |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0357530 A1 | 12/2014 | Zhang et al. |
| 2014/0377868 A1 | 12/2014 | Joung et al. |
| 2015/0024500 A1 | 1/2015 | Yu et al. |
| 2015/0031134 A1 | 1/2015 | Zhang et al. |
| 2015/0044191 A1 | 2/2015 | Liu et al. |
| 2015/0045546 A1 | 2/2015 | Siksnys et al. |
| 2015/0050699 A1 | 2/2015 | Siksnys et al. |
| 2016/0304950 A1 | 10/2016 | Joung et al. |
| 2017/0073747 A1 | 3/2017 | Joung et al. |
| 2017/0088833 A1 | 3/2017 | Joung et al. |
| 2017/0198344 A1 | 7/2017 | Vaisvila et al. |
| 2017/0253909 A1 | 9/2017 | Uemori et al. |
| 2018/0073012 A1 | 3/2018 | Liu et al. |
| 2018/0087104 A1 | 3/2018 | Joung et al. |
| 2018/0245071 A1 | 8/2018 | Joung et al. |
| 2018/0265920 A1 | 9/2018 | Joung et al. |
| 2019/0106687 A1 | 4/2019 | Joung et al. |
| 2019/0177710 A1 | 6/2019 | Lee |
| 2020/0010889 A1 | 1/2020 | Joung et al. |
| 2020/0131536 A1 | 4/2020 | Kim |
| 2020/0199665 A1 | 6/2020 | Joung et al. |
| 2020/0239930 A1 | 7/2020 | Joung et al. |
| 2021/0071248 A1 | 3/2021 | Joung et al. |
| 2021/0155984 A1 | 5/2021 | Joung et al. |

FOREIGN PATENT DOCUMENTS

| | | | |
|---|---|---|---|
| JP | 2009-502202 | 1/2009 |
| JP | 2013/518602 | 5/2013 |
| JP | 2013-544498 | 12/2013 |
| JP | 2014-506788 | 3/2014 |
| JP | 2015-521468 | 7/2015 |
| JP | 2018-530536 | 10/2018 |
| WO | WO 2008/108989 | 9/2008 |
| WO | WO 2010/054108 | 5/2010 |
| WO | WO 2011/086118 | 7/2011 |
| WO | WO 2011/100058 | 8/2011 |
| WO | WO 2012/065143 | 5/2012 |
| WO | WO 2012/164565 | 12/2012 |
| WO | WO 2013/078470 | 5/2013 |
| WO | WO 2013/098244 | 7/2013 |
| WO | WO 2013/176772 | 11/2013 |
| WO | WO 2013/191775 | 12/2013 |
| WO | WO 2014/008447 | 1/2014 |
| WO | WO 2014/018080 | 1/2014 |
| WO | WO 2014/071070 | 5/2014 |
| WO | WO 2014/071361 | 5/2014 |
| WO | WO 2014/093701 | 6/2014 |
| WO | WO 2015/074017 | 5/2015 |
| WO | WO 2015/117040 | 8/2015 |
| WO | WO 2015/200378 | 12/2015 |
| WO | WO 2016/081798 | 5/2016 |
| WO | WO 2016/141224 | 9/2016 |
| WO | WO-2016205613 A1 * | 12/2016 | ............... C12N 1/20 |
| WO | WO 2017/040348 | 3/2017 |
| WO | WO 2017/059313 | 4/2017 |
| WO | WO 2017/079593 | 5/2017 |
| WO | WO 2017/218979 | 12/2017 |
| WO | WO 2018/052247 | 3/2018 |
| WO | WO 2018/218166 | 11/2018 |
| WO | WO 2018/218188 | 11/2018 |
| WO | WO 2019/075197 | 4/2019 |

OTHER PUBLICATIONS

AU Office Action in Australian Application No. 2015280069, dated Nov. 6, 2020, 6 pages.

Aynaud et al., "Human Tribbles 3 protects nuclear DNA from cytidine deamination by APOBEC3A." Journal of Biological Chemistry, Nov. 2012, 287(46):39182-39192.

Barrangou & May, "Unraveling the potential of CRISPR-Cas9 for gene therapy," Expert Opin. Biol. Ther., 2014, 15:311-314.

Bélanger et al., "Deamination intensity profiling of human APOBEC3 protein activity along the near full-length genomes of HIV-1 and MoML V by HyperHRM analysis," Virology, Jan. 2014, 448:168-175.

Berg et al., "Section 7.1. Homologs Are Descended from a Common Ancestor," in Biochemistry, W.H. Freeman, pub. 2002, [retrieved on Jan. 30, 2017]. Retrieved from the Internet: URL <https://www.ncbi.nlm.nih.gov/books/NBK22355/>. 1 page.

Bikard et al, "Programmable repression and activation of bacterial gene expression using an engineered CRISPR-Cas system," Nucleic Acids Res., Aug. 2013, 41(15):7429-7437.

BioInformatics.StackExchange.com [online], "Revision History for Bioinformatics Stack Exchange Post 'What are Orthogonal DNA Sequences?'," Oct. 22, 2019, retrieved on Nov. 6, 2023, retrieved from URL<https://bioinformatics.stackexchange.com/posts/10623/revisions>, 3 pages.

BioInformatics.StackExchange.com [online], "Timeline for Bioinformatics Stack Exchange Post 'What are Orthogonal DNA Sequences?'," created Oct. 22, 2019, retrieved on Nov. 6, 2023, retrieved from URL<https://bioinformatics.stackexchange.com/posts/10623/timeline>, 3 pages.

BioInformatics.StackExchange.com [online], "User Profile for Luhui Zhang," user profile created Oct. 22, 2019, retrieved on Nov. 8, 2023, retrieved from URL<https://bioinformatics.stackexchange.com/users/6384/luhui-zhang>, 1 page.

Bolukbasi et al., "Creating and evaluating accurate CRISPR-Cas9 scalpels for genomic surgery," Nat Meth, Jan. 2016, 13: 41-50.

Briggs et al., "Removal of deaminated cytosines and detection of in vivo methylation in ancient DNA," Nucleic Acids Research, Apr. 2010, 38(6):e87, 12 pages.

Cameron et al., "Mapping the genomic landscape of CRISPR-Cas9 cleavage," Nature Methods, 2017, 10 pages.

Canela et al., "DNA Breaks and End Resection Measured Genome wide by End Sequencing," Molecular Cell, 2016, 63: 1-14.

Canver et al, "BCL11A enhancer dissection by Cas9mediated in situ saturating mutagenesis," Nature, 2015, 527(7577):192-197.

Carroll, "A CRISPR Approach to Gene Targeting," Molecular Therapy, Sep. 2012, 20:(9)1658-1660.

Casini et al, "A highly specific SpCas9 variant is identified by in vivo screening in yeast," Nat. Biotechnol., Mar. 2018, 36(3):265-271.

(56)        References Cited

OTHER PUBLICATIONS

Cencic et al., "Protospacer Adjacent Motif (PAM)-Distal Sequences Engage CRISPR Cas9 DNA Target Cleavage," Oct. 2014, PLOS One, 9(10): e109213.

Chavez et al., "Highly-efficient Cas9-mediated transcriptional programming," Nat. Meth., Apr. 2015, 12(4):326-328, 5 pages.

Chen & Zhao, "A highly sensitive selection method for directed evolution of homing endonucleases," Nucleic Acids Res., Oct. 2005, 33, e154, 7 pages.

Chen et al., "Enhanced proofreading governs CRISPR-Cas9 targeting accuracy," Nature, Oct. 2017, 550(7676):407-410.

Cho et al., "Analysis of off-target effects of CRISPR/Case-derived RNA-guided endonucleases and nickases," Genome Res., 2014, 24:132-141.

Cho et al., "Targeted genome engineering in human cells with the Cas9 RNA-guided endonuclease," Nat Biotechnol., 2013, 31:230-232.

Choi & Meyerson, "Targeted genomic rearrangements using CRISPR/Cas technology," Nat Commun., Apr. 24, 2014, 5:3728, doi: 10.1038/ncomms4728.

Chylinski et al, "The tracrRNA and Cas9 families of type II CRISPR-Cas immunity systems," RNA Biol., May 2013, 10:726-737.

CN Office Action in Chinese Appln. No. 201580045542, dated Jul. 14, 2020, 29 pages (with English translation).

CN Office Action in Chinese Appln. No. 201580045542.3, dated Feb. 3, 2020, 19 pages, (with English translation).

CN Office Action in Chinese Appln. No. 201580045542.3, dated Jul. 22, 2019, 25 pages, (with English translation).

CN Office Action in Chinese Appln. No. 201580045542.3, dated Feb. 1, 2021, 14 pages (with English translation).

CN Office Action in Chinese Appln. No. 201680065929.X, dated Jan. 29, 2021, 21 pages (with English translation).

Cole, "Site-specific protein labeling with SNAP-tags," HHS Public Access Author Manuscript, doi: 10.1002/0471140864.ps3001s73, published online Sep. 24, 2014; published in final edited form as Curr Protoc Protein Sci., Sep. 2013, 73:30.1.1-30.1.16, 19 pages.

Cong et al., "Multiplex genome engineering using CRISPR/Cas systems," Science, 2013, 339:819-823 (Author Manuscript).

Courtney et al, "CRISPR/Cas9 DNA cleavage at SNP-derived PAM enables both in vitro and in vivo KRT12 mutation-specific targeting," Gene. Ther., Aug. 2015, 23(1):108-12.

Cox et al., "Therapeutic genome editing: prospects and challenges," Nat Med, 2015, 21: 121-131.

Cradick et al., "CRISPR/Cas9 systems targeting beta-globin and CCR5 genes have substantial off-target activity," Nucleic Acids Res., 2013, 41(20):9584-92.

Crosetto et al, "Nucleotide-resolution DNA double-strand break mapping by next-generation sequencing," Nat Methods, Apr. 2013, 10(4): 361-365.

Declaration and Curriculum Vitae of Dr. Fyodor D. Urnov, dated Nov. 18, 2023, 20 pages.

Deltcheva et al, "CRISPR RNA maturation by trans-encoded small RNA and host factor RNase III," Nature, Mar. 2011, 471(7340):602-607.

DiCarlo et al., "Genome engineering in Saccharomyces cerevisiae using CRISPR-Cas systems," Nucleic Acids Res, 2013, pp. 1-8.

Dieffrenbach et al., "General concepts for PCR primer design," Genome Research, PCR Methods Appl, Dec. 1993, 3(3):S30-7.

Doudna & Charpentier, "The new frontier of genome engineering with CRISPR-Cas9," Science, Nov. 2014, 346(6213):1258096, 10 pages.

Doyon et al, "Directed evolution and substrate specificity profile of homing endonuclease I-Scel," J. Am. Chem. Soc., 2006, 128:2477-2484.

Du et al., "Quantitative assessment of HR and NHEJ activities via CRISPR/Cas9-induced oligodeoxynucleotide-mediated DSB repair," DNA Repair, Sep. 2018, 70:67-71.

Duan et al., "Genome-wide identification of CRISPR/Cas9 off-targets in human genome," Cell Res, 2014, 24(8):1009-1012.

EP Extended European Search Report in Application No. 16845183. 9, dated Jan. 18, 2019, 11 pages.

EP Extended European Search Report in Application No. 16852752. 1, dated Feb. 20, 2019, 11 pages.

EP Extended European Search Report in European Application No. 15812186.3, dated Oct. 19, 2017, 7 pages.

EP Office Action in European Application No. 15812186.3, dated Jun. 15, 2018, 4 pages.

EP Office Action in European Appln. No. 15812186.3, dated Aug. 28, 2019, 4 pages.

EP Office action in European U.S. Appl. No. 16/845,183, dated Jun. 9, 2020, 7 pages.

EP Office Action in European Appln. No. 16852752.1, dated Jan. 29, 2020, 4 pages.

EP Office Action in European Appln. No. 16852752.1, dated Nov. 3, 2020, 5 pages.

Esvelt et al, "Orthogonal Cas9 proteins for RNA-guided gene regulation and editing," Nat. Methods, Sep. 2013, 10:1116-1121.

Extended European Search Report in European Appln. No. 19788161. 8, dated Dec. 23, 2021, 8 pages.

FDA Briefing Document BLA# 125787/0, dated Oct. 31, 2023, 37 pages.

Fitch, "Distinguishing Homologous From Analogous Proteins," Systematic Zoology, Jun. 1970, 19(2):99-113.

Fonfara et al., "Phylogeny of Cas9 determines functional exchangeability of dual-RNA and Cas9 among orthologous type II CRISPR-Cas systems," Nucleic Acids Res., 2014, 42(4): 2577-2590.

Frangoul et al., "CRISPR-Cas9 Gene Editing for Sickle Cell Disease and β-Thalassemia," The New England Journal of Medicine, Jan. 2021, 384:252-260.

Frock et al., "Genome-wide detection of DNA double-stranded breaks induced by engineered nucleases," Nat Biotechnol, Feb. 2015, 33: 179-186.

Fu et al., "High-frequency off-target mutagenesis induced by CRISPR-Cas nucleases in human cells," Nat Biotechnol., 2013, 31:822-826 (Author Manuscript).

Fu et al., "Improving CRISPR-Cas nuclease specificity using truncated guide RNAs," Nat Biotechnol, Mar. 2014, 32(3): 279-284.

Gabriel et al., "An unbiased genome-wide analysis of zinc-finger nuclease specificity," Nat Biotechnol, Sep. 2011, 29(9): 816-823.

Gagnon et al, "Efficient mutagenesis by Cas9 protein-mediated oligonucleotide insertion and large-scale assessment of single-guide RNAs," PLoS One, 2014, 9, e98186.

Gaj et al., "ZFN, TALEN and CRISPR/Cas-based methods for genome engineering," Trends Biotechnol,, Jul. 2013, 31(7):397-405.

Garibyan and Avashia, "Research Techniques Made Simple: Polymerase Chain Reaction (PCR)," HHS Public Access Author Manuscript, doi: 10.1038/jid.2013.1, published online Jul. 17, 2014, published in final edited form as: J Invest Dermatol., Mar. 2013, 133(3):e6, 8 pages.

Gasiunas et al., "Cas9-crRNA ribonucleoprotein complex mediates specific DNA cleavage for adaptive immunity in bacteria," Proceedings of the National Academy of Sciences, Sep. 2012, E2579-E2586.

Gaudelli et al, "Programmable base editing of A•T to G•C in genomic DNA without DNA cleavage," Nature, Nov. 2017, 23;551(7681):464-471.

Ghezraoui et al., "Chromosomal translocations in human cells are generated by canonical nonhomologous end-joining," Mol Cell, Sep. 18, 2014, 55: 829-842.

Gnirke et al., "Solution hybrid selection with ultra-long oligonucleotides for massively parallel targeted sequencing," Nature Biotechnology, 2009, 27: 182-189.

Gori et al., "Delivery and Specificity of CRISPR-Cas9 Genome Editing Technologies for Human Gene Therapy," Hum Gene Ther, 2015, 26: 443-451.

Gostissa et al., "IgH class switching exploits a general property of two DNA breaks to be joined in cis over long chromosomal distances," Proc Natl Acad Sci, Feb. 18, 2014, 111(7): 2644-2649.

Guilinger et al., "Broad specificity profiling of TALENs results in engineered nucleases with improved DNA-cleavage specificity," Nat. Meth., Apr. 2014, 11(4):429-435, 9 pages.

(56) References Cited

OTHER PUBLICATIONS

Guilinger et al., "Fusion of catalytically inactive Cas9 to FokI nuclease improves the specificity of genome modification," Nat Biotechnol, Jun. 2014, 32(6): 577-582.

Hale et al, "Essential Features and Rational Design of CRISPR RNAs That Function With the Cas RAMP Module Complex to Cleave RNAs," Molecular Cell, Feb. 2012, 45(3):292-302.

Heigwer et al., "E-CRISP: fast CRISPR target site identification," Nat Methods, Feb. 2014, 11: 122-123.

Hess et al., "Methods and Applications of CRISPR-Mediated Base Editing in Eukaryotic Genomes," Molecular Cell, 2017, 68:26-43.

Holtz et al., "APOBEC3G cytosine deamination hotspots are defined by both sequence context and single-stranded DNA secondary structure," Nucleic Acids Research, Jul. 2013, 41(12):6139-6148.

Horvath et al., "Diversity, activity, and evolution of CRISPR loci in Streptococcus thermophiles," J Bacteriol, 2008, 190, 1401-1412.

Hou et al., "Efficient genome engineering in human pluripotent stem cells using Cas9 from Neisseria meningitidis," Proc. Natl. Acad Sci USA, Sep. 2013, 110(39):15644-15649.

Hsu et al., "Development and Applications of CRISPR-Cas9 for Genome Engineering," Cell, 2014, 157(6):1262-1278.

Hsu et al., "DNA targeting specificity of RNA-guided Cas9 nucleases," Nat Biotechnol., 2013, 31:827-832.

Hwang et al., "Efficient In Vivo Genome Editing Using RNA-Guided Nucleases," Nat Biotechnol., 2013, 31:227-229 (Author Manuscript).

IL Office Action in Israeli Appln. No. 249555, dated Dec. 16, 2019, 6 pages (with English translation).

IL Office Action in Israeli Appln. No. 257955, dated May 1, 2020, 6 pages (with English translation).

IN Office Action in Indian Application No. 201617043121, dated Dec. 8, 2020, 6 pages.

Ishino et al, "Identification of a mismatch-specific endonuclease in hyperthermophilic Archaea," Nucleic Acids Res., Apr. 2016, 44(7): 2977-2986.

Jiang et al., "Characterization of Escherichia coli Endonuclease VIII," J. Biol. Chem, 1997, 272:32230-32239.

Jiang et al., "CRISPR-assisted editing of bacterial genomes," Nat Biotechnol, Mar. 2013, 31(3): 233-239.

Jinek et al., "A programmable dual-RNA-guided DNA endonuclease in adaptive bacterial immunity," Science, 2012, 337:816-821.

Jinek et al., "RNA-programmed genome editing in human cells," Elife, 2013, 2:e00471, 9 pages.

JP Office Action in Japanese Appln. No. 2016-575174, dated May 12, 2020, 6 pages (with English translation).

JP Office Action in Japanese Appln. No. 2016-575174, dated Jul. 9, 2019, 12 pages (with English translation).

JP Office Action in Japanese Appln. No. 2018-513347, dated Sep. 15, 2020, 11 pages (with English translation).

JP Office Action in Japanese Appln. No. 2018-516489, dated Jul. 21, 2020, 8 pages (with English translation).

Karimi-Busheri et al., "Human polynucleotide kinase participates in repair of DNA double-strand breaks by nonhomologous end-joining but not homologous recombination," Cancer Research, Jul. 2007, 67(14):6619-6625.

Keegan et al, "ADAR RNA editing below the backbone," RNA, Sep. 2017, 23(9):1317-1328.

Kim et al, "Increasing the genome-targeting scope and precision of base editing with engineered Cas9-cytidine deaminase fusions," Nat Biotechnol., Apr. 2017, 35(4):371-376.

Kim et al., "Digenome-seq: genome-wide profiling of CRISPR-Cas9 off-target effects in human cells," Nat Meth, Mar. 2015, 12: 237-243.

Kim et al., "Genome-wide target specificities of CRISPR RNA-guided programmable deaminases," Nat. Biotech., May 2017, 35(5):475-480.

Kim et al., "Genome-wide target specificities of CRISPR-Cas9 nucleases revealed by multiplex Digenome-seq," Genome Res, 2016, 26: 406-415.

Kim et al., "Genome-wide target specificity of CRISPR RNA-guided adenine base editors," Nature Biotechnology, Apr. 2019, 37(4):430-435, 9 pages.

Kleinstiver et al, "A unified genetic, computational and experimental framework identifies functionally relevant residues of the homing endonuclease I-BmoI," Nucleic Acids Res., 2010, 38(7):2411-2427.

Kleinstiver et al, "Broadening the targeting range of Staphylococcus aureus CRISPR-Cas9 by modifying PAM recognition," Nature, Dec. 2015, 33(12):1293-1298.

Kleinstiver et al, "Engineered CRISPR-Cas9 nucleases with altered PAM specificities," Nature, Jun. 2015, 523(7561):481-485.

Kleinstiver et al., "High-fidelity CRISPR-Cas9 nucleases with no detectable genome-wide off-target effects," Nature, Jan. 2016, 529: 490-495.

Komor et al, "Improved base excision repair inhibition and bacteriophage Mu Gam protein yields C:G-to-T:A base editors with higher efficiency and product purity," Sci. Adv., Aug. 2017, 3:eaao4774, 9 pages.

Komor et al, "Programmable editing of a target base in genomic DNA without double-stranded DNA cleavage," Nature, May 2016, 533(7603):420-424.

Kuraoka "Diversity of Endonuclease V: From DNA Repair to RNA Editing" Biomolecules, Dec. 2015, 5(4):2194-2206.

Kuscu et al., "Genome-wide analysis reveals characteristics of off-target sites bound by the Cas9 endonuclease," Nat Biotechnol, Jul. 2014, 32 (7): 677-683.

Lazzarotto et al., "CHANGE-seq reveals genetic and epigenetic effects on CRISPR-Cas9 genome-wide activity," Nat Biotechnol., Nov. 2020, 38(11):1317-1327, 39 pages.

Lazzarotto et al., "Defining CRISP-Cas9 genome-wide nuclease activities with CIRCLE-seq," Nature Protocols, Oct. 2018, 13: 2615-2642.

Lee et al., "Expression-level optimization of a multi-enzyme pathway in the absence of a high-throughput assay," Nucleic Acids Research, Sep. 2013, 41(22):10668-10678.

Liang et al., "Genome-wide profiling of adenine base editor specificity by Endo V-seq," Nature Communications, Jan. 2019, 10(1):67, 9 pages.

Liang et al., "Off-target effects of cytidine base editor and adenine base editor: What can we do?," Journal of Genetics and Genomics, 2019, 46:509-512.

LifeScience.net [online], "Blunting and phosphorylation of DNA prior to blunt-end ligation," Jul. 26, 2016, retrieved on May 19, 2023, retrieved from URL<https://www.lifescience.net/protocols/935/blunting-and-phosphorylation-of-dna-prior-to-blunt/>, 1 page.

Lin et al., "CRISPR/Cas9 systems have off-target activity with insertions or deletions between target DNA and guide RNA sequences," Nucleic Acids Res, 2014, 42(11): 7473-7485.

Lindahl et al., "DNA N-glycosidases: properties of uracil-DNA glycosidase from Escherichia coli," J. Biol. Chem., May 1977, 252:3286-3294.

Lindahl, "DNA repair enzymes," Annu. Rev. Biochem, 1982, 51:61-64.

Makarova et al., "Evolution and classification of the CRISPR-Cas systems," Nature Reviews Microbiology, Jun. 2011, 9(6):467-477.

Mali et al, "CAS9 transcriptional activators for target specificity screening and paired nickases for cooperative genome engineering," Nat Biotechnol, Sep. 2013, 31(9): 833-838.

Mali et al., "RNA-guided human genome engineering via Cas9," Science, Feb. 2013, 339:823-826 (Author Manuscript).

Malinin et al., "Defining genome-wide CRISPR-Cas genome-editing nuclease activity with GUIDE-seq," Nature Protocols, Dec. 2021, 16:5592-5615.

Marx et al., "Gene editing: how to stay on-target with CRISPR," Nat Methods, 2014, 11:1021-1026.

Melamede et al., "Isolation and characterization of endonuclease VIII from Escherichia coli," Biochemistry, Feb. 1994, 33:1255-1264.

Miller et al. "A TALE nuclease architecture for efficient genome editing," Nat. Biotech., Feb. 2011, 29(2):143-150.

(56) References Cited

OTHER PUBLICATIONS

Mojica et al, "Short motif sequences determine the targets of the prokaryotic CRISPR defence system," Microbiology, Jan. 2009, 155:733-740.

Mullis and Faloona, "Specific synthesis of DNA in vitro via a polymerase-catalyzed chain reaction," Methods in Enzymology, 1987, 155: 335-350.

Nhm.ac.uk [online], "Blunting of DNA," Nov. 11, 2012, retrieved on Apr. 14, 2020, retrieved from URL <https://www.nhm.ac.uk/content/dam/nhmwww/our-science/dpts-facilities-staff/Coreresearchlabs/blunting-of-dna_aug12.pdf>, 1 page.

Nishida et al, "Targeted nucleotide editing using hybrid prokaryotic and vertebrate adaptive immune systems," Science, Sep. 2016, 53(6305), 14 pages.

Nishimasu al, "Crystal Structure of Cas9 in Complex with Guide RNA and Target DNA," Cell, Feb. 2014, 156(5):935-949.

Notice of Allowance in Japanese Appln. No. 2020-557220, dated Feb. 20, 2024, 5 pages (with English translation).

Ochman et al., "Genetic Applications of an Inverse Polymerase Chain Reaction," Genetics, Nov. 1998, 120:621-623.

Office Action in Chinese Appln. No. 201980040610.5, dated May 1, 2024, 14 pages (with English translation).

Office Action in Japanese Appln. No. 2020-557220, dated Aug. 8, 2023, 4 pages (with English translation).

Office Action in Japanese Appln. No. 2020-557220, dated Jan. 10, 2023, 16 pages (with English translation).

Oliphant et al., "Defining the sequence specificity of DNA-binding proteins by selecting binding sites from random-sequence oligonucleotides: analysis of yeast GCN4 protein," Mol. Cell. Biol., Jul. 1989, 9(7):2944-2949.

Orlando et al., "Zinc-finger nuclease-driven targeted integration into mammalian genomes using donors with limited chromosomal homology," Nucleic Acids Res, 2010, 38(15): e152.

Osborn et al., "TALEN-based gene correction for epidermolysis bullosa," Mol Ther, 2013, 21: 1151-1159.

Pattanayak et al., "High-throughput profiling of off-target DNA cleavage reveals RNA-programmed Cas9 nuclease specificity," Nat Biotechnol., 2013, 31:839-843 (Author Manuscript).

Pattanayak et al., "Revealing off-target cleavage specificities of zinc-finger nucleases by in vitro selection," Nat. Meth., Aug. 2011, 8(9):765-770.

PCT International Preliminary Report on Patentability in International Application No. PCT/US2016/051097, dated Mar. 13, 2018, 10 pages.

PCT International Preliminary Report on Patentability in International Application No. PCT/US2016/054912, mailed on Apr. 12, 2018, 10 pages.

PCT International Preliminary Report on Patentability in International Application No. PCT/US2018/047577, dated Feb. 25, 2020, 8 pages.

PCT International Preliminary Report on Patentability in International Application No. PCT/US2019/027788, dated Oct. 20, 2020, 16 pages.

PCT International Preliminary Report on Patentability in International Appln. No. PCT/US2018/055406, dated Apr. 14, 2020, 8 pages.

PCT International Search Report and Written Opinion in International Application No. PCT/US15/37269, dated Oct. 15, 2015, 26 pages.

PCT International Search Report and Written Opinion in International Application No. PCT/US16/51097, mailed on Jan. 24, 2017, 12 pages.

PCT International Search Report and Written Opinion in International Application No. PCT/US16/54912, mailed on Jan. 24, 2017, 12 pages.

PCT International Search Report and Written Opinion in International Application No. PCT/US19/27788, mailed on Aug. 5, 2019, 19 pages.

PCT International Search Report and Written Opinion in International Appln. No. PCT/US18/55406, dated Jan. 17, 2019, 10 pages.

Perez et al., "Establishment of HIV-1 resistance in CD4+ T cells by genome editing using zinc-finger nucleases," Nat. Biotech., Jul. 2008, 26(7):808-816.

Pinello et al., "Analyzing CRISPR genome-editing experiments with CRISPResso," Nat. Biotechnol., Jul. 2016, 34(7): 695-697.

Ran et al., "Double nicking by RNA-guided CRISPR Cas9 for enhanced genome editing specificity," Cell, Sep. 2013, 154: 1380-1389.

Ran et al., "Supplemental Information: Double nicking by RNA-guided CRISPR Cas9 for enhanced genome editing specificity," Cell, Sep. 2013, 5 pages.

Ran et al., "Genome engineering using the CRISPR-Cas9 system," Nat Protoc, Nov. 2013, 8(11):2281-2308.

Ran et al., "In vivo genome editing using *Staphylococcus aureus* Cas9," Nature, Apr. 2015, 520, 186-191.

Rebhandl et al., "AID/APOBEC Deaminases and Cancer." Oncoscience, Apr. 2015, 2(4):320-333.

Rees & Liu, "Base editing: precision chemistry on the genome and transcriptome of living cells," Nat. Rev. Genet., Dec. 2018, 19(12):770-788, 19 pages.

Reyon et al, "FLASH assembly of TALENS for high-throughput genome editing," Nat. Biotechnol., May 2012, 30(5):460-465.

Sander and Joung, "CRISPR-Cas systems for editing, regulating and targeting genomes," Nat Biotechnol., Apr. 2014, 32(4):347-55.

Sander et al., "In silico abstraction of zinc finger nuclease cleavage profiles reveals an expanded landscape of off-target sites," Nucleic Acids Res, Oct. 2013, 41(19): e181.

Sapranauskas et al., "The *Streptococcus thermophilus* CRISPR/Cas system provides immunity in *Escherichia coli*," Nucleic Acids Res., Aug. 2011, 39(21):9275-9282.

Savva et al., "The ADAR protein family," Genome Biol., Dec. 2012, 13(12):252, 10 pages.

Schaub and Keller, "RNA editing by adenosine deaminases generates RNA and protein diversity," Biochimie, Aug. 2002, 84(8):791-803.

Schmidt et al., "High-resolution insertion-site analysis by linear amplification-mediated PCR (LAM-PCR)," Nat Methods, Dec. 2007, 4(12): 1051-1057.

Shah et al, "Protospacer recognition motifs," RNA Biol., Feb. 2013, 10(5):891-899.

Shapiro et al., "Increasing CRISPR Efficiency and Measuring its Specificity in HSPCs using a clinically relevant system," Molecular Therapy Methods and Clinical Development, May 2020, 17:1097-1107.

Shen et al., "Generation of gene-modified mice via Cas9/RNA-mediated gene targeting," Cell Res, 2013, 23:720-723.

Shi et al., "GUIDE-Seq to detect genome-wide double-stranded breaks in plants," Cell Press, Oct. 2016, 21(10):815-818.

Shinohara et al., "APOBEC3B can impair genomic stability by inducing base substitutions in genomic DNA in human cells." Scientific Reports, Nov. 2012, 2(806), 9 pages.

Slaymaker et al, "Rationally engineered Cas9 nucleases with improved specificity," Science, Jan. 2016, 351(6268):84-88.

Sloan et al., "Detecting rare mutations and DNA damage with sequencing-based methods," Trends in Biotechnology, Jul. 2018, 36(7):729-740, 12 pages.

Smith et al, "Whole-genome sequencing analysis reveals high specificity of CRISPR/Cas9 and TALEN-based genome editing in human iPSCs," Cell Stem Cell, Jul. 3, 2014, 15(1):12-13.

Sternberg et al, "DNA interrogation by the CRISPR RNA-guided endonuclease Cas9," Nature, Jan. 2014, 507(7490):62-67.

Suspène et al., "Erroneous Identification of APOBEC3-edited Chromosomal DNA in Cancer Genomics," British Journal of Cancer, May 2014, 110(10):2615-2622.

Suspène et al., "Extensive editing of both hepatitis B virus DNA strands by APOBEC3 cytidine deaminases in vitro and in vivo." Proceedings of the National Academy of Sciences of the United States of America, Jun. 2005, 102(23):8321-8326.

Suspène et al., "Recovery of APOBEC3-edited human immunodeficiency virus G→ A hypermutants by differential DNA denaturation PCR," Journal of General Virology, Jan. 2005, 86(1):125-129.

(56)        References Cited

OTHER PUBLICATIONS

Thakore et al., "Highly specific epigenome editing by CRISPR-Cas9 repressors for silencing of distal regulatory elements," Nat. Meth., Dec. 2015, 12(12):1143-1149, 9 pages.

thermofisher.com {online}. "PCR Methods-Top Ten Strategies," 2017, [retrieved on Feb. 1, 2017], Retrieved from the Internet: URL<https://www.thermofisher.com/US/en/home/life-science/cloning/cloning-learningcenter/invitrogen-school-of-molecular-biology/per-education/per-reagents-enzymes/per-methods.html>. 10 pages.

Tsai and Joung, "Defining and improving the genome-wide specificities of CRISPR-Cas9 nucleases," Nature, Apr. 2016, 17: 300-312.

Tsai et al., "CIRCLE-seq: a highly sensitive in vitro screen for genome-wide CRISPR-Cas9 nuclease off-targets," Nature Methods, May 2017, 14: 607-614.

Tsai et al., "Dimeric CRISPR RNA-guided FokI nucleases for highly specific genome editing," Nat Biotechnol, Jun. 2014, 32(6): 569-576.

Tsai et al., "GUIDE-seq Enables Genome-Wide Profiling of Off-Target Cleavage by CRISPR-Cas Nucleases," Nature Biotechnology, Dec. 2014, 187-197.

Tsai et al., "Supplementary Information: GUIDE-seq Enables Genome-Wide Profiling of Off-Target Cleavage by CRISPR-Cas Nucleases," Nature Biotechnology, Jun. 2015, 52 pages.

Tsai et al., "What's changed with genome editing?," Cell Stem Cell, Jul. 2014, 15(1):3-4.

Vakulskas et al, "A high-fidelity Cas9 mutant delivered as a ribonucleoprotein complex enables efficient gene editing in human haematopoietic stem and progenitor cells," Nature Medicine, Aug. 2018, 24(8):1216-1224.

Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.

Vierstra et al, "Functional footprinting of regulatory DNA," Nat. Methods, Oct. 2015, 12(10):927-30.

Wiedenheft et al, "RNA-guided genetic silencing systems in bacteria and archaea," Nature, Feb. 2012, 482:331-338.

Wienert et al., "Unbiased detection of CRISPR off-targets in vivo using DISCOVER-Seq," Science, Apr. 2019, 364(6437):286-289.

Wolf et al, "tadA, an essential tRNA-specific adenosine deaminase from Escherichia coli," EMBO J., Jul. 2002, 21(14):3841-3851.

Wu et al. "Evolution of Inosine-Specific Endonuclease V from Bacterial DNase to Eukaryotic RNase" Molecular Cell, Oct. 2019, 76(1):44-56, 17 pages.

Wu et al., "Genome-wide binding of the CRISPR endonuclease Cas9 in mammalian cells," Nat Biotechnol., Jul. 2014, 32(7):670-6.

Yang et al. "Engineering and optimising deaminase fusions for genome editing" Nature Communications, Nov. 2016, 7(1):1-11.

Yang et al., "Targeted and genome-wide sequencing reveal single nucleotide variations impacting specificity of Cas9 in human stem cells," Nature Communications, Nov. 2014, 5: 5507.

Zentner & Henikoff., "Epigenome editing made easy," Nat. Biotech., Jun. 2015, 33(6):606-607.

Zhang et al, "Processing-Independent CRISPR RNAs Limit Natural Transformation in Neisseria meningitidis," Mol. Cell, May 2013, 50:488-503.

Zheng et al., "Anchored multiplex PCR for targeted next-generation sequencing," Nat Med, Nov. 10, 2014, 20(12): 1479-1484.

Office Action in Australian Appln. No. 2019256287, mailed on Mar. 27, 2025, 4 pages.

Office Action in European Appln. No. 19788161.8, mailed on May 20, 2025, 3 pages.

Office Action in Australian Appln. No. 2019256287, mailed on Nov. 12, 2025, 3 pages.

Office Action in Canadian Appln. No. 3,097,044, mailed on Oct. 15, 2025, 7 pages.

* cited by examiner base substitution libraries

SEQ ID NO:1   GCAGATGTAGTGTTTCCACAGGG
SEQ ID NO:2   GaAGATGTAGTGTTTCCACAGGG
SEQ ID NO:3   GCcGATGTAGTGTTTCCACAGGG
SEQ ID NO:4   GCAaATGTAGTGTTTCCACAGGG
SEQ ID NO:5   GCAGccGTAGTGTTTCCACAGGG
SEQ ID NO:6   GCAGcTaTAGTGTTTCCACAGGG small set of defined single or double base
pair substitutions SEQ ID NO:1   GCAGATGTAGTGTTTCCACAGGG
SEQ ID NO:7   aCAGATtTAGgGTTTCCACAGGG
SEQ ID NO:8   GCAGATGaAGTGTacCCcCtGGG
SEQ ID NO:9   GCAGATGagGTcaTcCCACAGGG
SEQ ID NO:10   aCAtATGaAGTGTTTgyttAGGc
SEQ ID NO:11   GCAGATaTAGTGcgTCCcCAGGG large set of sequences with a distribution of
mutations genomic DNA libraries

GCAGATGTAGTGTTTCCACAGGG   SEQ ID NO:1
AAGTGAGGTTGCCTGCCCTGTCT   SEQ ID NO:12
CCTACCTGAGGCTGAGGAAGGAG   SEQ ID NO:13
GGTCACCTACAGCACCGAGTGTG   SEQ ID NO:14
AGCTGAAGAAGGCCAGGTGTGAG   SEQ ID NO:15
CTGTAGCAGGATGAGCCGCAGAC   SEQ ID NO:16 potential off-target sequences are rare
compared to the other unrelated ~3 x 10⁹
sequences in the genome

*FIG. 1*

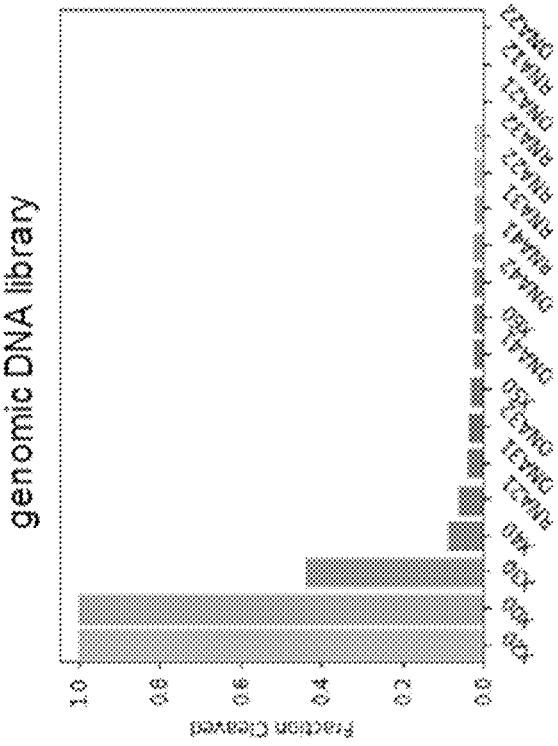
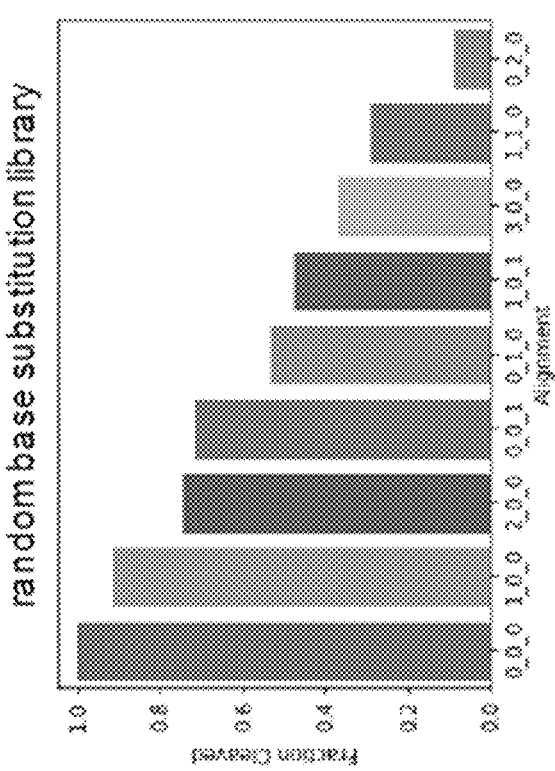
*FIG. 5*

| bulge type | bulge size | mismatches | ABE14 | ABE16 | ABE18 | EMX1 | FANCF | HBB | HEK2 | HEK3 | HEK4 | RNF2 | VEGFA3 |
|---|---|---|---|---|---|---|---|---|---|---|---|---|---|
| no bulge | 0 | 0 | 1 | 1 | 1 | 1 | 1 | 1 | 1 | 1 | 1 | 1 | 1 |
|  | 0 | 1 | 1 | 0 | 1 | 0 | 0 | 0 | 0 | 0 | 0 | 0 | 1 |
|  | 0 | 2 | 1 | 0 | 4 | 1 | 2 | 4 | 1 | 1 | 9 | 0 | 35 |
|  | 0 | 3 | 9 | 20 | 73 | 25 | 31 | 51 | 14 | 14 | 116 | 10 | 1041 |
|  | 0 | 4 | 151 | 259 | 814 | 398 | 421 | 610 | 225 | 141 | 1149 | 199 | 22465 |
|  | 0 | 5 | 1713 | 3072 | 6528 | 4013 | 2778 | 5757 | 2904 | 1706 | 8446 | 1868 | 0 |
|  | 0 | 6 | 14601 | 30685 | 44576 | 30914 | 19151 | 44090 | 24602 | 14119 | 47599 | 16426 | 0 |
| DNA | 1 | 1 | 0 | 0 | 1 | 0 | 0 | 0 | 0 | 0 | 0 | 0 | 1 |
|  | 2 | 1 | 0 | 0 | 0 | 0 | 0 | 0 | 0 | 1 | 1 | 0 | 0 |
|  | 1 | 2 | 1 | 3 | 20 | 6 | 2 | 1 | 5 | 0 | 13 | 2 | 61 |
|  | 2 | 2 | 1 | 2 | 0 | 7 | 4 | 15 | 6 | 6 | 7 | 6 | 0 |
|  | 1 | 3 | 49 | 74 | 327 | 133 | 75 | 106 | 128 | 65 | 356 | 67 | 0 |
|  | 2 | 3 | 53 | 92 | 48 | 127 | 92 | 258 | 138 | 60 | 242 | 74 | 0 |
|  | 1 | 4 | 745 | 1284 | 4013 | 2283 | 1062 | 2006 | 2176 | 1001 | 5625 | 1167 | 0 |
|  | 2 | 4 | 853 | 1675 | 1193 | 1988 | 1645 | 3752 | 2512 | 1114 | 3365 | 1151 | 0 |
| RNA | 1 | 1 | 0 | 0 | 0 | 0 | 1 | 0 | 0 | 0 | 3 | 0 | 12 |
|  | 2 | 1 | 0 | 0 | 0 | 1 | 4 | 0 | 3 | 3 | 7 | 0 | 0 |
|  | 1 | 2 | 8 | 14 | 55 | 17 | 12 | 11 | 22 | 30 | 74 | 5 | 338 |
|  | 2 | 2 | 59 | 55 | 19 | 164 | 63 | 121 | 87 | 42 | 243 | 59 | 0 |
|  | 1 | 3 | 244 | 348 | 920 | 576 | 223 | 380 | 485 | 297 | 1074 | 316 | 0 |
|  | 2 | 3 | 790 | 1777 | 931 | 7804 | 1431 | 2883 | 1496 | 949 | 3777 | 1382 | 0 |
|  | 1 | 4 | 4242 | 5024 | 10263 | 8520 | 3779 | 7248 | 8149 | 4227 | 13197 | 4589 | 0 |
|  |  | total | 23522 | 44385 | 69787 | 56978 | 30777 | 67294 | 42954 | 23777 | 85304 | 27322 | 23955 |

FIG. 6

Sequencing Counts

| sgRNA | 90th percentile | 10th percentile | 90/10 ratio | drop out | total | drop out percentage |
|---|---|---|---|---|---|---|
| EMX1 | 23 | 10 | 2.3 | 41 | 51743 | 0.08% |
| FANCF | 42 | 21 | 2 | 15 | 29207 | 0.05% |
| HBB | 56 | 28 | 2 | 1 | 63627 | 0.002% |
| HEK2 | 38 | 18 | 2.1 | 29 | 39533 | 0.07% |
| HEK3 | 59 | 29 | 2.0 | 4 | 22733 | 0.02% |
| HEK4 | 57 | 23 | 2.5 | 157 | 78205 | 0.20% |
| RNF2 | 69 | 34 | 2.0 | 15 | 26102 | 0.06% |
| ABE14 | 45 | 20 | 2.3 | 0 | 22483 | 0.00% |
| ABE16 | 47 | 21 | 2.2 | 0 | 39232 | 0.00% |
| ABE18 | 30 | 12 | 2.5 | 3 | 66580 | 0.00% |
| VEGFA3 | 72 | 30 | 2.4 | 6 | 22364 | 0.03% |
| Mean | 48.9 | 22.4 | 2.2 | 24.6 | 41982.6 | 0.05% |

*FIG. 7*

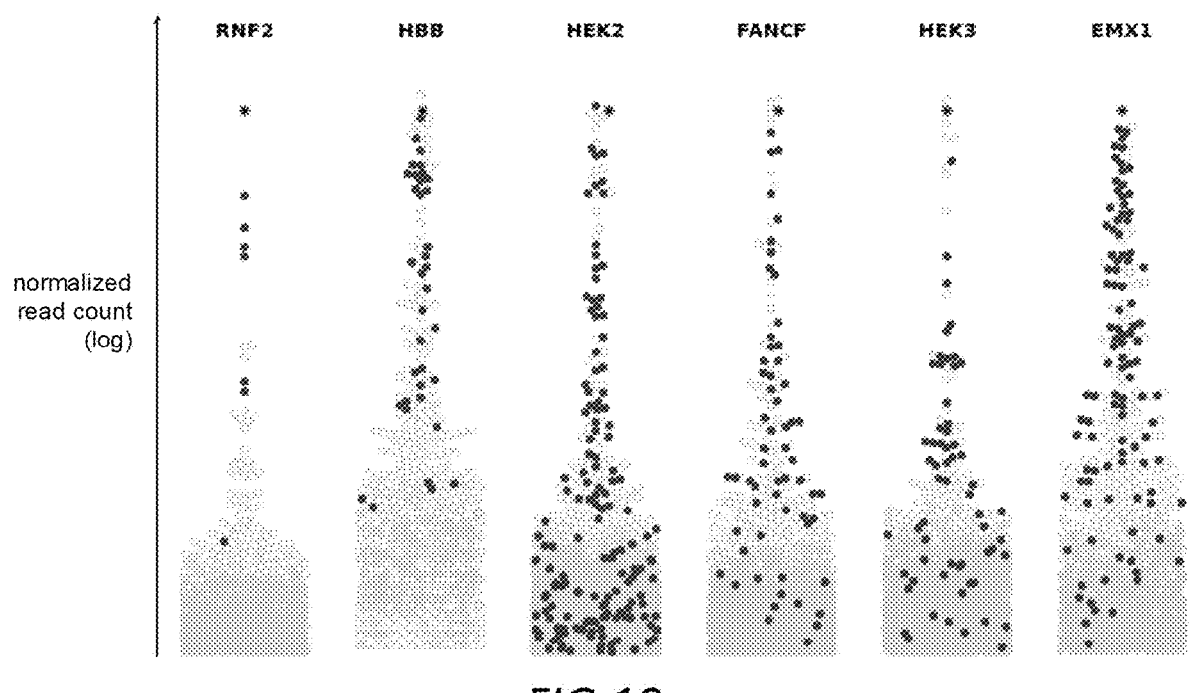
*FIG.10*
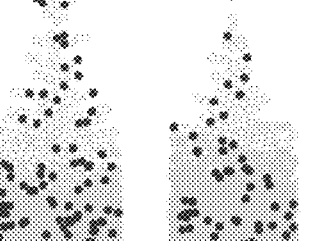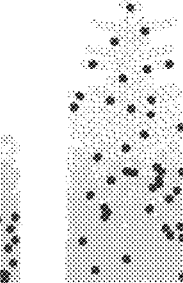
*FIG. 11*

| edit percentage | treated total edited | total reference | control total edited | total reference | reference off-target site | edited site | treated #1 | treated #2 | treated #3 | control #1 | control #1 | control #2 | control #3 |
|---|---|---|---|---|---|---|---|---|---|---|---|---|---|
| | | | | | | | treated and sorted replicates | | | | control replicates | | |
| 0.01% | 36 | 333901 | 0 | 330492 | GGAAgCCCT TCTGcAGCA (SEQ ID NO:24) CCAGa | GGAAGCCCTTCT----ACCAGA (SEQ ID NO:27) | 0 | 8 | 0 | 0 | 0 | 0 | 0 |
| | | | | | | GGAAGCCCTTCTGtAGCcACCACCAGA (SEQ ID NO:28) | 0 | 7 | 0 | 0 | 0 | 0 | 0 |
| | | | | | | GGAAGCCCTTCTGtAGCcACCAGA (SEQ ID NO:29) | 0 | 14 | 7 | 7 | 0 | 0 | 0 |
| 0.01% | 81 | 648232 | 0 | 641626 | (SEQ ID NO:25) GGAATCCCT TCTGCAGCA taGtG | (SEQ ID NO:30) GGAATCCCTTCTGCAGCcAGcATAGTG | 21 | 0 | 0 | 0 | 0 | 0 | 0 |
| | | | | | | GGAATCCCTTCTGCAGCGCATAGTG (SEQ ID NO:31) | 10 | 0 | 15 | 15 | 0 | 0 | 0 |
| | | | | | | GGAATCCCTTCTGCA---TAGTG (SEQ ID NO:32) | 45 | 0 | 0 | 0 | 0 | 0 | 0 |
| 0.03% | 275 | 785676 | 0 | 730960 | (SEQ ID NO:26) GGAAaCCCt TCTGCAGCA CCAGc | GGAAACCCCTCTGCA--CCAGC (SEQ ID NO:33) | 0 | 0 | 0 | 11 | 0 | 0 | 0 |
| | | | | | | GGAAACCCCTCTGCAGCAACCAGC (SEQ ID NO:34) | 0 | 0 | 15 | 15 | 0 | 0 | 0 |
| | | | | | | GGAAACCCCTCTGCAGCAGCAATGCAACAAC (SEQ ID NO:35) | | | | | | | |
| | | | | | | GTTGGCGAAACTATTAACTGGCGAACTACTTAA (SEQ ID NO:35) | 0 | 0 | 9 | 9 | 0 | 0 | 0 |
| | | | | | | GGAAACCCCTCTGCAGCCACCAGC (SEQ ID NO:36) | 0 | 84 | 56 | 56 | 0 | 0 | 0 |
| | | | | | | GGAAACCCCTCTGCAGC-CCAGC (SEQ ID NO:37) | 72 | 0 | 0 | 0 | 0 | 0 | 0 |
| | | | | | | GGAAACCCCTCTGCAGCGCACCAGCGAAAGAAAGAAT (SEQ ID NO:38) | 0 | 0 | 0 | 10 | 0 | 0 | 0 |
| | | | | | | CGTCAACTTTGGCCATTCATTGCTACCAGC (SEQ ID NO:39) | 0 | 18 | 0 | 0 | 0 | 0 | 0 |

*FIG. 13* log(normalized score) of identical sequences from variant-containing library log(normalized score) from original library (SEQ ID NO: 23)

amplify library

BE3

USER adapter ligation

PCR/sequencing target site
barcode
adapter
U  uracil normalized
read count
(log)

HBB   RNF2   FANCF   HEK2   HEK3   ABESite18   EMX1   HEK4

| sgRNA | chromosome | location | off-target sequence | OT | treated Rep1 | treated Rep2 | treated Rep3 | control Rep1 | control Rep2 | control Rep3 |
|---|---|---|---|---|---|---|---|---|---|---|
| RNF2 | chr5 | 92036959 | | OT1 | 0.788 | 0.802 | 0.721 | 0.019 | 0.049 | 0.03 |
| RNF2 | chr6 | 90393053 | | OT2 | 0.224 | 0.321 | 0.255 | 0.0 | 0.0 | 0.0 |
| HEK4 | chr13 | 88900985 | | OT1 | 21.596 | 25.676 | 24.391 | 0.075 | 0.077 | 0.053 |
| HEK4 | chr16 | 49798946 | | OT2 | 9.635 | 10.056 | 9.803 | 0.051 | 0.031 | 0.008 |
| HEK4 | chr3 | 51725445 | | OT3 | 6.937 | 8.122 | 8.848 | 0.009 | 0.011 | 0.062 |
| HEK4 | chr5 | 1832931 | | OT4 | 0.858 | 1.174 | 1.438 | 0.012 | 0.026 | 0.0 |
| HEK4 | chr9 | 5556615 | | OT5 | 0.351 | 0.385 | 0.373 | 0.047 | 0.014 | 0.03 |
| HEK3 | chr5 | 120833004 | | OT1 | 0.253 | 0.359 | 0.284 | 0.0 | 0.0 | 0.0 |
| HEK3 | chr16 | 88931545 | | OT2 | 0.035 | 0.051 | 0.029 | 0.0 | 0.0 | 0.0 |
| HEK2 | chr15 | 93557672 | | OT1 | 0.139 | 0.107 | 0.142 | 0.0 | 0.0 | 0.0 |
| HBB | chr17 | 66624238 | | OT1 | 8.637 | 10.328 | 8.147 | 0.053 | 0.06 | 0.091 |
| HBB | chr2 | 121715223 | | OT2 | 0.569 | 0.755 | 0.511 | 0.0 | 0.0 | 0.0 |
| HBB | chr19 | 923893 | | OT3 | 0.281 | 0.441 | 0.742 | 0.0 | 0.0 | 0.0 |
| HBB | chr15 | 46598112 | | OT4 | 0.201 | 0.261 | 0.141 | 0.0 | 0.0 | 0.0 |
| HBB | chr22 | 17230606 | | OT5 | 0.137 | 0.153 | 0.091 | 0.0 | 0.0 | 0.0 |
| HBB | chr14 | 36889531 | | OT6 | 0.126 | 0.117 | 0.124 | 0.0 | 0.0 | 0.0 |
| HBB | chr12 | 27234748 | | OT7 | 0.119 | 0.17 | 0.129 | 0.0 | 0.0 | 0.0 |
| HBB | chr1 | 17346684 | | OT8 | 0.049 | 0.03 | 0.049 | 0.0 | 0.0 | 0.0 |
| HBB | chrX | 10360008 | | OT9 | 0.034 | 0.027 | 0.078 | 0.0 | 0.0 | 0.0 |
| FANCF | chr22 | 45871974 | | OT1 | 0.273 | 0.275 | 0.353 | 0.0 | 0.0 | 0.0 |
| FANCF | chr6 | 41457558 | | OT2 | 0.046 | 0.066 | 0.05 | 0.0 | 0.0 | 0.0 |
| FANCF | chr16 | 28615183 | | OT3 | 0.124 | 0.134 | 0.087 | 0.0 | 0.0 | 0.0 |
| FANCF | chr17 | 39675782 | | OT4 | 0.082 | 0.057 | 0.178 | 0.0 | 0.004 | 0.0 |
| EMX1 | chr3 | 95690179 | | OT1 | 2.515 | 2.733 | 2.243 | 0.011 | 0.032 | 0.022 |
| EMX1 | chr1 | 151027591 | | OT2 | 0.369 | 0.521 | 0.442 | 0.0 | 0.0 | 0.008 |
| EMX1 | chr15 | 100406507 | | OT3 | 0.292 | 0.255 | 0.313 | 0.01 | 0.015 | 0.022 |
| EMX1 | chr5 | 64109055 | | OT4 | 0.204 | 0.266 | 0.219 | 0.0 | 0.005 | 0.0 |
| EMX1 | chr14 | 75723901 | | OT5 | 0.299 | 0.204 | 0.214 | 0.0 | 0.0 | 0.0 |

*FIG. 20*

(SEQ ID
NO: 23)

relative read count

*FIG. 24*

SEQUENCE LISTING

```
Sequence total quantity: 131
SEQ ID NO: 1            moltype = DNA  length = 23
FEATURE                 Location/Qualifiers
source                  1..23
                        mol_type = other DNA
                        organism = synthetic construct
SEQUENCE: 1
gcagatgtag tgtttccaca ggg                                            23

SEQ ID NO: 2            moltype = DNA  length = 23
FEATURE                 Location/Qualifiers
source                  1..23
                        mol_type = other DNA
                        organism = synthetic construct
SEQUENCE: 2
gaagatgtag tgtttccaca ggg                                            23

SEQ ID NO: 3            moltype = DNA  length = 23
FEATURE                 Location/Qualifiers
source                  1..23
                        mol_type = other DNA
                        organism = synthetic construct
SEQUENCE: 3
gccgatgtag tgtttccaca ggg                                            23

SEQ ID NO: 4            moltype = DNA  length = 23
```

-continued

```
FEATURE             Location/Qualifiers
source              1..23
                    mol_type = other DNA
                    organism = synthetic construct
SEQUENCE: 4
gcaaatgtag tgtttccaca ggg                                              23

SEQ ID NO: 5        moltype = DNA   length = 23
FEATURE             Location/Qualifiers
source              1..23
                    mol_type = other DNA
                    organism = synthetic construct
SEQUENCE: 5
gcagccgtag tgtttccaca ggg                                              23

SEQ ID NO: 6        moltype = DNA   length = 23
FEATURE             Location/Qualifiers
source              1..23
                    mol_type = other DNA
                    organism = synthetic construct
SEQUENCE: 6
gcagctatag tgtttccaca ggg                                              23

SEQ ID NO: 7        moltype = DNA   length = 23
FEATURE             Location/Qualifiers
source              1..23
                    mol_type = other DNA
                    organism = synthetic construct
SEQUENCE: 7
acagatttag ggtttccaca ggg                                              23

SEQ ID NO: 8        moltype = DNA   length = 23
FEATURE             Location/Qualifiers
source              1..23
                    mol_type = other DNA
                    organism = synthetic construct
SEQUENCE: 8
gcagatgaag tgtacccct ggg                                               23

SEQ ID NO: 9        moltype = DNA   length = 23
FEATURE             Location/Qualifiers
source              1..23
                    mol_type = other DNA
                    organism = synthetic construct
SEQUENCE: 9
gcagatgagg tcatcccaca ggg                                              23

SEQ ID NO: 10       moltype = DNA   length = 23
FEATURE             Location/Qualifiers
source              1..23
                    mol_type = other DNA
                    organism = synthetic construct
SEQUENCE: 10
acatatgaag tgtttggtta ggc                                              23

SEQ ID NO: 11       moltype = DNA   length = 23
FEATURE             Location/Qualifiers
source              1..23
                    mol_type = other DNA
                    organism = synthetic construct
SEQUENCE: 11
gcagatatag tgcgtccca ggg                                               23

SEQ ID NO: 12       moltype = DNA   length = 23
FEATURE             Location/Qualifiers
source              1..23
                    mol_type = other DNA
                    organism = synthetic construct
SEQUENCE: 12
aagtgaggtt gcctgccctg tct                                              23

SEQ ID NO: 13       moltype = DNA   length = 23
FEATURE             Location/Qualifiers
source              1..23
                    mol_type = other DNA
                    organism = synthetic construct
SEQUENCE: 13
cctacctgag gctgaggaag gag                                              23
```

-continued

```
SEQ ID NO: 14            moltype = DNA   length = 23
FEATURE                  Location/Qualifiers
source                   1..23
                         mol_type = other DNA
                         organism = synthetic construct
SEQUENCE: 14
ggtcacctac agcaccgagt gtg                                             23

SEQ ID NO: 15            moltype = DNA   length = 23
FEATURE                  Location/Qualifiers
source                   1..23
                         mol_type = other DNA
                         organism = synthetic construct
SEQUENCE: 15
agctgaagaa ggccaggtgt gag                                             23

SEQ ID NO: 16            moltype = DNA   length = 23
FEATURE                  Location/Qualifiers
source                   1..23
                         mol_type = other DNA
                         organism = synthetic construct
SEQUENCE: 16
ctgtagcagg atgagccgca gac                                             23

SEQ ID NO: 17            moltype = DNA   length = 12
FEATURE                  Location/Qualifiers
source                   1..12
                         mol_type = other DNA
                         organism = synthetic construct
SEQUENCE: 17
gctcaatgac gt                                                         12

SEQ ID NO: 18            moltype = DNA   length = 12
FEATURE                  Location/Qualifiers
source                   1..12
                         mol_type = other DNA
                         organism = synthetic construct
SEQUENCE: 18
gctcaatgac gt                                                         12

SEQ ID NO: 19            moltype = DNA   length = 17
FEATURE                  Location/Qualifiers
source                   1..17
                         mol_type = other DNA
                         organism = synthetic construct
SEQUENCE: 19
gagtccgagc agaagaa                                                    17

SEQ ID NO: 20            moltype =    length =
SEQUENCE: 20
000

SEQ ID NO: 21            moltype = DNA   length = 12
FEATURE                  Location/Qualifiers
source                   1..12
                         mol_type = other DNA
                         organism = synthetic construct
SEQUENCE: 21
gctcaatgac gt                                                         12

SEQ ID NO: 22            moltype = DNA   length = 23
FEATURE                  Location/Qualifiers
source                   1..23
                         mol_type = other DNA
                         organism = synthetic construct
SEQUENCE: 22
gagtccgagc agaagaagaa ggg                                             23

SEQ ID NO: 23            moltype = DNA   length = 23
FEATURE                  Location/Qualifiers
source                   1..23
                         mol_type = other DNA
                         organism = synthetic construct
SEQUENCE: 23
gagtccgagc agaagaagaa ngg                                             23

SEQ ID NO: 24            moltype = DNA   length = 23
FEATURE                  Location/Qualifiers
source                   1..23
```

-continued

```
                             mol_type = other DNA
                             organism = synthetic construct
SEQUENCE: 24
ggaagccctt ctgcagcacc aga                                           23

SEQ ID NO: 25               moltype = DNA   length = 23
FEATURE                     Location/Qualifiers
source                      1..23
                             mol_type = other DNA
                             organism = synthetic construct
SEQUENCE: 25
ggaatccctt ctgcagcata gtg                                           23

SEQ ID NO: 26               moltype = DNA   length = 23
FEATURE                     Location/Qualifiers
source                      1..23
                             mol_type = other DNA
                             organism = synthetic construct
SEQUENCE: 26
ggaaacccct ctgcagcacc agc                                           23

SEQ ID NO: 27               moltype = DNA   length = 18
FEATURE                     Location/Qualifiers
source                      1..18
                             mol_type = other DNA
                             organism = synthetic construct
SEQUENCE: 27
ggaagccctt ctaccaga                                                 18

SEQ ID NO: 28               moltype = DNA   length = 25
FEATURE                     Location/Qualifiers
source                      1..25
                             mol_type = other DNA
                             organism = synthetic construct
SEQUENCE: 28
ggaagccctt ctgtagcaca ccaga                                         25

SEQ ID NO: 29               moltype = DNA   length = 24
FEATURE                     Location/Qualifiers
source                      1..24
                             mol_type = other DNA
                             organism = synthetic construct
SEQUENCE: 29
ggaagccctt ctgtagccac caga                                          24

SEQ ID NO: 30               moltype = DNA   length = 27
FEATURE                     Location/Qualifiers
source                      1..27
                             mol_type = other DNA
                             organism = synthetic construct
SEQUENCE: 30
ggaatccctt ctgcagccag catagtg                                       27

SEQ ID NO: 31               moltype = DNA   length = 25
FEATURE                     Location/Qualifiers
source                      1..25
                             mol_type = other DNA
                             organism = synthetic construct
SEQUENCE: 31
ggaatccctt ctgcagcgca tagtg                                         25

SEQ ID NO: 32               moltype = DNA   length = 20
FEATURE                     Location/Qualifiers
source                      1..20
                             mol_type = other DNA
                             organism = synthetic construct
SEQUENCE: 32
ggaatccctt ctgcatagtg                                               20

SEQ ID NO: 33               moltype = DNA   length = 20
FEATURE                     Location/Qualifiers
source                      1..20
                             mol_type = other DNA
                             organism = synthetic construct
SEQUENCE: 33
ggaaacccct ctgcaccagc                                               20

SEQ ID NO: 34               moltype = DNA   length = 24
FEATURE                     Location/Qualifiers
```

-continued

```
source                  1..24
                        mol_type = other DNA
                        organism = synthetic construct
SEQUENCE: 34
ggaaacccct ctgcagcaac cagc                                         24

SEQ ID NO: 35          moltype = DNA   length = 65
FEATURE                Location/Qualifiers
source                 1..65
                       mol_type = other DNA
                       organism = synthetic construct
SEQUENCE: 35
ggaaacccct ctgcagcagc aatggcaaca acgttgcgca aactattaac tggcgaacta  60
cttaa                                                              65

SEQ ID NO: 36          moltype = DNA   length = 24
FEATURE                Location/Qualifiers
source                 1..24
                       mol_type = other DNA
                       organism = synthetic construct
SEQUENCE: 36
ggaaacccct ctgcagccac cagc                                         24

SEQ ID NO: 37          moltype = DNA   length = 22
FEATURE                Location/Qualifiers
source                 1..22
                       mol_type = other DNA
                       organism = synthetic construct
SEQUENCE: 37
ggaaacccct ctgcagccca gc                                           22

SEQ ID NO: 38          moltype = DNA   length = 25
FEATURE                Location/Qualifiers
source                 1..25
                       mol_type = other DNA
                       organism = synthetic construct
SEQUENCE: 38
ggaaacccct ctgcagcgca ccagc                                        25

SEQ ID NO: 39          moltype = DNA   length = 63
FEATURE                Location/Qualifiers
source                 1..63
                       mol_type = other DNA
                       organism = synthetic construct
SEQUENCE: 39
ggaaacccct ctgcagcggt gaaagaaaga atcgtcaact ttggccatct cattgctacc  60
agc                                                                63

SEQ ID NO: 40          moltype = DNA   length = 23
FEATURE                Location/Qualifiers
source                 1..23
                       mol_type = other DNA
                       organism = synthetic construct
SEQUENCE: 40
gaggccgagc agaagaaaga cgg                                          23

SEQ ID NO: 41          moltype = DNA   length = 23
FEATURE                Location/Qualifiers
source                 1..23
                       mol_type = other DNA
                       organism = synthetic construct
SEQUENCE: 41
aagtccgagg agaggaagaa agg                                          23

SEQ ID NO: 42          moltype = DNA   length = 23
FEATURE                Location/Qualifiers
source                 1..23
                       mol_type = other DNA
                       organism = synthetic construct
SEQUENCE: 42
gtcatcttag tcattacctg agg                                          23

SEQ ID NO: 43          moltype = DNA   length = 23
FEATURE                Location/Qualifiers
source                 1..23
                       mol_type = other DNA
                       organism = synthetic construct
SEQUENCE: 43
ggaatccctt ctgcagcacc tgg                                          23
```

-continued

```
SEQ ID NO: 44           moltype = DNA   length = 22
FEATURE                 Location/Qualifiers
source                  1..22
                        mol_type = other DNA
                        organism = synthetic construct
SEQUENCE: 44
ttgccccaca gggcagtaac gg                                              22

SEQ ID NO: 45           moltype = DNA   length = 23
FEATURE                 Location/Qualifiers
source                  1..23
                        mol_type = other DNA
                        organism = synthetic construct
SEQUENCE: 45
gaacacaaag catagactgc ggg                                             23

SEQ ID NO: 46           moltype = DNA   length = 23
FEATURE                 Location/Qualifiers
source                  1..23
                        mol_type = other DNA
                        organism = synthetic construct
SEQUENCE: 46
ggcccagact gagcacgtga tgg                                             23

SEQ ID NO: 47           moltype = DNA   length = 23
FEATURE                 Location/Qualifiers
source                  1..23
                        mol_type = other DNA
                        organism = synthetic construct
SEQUENCE: 47
ggcactgcgg ctggaggtgg ggg                                             23

SEQ ID NO: 48           moltype = DNA   length = 23
FEATURE                 Location/Qualifiers
source                  1..23
                        mol_type = other DNA
                        organism = synthetic construct
SEQUENCE: 48
ggctaaagac catagactgt ggg                                             23

SEQ ID NO: 49           moltype = DNA   length = 23
FEATURE                 Location/Qualifiers
source                  1..23
                        mol_type = other DNA
                        organism = synthetic construct
SEQUENCE: 49
gggaataaat catagaatcc tgg                                             23

SEQ ID NO: 50           moltype = DNA   length = 23
FEATURE                 Location/Qualifiers
source                  1..23
                        mol_type = other DNA
                        organism = synthetic construct
SEQUENCE: 50
acacacacac ttagaatctg tgg                                             23

SEQ ID NO: 51           moltype = DNA   length = 23
FEATURE                 Location/Qualifiers
source                  1..23
                        mol_type = other DNA
                        organism = synthetic construct
SEQUENCE: 51
ggtgagtgag tgtgtgcgtg tgg                                             23

SEQ ID NO: 52           moltype = DNA   length = 23
FEATURE                 Location/Qualifiers
source                  1..23
                        mol_type = other DNA
                        organism = synthetic construct
SEQUENCE: 52
gtacaggagc aggagaagaa tgg                                             23

SEQ ID NO: 53           moltype = DNA   length = 23
FEATURE                 Location/Qualifiers
source                  1..23
                        mol_type = other DNA
                        organism = synthetic construct
SEQUENCE: 53
```

-continued

```
caaacggagc agaagaagaa agg                                            23

SEQ ID NO: 54            moltype = DNA   length = 23
FEATURE                  Location/Qualifiers
source                   1..23
                         mol_type = other DNA
                         organism = synthetic construct
SEQUENCE: 54
gagcacgagc aagagaagaa ggg                                            23

SEQ ID NO: 55            moltype = DNA   length = 23
FEATURE                  Location/Qualifiers
source                   1..23
                         mol_type = other DNA
                         organism = synthetic construct
SEQUENCE: 55
gagtacaagc agatgaaaaa cgg                                            23

SEQ ID NO: 56            moltype = DNA   length = 23
FEATURE                  Location/Qualifiers
source                   1..23
                         mol_type = other DNA
                         organism = synthetic construct
SEQUENCE: 56
gagttagagc agaggaagag agg                                            23

SEQ ID NO: 57            moltype = DNA   length = 23
FEATURE                  Location/Qualifiers
source                   1..23
                         mol_type = other DNA
                         organism = synthetic construct
SEQUENCE: 57
aagtccgggc aaaagaggaa agg                                            23

SEQ ID NO: 58            moltype = DNA   length = 23
FEATURE                  Location/Qualifiers
source                   1..23
                         mol_type = other DNA
                         organism = synthetic construct
SEQUENCE: 58
gagtccaagc agtagaggaa ggg                                            23

SEQ ID NO: 59            moltype = DNA   length = 24
FEATURE                  Location/Qualifiers
source                   1..24
                         mol_type = other DNA
                         organism = synthetic construct
SEQUENCE: 59
cagtagtgag cagaagaaga tagg                                           24

SEQ ID NO: 60            moltype = DNA   length = 23
FEATURE                  Location/Qualifiers
source                   1..23
                         mol_type = other DNA
                         organism = synthetic construct
SEQUENCE: 60
gagttagagc agaagaagaa agg                                            23

SEQ ID NO: 61            moltype = DNA   length = 23
FEATURE                  Location/Qualifiers
source                   1..23
                         mol_type = other DNA
                         organism = synthetic construct
SEQUENCE: 61
gtccaagagc aggagaagaa ggg                                            23

SEQ ID NO: 62            moltype = DNA   length = 23
FEATURE                  Location/Qualifiers
source                   1..23
                         mol_type = other DNA
                         organism = synthetic construct
SEQUENCE: 62
aagtccatgc agaagaggaa ggg                                            23

SEQ ID NO: 63            moltype = DNA   length = 23
FEATURE                  Location/Qualifiers
source                   1..23
                         mol_type = other DNA
                         organism = synthetic construct
```

-continued

```
SEQUENCE: 63
ggagtagagc agaggaagaa ggg                                              23

SEQ ID NO: 64              moltype = DNA   length = 23
FEATURE                    Location/Qualifiers
source                     1..23
                           mol_type = other DNA
                           organism = synthetic construct
SEQUENCE: 64
ggaactgagc aaaagaagat agg                                              23

SEQ ID NO: 65              moltype = DNA   length = 23
FEATURE                    Location/Qualifiers
source                     1..23
                           mol_type = other DNA
                           organism = synthetic construct
SEQUENCE: 65
gaatccaagc agaagaagag aag                                              23

SEQ ID NO: 66              moltype = DNA   length = 23
FEATURE                    Location/Qualifiers
source                     1..23
                           mol_type = other DNA
                           organism = synthetic construct
SEQUENCE: 66
gcgacagagc agaagaagaa ggg                                              23

SEQ ID NO: 67              moltype = DNA   length = 23
FEATURE                    Location/Qualifiers
source                     1..23
                           mol_type = other DNA
                           organism = synthetic construct
SEQUENCE: 67
gaagtagagc agaagaagaa gcg                                              23

SEQ ID NO: 68              moltype = DNA   length = 23
FEATURE                    Location/Qualifiers
source                     1..23
                           mol_type = other DNA
                           organism = synthetic construct
SEQUENCE: 68
gagtctaagc aggagaataa agg                                              23

SEQ ID NO: 69              moltype = DNA   length = 23
FEATURE                    Location/Qualifiers
source                     1..23
                           mol_type = other DNA
                           organism = synthetic construct
SEQUENCE: 69
tgtccagagc agatgaagaa tgg                                              23

SEQ ID NO: 70              moltype = DNA   length = 23
FEATURE                    Location/Qualifiers
source                     1..23
                           mol_type = other DNA
                           organism = synthetic construct
SEQUENCE: 70
gaacatgagc agaagaagag gag                                              23

SEQ ID NO: 71              moltype = DNA   length = 23
FEATURE                    Location/Qualifiers
source                     1..23
                           mol_type = other DNA
                           organism = synthetic construct
SEQUENCE: 71
aggccagagc aaaagaagag agg                                              23

SEQ ID NO: 72              moltype = DNA   length = 23
FEATURE                    Location/Qualifiers
source                     1..23
                           mol_type = other DNA
                           organism = synthetic construct
SEQUENCE: 72
gtacaagagc aggagaagaa ggg                                              23

SEQ ID NO: 73              moltype = DNA   length = 23
FEATURE                    Location/Qualifiers
source                     1..23
                           mol_type = other DNA
```

-continued

```
                            organism = synthetic construct
SEQUENCE: 73
gagtcagggc agaagaagaa aat                                              23

SEQ ID NO: 74          moltype = DNA   length = 23
FEATURE                Location/Qualifiers
source                 1..23
                       mol_type = other DNA
                       organism = synthetic construct
SEQUENCE: 74
gagtaagaga agaagaagaa ggg                                              23

SEQ ID NO: 75          moltype = DNA   length = 23
FEATURE                Location/Qualifiers
source                 1..23
                       mol_type = other DNA
                       organism = synthetic construct
SEQUENCE: 75
aagcccgagc agaagaagtt gag                                              23

SEQ ID NO: 76          moltype = DNA   length = 23
FEATURE                Location/Qualifiers
source                 1..23
                       mol_type = other DNA
                       organism = synthetic construct
SEQUENCE: 76
gagtcctagc aggagaagaa gag                                              23

SEQ ID NO: 77          moltype = DNA   length = 22
FEATURE                Location/Qualifiers
source                 1..22
                       mol_type = other DNA
                       organism = synthetic construct
SEQUENCE: 77
gaggggagca aaagaaggag gg                                               22

SEQ ID NO: 78          moltype = DNA   length = 23
FEATURE                Location/Qualifiers
source                 1..23
                       mol_type = other DNA
                       organism = synthetic construct
SEQUENCE: 78
gagtcagagc aaaagaagta gtg                                              23

SEQ ID NO: 79          moltype = DNA   length = 23
FEATURE                Location/Qualifiers
source                 1..23
                       mol_type = other DNA
                       organism = synthetic construct
SEQUENCE: 79
gagtcagagc aaaagaagta gtg                                              23

SEQ ID NO: 80          moltype = DNA   length = 23
FEATURE                Location/Qualifiers
source                 1..23
                       mol_type = other DNA
                       organism = synthetic construct
SEQUENCE: 80
gagtctaagc agaagaagaa gag                                              23

SEQ ID NO: 81          moltype = DNA   length = 21
FEATURE                Location/Qualifiers
source                 1..21
                       mol_type = other DNA
                       organism = synthetic construct
SEQUENCE: 81
cagggagaag aagaagaagg g                                                21

SEQ ID NO: 82          moltype = DNA   length = 23
FEATURE                Location/Qualifiers
source                 1..23
                       mol_type = other DNA
                       organism = synthetic construct
SEQUENCE: 82
gagttagaga agaagaagac tgg                                              23

SEQ ID NO: 83          moltype = DNA   length = 23
FEATURE                Location/Qualifiers
source                 1..23
```

-continued

```
                          mol_type = other DNA
                          organism = synthetic construct
SEQUENCE: 83
acaatcgagc agcagaagaa tgg                                        23

SEQ ID NO: 84            moltype = DNA   length = 23
FEATURE                  Location/Qualifiers
source                   1..23
                          mol_type = other DNA
                          organism = synthetic construct
SEQUENCE: 84
gagtaggagc agatgaagag agg                                        23

SEQ ID NO: 85            moltype = DNA   length = 23
FEATURE                  Location/Qualifiers
source                   1..23
                          mol_type = other DNA
                          organism = synthetic construct
SEQUENCE: 85
cagtatgagc aaaagaagaa aga                                        23

SEQ ID NO: 86            moltype = DNA   length = 23
FEATURE                  Location/Qualifiers
source                   1..23
                          mol_type = other DNA
                          organism = synthetic construct
SEQUENCE: 86
gagtccatac agaggaagaa aag                                        23

SEQ ID NO: 87            moltype = DNA   length = 21
FEATURE                  Location/Qualifiers
source                   1..21
                          mol_type = other DNA
                          organism = synthetic construct
SEQUENCE: 87
gaatgagcaa aagaagaaag c                                          21

SEQ ID NO: 88            moltype = DNA   length = 23
FEATURE                  Location/Qualifiers
source                   1..23
                          mol_type = other DNA
                          organism = synthetic construct
SEQUENCE: 88
aatacagagc agaagaagaa tgg                                        23

SEQ ID NO: 89            moltype = DNA   length = 23
FEATURE                  Location/Qualifiers
source                   1..23
                          mol_type = other DNA
                          organism = synthetic construct
SEQUENCE: 89
aatacagagc agaagaagaa tgg                                        23

SEQ ID NO: 90            moltype = DNA   length = 21
FEATURE                  Location/Qualifiers
source                   1..21
                          mol_type = other DNA
                          organism = synthetic construct
SEQUENCE: 90
tagtgagcag aagaagagag a                                          21

SEQ ID NO: 91            moltype = DNA   length = 23
FEATURE                  Location/Qualifiers
source                   1..23
                          mol_type = other DNA
                          organism = synthetic construct
SEQUENCE: 91
ttctccaagc agaagaagaa gag                                        23

SEQ ID NO: 92            moltype = DNA   length = 23
FEATURE                  Location/Qualifiers
source                   1..23
                          mol_type = other DNA
                          organism = synthetic construct
SEQUENCE: 92
gagtccatac aggagaagaa aga                                        23

SEQ ID NO: 93            moltype = DNA   length = 23
FEATURE                  Location/Qualifiers
```

-continued

```
source                  1..23
                        mol_type = other DNA
                        organism = synthetic construct
SEQUENCE: 93
aggtgggagc agaagaagaa ggg                                         23

SEQ ID NO: 94           moltype = DNA   length = 23
FEATURE                 Location/Qualifiers
source                  1..23
                        mol_type = other DNA
                        organism = synthetic construct
SEQUENCE: 94
aaggcagagc agaggaagag agg                                         23

SEQ ID NO: 95           moltype = DNA   length = 24
FEATURE                 Location/Qualifiers
source                  1..24
                        mol_type = other DNA
                        organism = synthetic construct
SEQUENCE: 95
gaggcacaag caaaagaaga aaag                                        24

SEQ ID NO: 96           moltype = DNA   length = 23
FEATURE                 Location/Qualifiers
source                  1..23
                        mol_type = other DNA
                        organism = synthetic construct
SEQUENCE: 96
gaagtagagc agaagaagaa gcg                                         23

SEQ ID NO: 97           moltype = DNA   length = 16
FEATURE                 Location/Qualifiers
source                  1..16
                        mol_type = other DNA
                        organism = synthetic construct
SEQUENCE: 97
ctatcttaag gtagtc                                                 16

SEQ ID NO: 98           moltype = DNA   length = 16
FEATURE                 Location/Qualifiers
source                  1..16
                        mol_type = other DNA
                        organism = synthetic construct
SEQUENCE: 98
actctcttaa ggtagc                                                 16

SEQ ID NO: 99           moltype = DNA   length = 16
FEATURE                 Location/Qualifiers
source                  1..16
                        mol_type = other DNA
                        organism = synthetic construct
SEQUENCE: 99
ctatcttaag gtagcc                                                 16

SEQ ID NO: 100          moltype = DNA   length = 15
FEATURE                 Location/Qualifiers
source                  1..15
                        mol_type = other DNA
                        organism = synthetic construct
SEQUENCE: 100
ctaccttaag gtagt                                                  15

SEQ ID NO: 101          moltype = DNA   length = 15
FEATURE                 Location/Qualifiers
source                  1..15
                        mol_type = other DNA
                        organism = synthetic construct
SEQUENCE: 101
ctaccttaag ggagc                                                  15

SEQ ID NO: 102          moltype = DNA   length = 15
FEATURE                 Location/Qualifiers
source                  1..15
                        mol_type = other DNA
                        organism = synthetic construct
SEQUENCE: 102
ctatcttaag ggagc                                                  15

SEQ ID NO: 103          moltype = DNA   length = 15
```

-continued

```
FEATURE              Location/Qualifiers
source               1..15
                     mol_type = other DNA
                     organism = synthetic construct
SEQUENCE: 103
ctcccttaag ggagc                                                    15

SEQ ID NO: 104       moltype = DNA   length = 16
FEATURE              Location/Qualifiers
source               1..16
                     mol_type = other DNA
                     organism = synthetic construct
SEQUENCE: 104
ctatcttaag gtaggc                                                   16

SEQ ID NO: 105       moltype = DNA   length = 16
FEATURE              Location/Qualifiers
source               1..16
                     mol_type = other DNA
                     organism = synthetic construct
SEQUENCE: 105
ctctcttaag ggagcc                                                   16

SEQ ID NO: 106       moltype = DNA   length = 16
FEATURE              Location/Qualifiers
source               1..16
                     mol_type = other DNA
                     organism = synthetic construct
SEQUENCE: 106
ctctcttaag gtagct                                                   16

SEQ ID NO: 107       moltype = DNA   length = 15
FEATURE              Location/Qualifiers
source               1..15
                     mol_type = other DNA
                     organism = synthetic construct
SEQUENCE: 107
ctcccttaag gtagt                                                    15

SEQ ID NO: 108       moltype = DNA   length = 16
FEATURE              Location/Qualifiers
source               1..16
                     mol_type = other DNA
                     organism = synthetic construct
SEQUENCE: 108
ctctcttaag gtagtc                                                   16

SEQ ID NO: 109       moltype = DNA   length = 16
FEATURE              Location/Qualifiers
source               1..16
                     mol_type = other DNA
                     organism = synthetic construct
SEQUENCE: 109
ctctcttaag atagcc                                                   16

SEQ ID NO: 110       moltype = DNA   length = 15
FEATURE              Location/Qualifiers
source               1..15
                     mol_type = other DNA
                     organism = synthetic construct
SEQUENCE: 110
ctaccttaag gtagc                                                    15

SEQ ID NO: 111       moltype = DNA   length = 16
FEATURE              Location/Qualifiers
source               1..16
                     mol_type = other DNA
                     organism = synthetic construct
SEQUENCE: 111
ctcccttaag gtagtc                                                   16

SEQ ID NO: 112       moltype = DNA   length = 16
FEATURE              Location/Qualifiers
source               1..16
                     mol_type = other DNA
                     organism = synthetic construct
SEQUENCE: 112
ctctcataag gtagtc                                                   16
```

-continued

```
SEQ ID NO: 113          moltype = DNA   length = 16
FEATURE                 Location/Qualifiers
source                  1..16
                        mol_type = other DNA
                        organism = synthetic construct
SEQUENCE: 113
ctctcataag gtagcc                                                   16

SEQ ID NO: 114          moltype = DNA   length = 16
FEATURE                 Location/Qualifiers
source                  1..16
                        mol_type = other DNA
                        organism = synthetic construct
SEQUENCE: 114
ctctgttaag gtagtc                                                   16

SEQ ID NO: 115          moltype = DNA   length = 15
FEATURE                 Location/Qualifiers
source                  1..15
                        mol_type = other DNA
                        organism = synthetic construct
SEQUENCE: 115
ctcccttaag agagc                                                    15

SEQ ID NO: 116          moltype = DNA   length = 16
FEATURE                 Location/Qualifiers
source                  1..16
                        mol_type = other DNA
                        organism = synthetic construct
SEQUENCE: 116
ctcccttaag gtagcc                                                   16

SEQ ID NO: 117          moltype = DNA   length = 16
FEATURE                 Location/Qualifiers
source                  1..16
                        mol_type = other DNA
                        organism = synthetic construct
SEQUENCE: 117
ctcccttaag gtagac                                                   16

SEQ ID NO: 118          moltype = DNA   length = 15
FEATURE                 Location/Qualifiers
source                  1..15
                        mol_type = other DNA
                        organism = synthetic construct
SEQUENCE: 118
ctctcttaag gtagt                                                    15

SEQ ID NO: 119          moltype = DNA   length = 15
FEATURE                 Location/Qualifiers
source                  1..15
                        mol_type = other DNA
                        organism = synthetic construct
SEQUENCE: 119
ctatcttaag gtagt                                                    15

SEQ ID NO: 120          moltype = DNA   length = 15
FEATURE                 Location/Qualifiers
source                  1..15
                        mol_type = other DNA
                        organism = synthetic construct
SEQUENCE: 120
ctctcttaag ggagc                                                    15

SEQ ID NO: 121          moltype = DNA   length = 15
FEATURE                 Location/Qualifiers
source                  1..15
                        mol_type = other DNA
                        organism = synthetic construct
SEQUENCE: 121
ctatcttaag ggagt                                                    15

SEQ ID NO: 122          moltype = DNA   length = 16
FEATURE                 Location/Qualifiers
source                  1..16
                        mol_type = other DNA
                        organism = synthetic construct
SEQUENCE: 122
ctctgttaag gtagcc                                                   16
```

-continued

```
SEQ ID NO: 123           moltype = DNA  length = 16
FEATURE                  Location/Qualifiers
source                   1..16
                         mol_type = other DNA
                         organism = synthetic construct
SEQUENCE: 123
ctctcttaag gtaggc                                                16

SEQ ID NO: 124           moltype = DNA  length = 15
FEATURE                  Location/Qualifiers
source                   1..15
                         mol_type = other DNA
                         organism = synthetic construct
SEQUENCE: 124
ctctcttaag gtagc                                                 15

SEQ ID NO: 125           moltype = DNA  length = 15
FEATURE                  Location/Qualifiers
source                   1..15
                         mol_type = other DNA
                         organism = synthetic construct
SEQUENCE: 125
ctatcttaag gtagc                                                 15

SEQ ID NO: 126           moltype = DNA  length = 15
FEATURE                  Location/Qualifiers
source                   1..15
                         mol_type = other DNA
                         organism = synthetic construct
SEQUENCE: 126
ctctcttaag agagc                                                 15

SEQ ID NO: 127           moltype = DNA  length = 153
FEATURE                  Location/Qualifiers
misc_feature             43..44
                         note = positions 43 and 44 are non-consecutive residues
                          separated by a barcode
misc_feature             71..72
                         note = positions 71 and 72 are non-consecutive residues
                          separated by a potential off target site
misc_feature             127..128
                         note = positions 127 and 128 are non-consecutive residues
                          separated by a barcode
source                   1..153
                         mol_type = other DNA
                         organism = synthetic construct
SEQUENCE: 127
gacgttctca cagcaattcg tacagtcgac gtcgattcgt gcttttgaca ttctgcaatt   60
gcacacagcg ttgcagactg taagtatgta tgcttcgcgc agtgcgactt cgcagcgcat  120
cacttcaagt agctgcgagt cttacagcat tgc                              153

SEQ ID NO: 128           moltype = DNA  length = 41
FEATURE                  Location/Qualifiers
misc_feature             21..22
                         note = positions 21 and 22 are non-consecutive residues
                          separated by a barcode, flanking genomic context,
                          potential_off_target_site, flanking_genomic_context,
                          barcode
source                   1..41
                         mol_type = other DNA
                         organism = synthetic construct
SEQUENCE: 128
gacgttctca cagcaattcg ttgcgagtct tacagcattg c                     41

SEQ ID NO: 129           moltype = DNA  length = 133
FEATURE                  Location/Qualifiers
misc_feature             43..44
                         note = positions 43 and 44 are non-consecutive residues
                          separated by a barcode
misc_feature             61..62
                         note = positions 61 and 62 are non-consecutive residues
                          separated by a flanking_genomic_context,
                          potential_off_target_sitei, and a flanking_genomic_context
misc_feature             106..107
                         note = positiions 106 and 107 are non-consecutive residues
                          separated by a barcode
source                   1..133
                         mol_type = other DNA
```

-continued

```
                       organism = synthetic construct
SEQUENCE: 129
gacgttctca cagcaattcg tacagtcgac gtcgattcgt gcttttgaca ttctgcaatg   60
taagtatgta tgcttcgcgc agtgcgactt cgcagcgcat cacttcaagt agctgcgagt   120
cttacagcat tgc                                                      133

SEQ ID NO: 130         moltype = DNA   length = 60
FEATURE                Location/Qualifiers
source                 1..60
                       mol_type = other DNA
                       organism = synthetic construct
SEQUENCE: 130
gctgactaga cactgctatc acactctctc annnnnnnna gacgttctca cagcaattcg   60

SEQ ID NO: 131         moltype = DNA   length = 60
FEATURE                Location/Qualifiers
source                 1..60
                       mol_type = other DNA
                       organism = synthetic construct
SEQUENCE: 131
gcgtaatcac tgatgcttcg taaatgagac annnnnnnnt gcaatgctgt aagactcgca   60
```

HIGHLY SENSITIVE IN VITRO ASSAYS TO DEFINE SUBSTRATE PREFERENCES AND SITES OF NUCLEIC-ACID BINDING, MODIFYING, AND CLEAVING AGENTS

CLAIM OF PRIORITY

This application is a continuation of U.S. patent application Ser. No. 16/852,257, filed Apr. 17, 2020, which is a continuation of U.S. patent application Ser. No. 16/386,472, filed on Apr. 17, 2019, which claims the benefit of U.S. Provisional Patent Application Ser. Nos. 62/767,633, filed on Nov. 15, 2018; and 62/659,073, filed on Apr. 17, 2018. The entire contents of the foregoing are hereby incorporated by reference.

FEDERALLY SPONSORED RESEARCH OR DEVELOPMENT

This invention was made with Government support under Grant No. HR0011-17-2-0042 awarded by the Defense Advanced Research Projects Agency (DARPA)) and HG009490 and GM118158 awarded by National Institutes of Health. The Government has. The Government has certain rights in the invention.

SEQUENCE LISTING

This application contains a Sequence Listing that has been submitted electronically as an XML file named "40978-0038004_SL_ST26.XML." The XML file, created on Nov. 4, 2023, is 119,417 bytes in size. The material in the XML file is hereby incorporated by reference in its entirety.

TECHNICAL FIELD

Provided herein are methods and compositions for performing highly sensitive in vitro assays to define substrate preferences and off-target sites of nucleic-acid binding, modifying, and cleaving agents.

BACKGROUND

Off-target activity is a major challenge for the safe or effective use of proteins with customizable DNA-binding activities (including but not limited to homing endonucleases, zinc fingers, transcriptional activator-like effectors (TALEs), and CRISPR-Cas9 system proteins) in clinical, industrial, and research settings.

SUMMARY

Provided herein are methods and compositions for performing highly sensitive in vitro assays to define substrate preferences and off-target sites of nucleic-acid binding, modifying, and cleaving agents.

Provided herein are methods for identifying double stranded DNA sequences that are cleaved, modified, or bound by an enzyme. The methods include (i) providing a plurality of linear dsDNA oligonucleotides of known sequences, each oligonucleotide having a 5' end and a 3' end and bearing at least two copies of a unique identifier sequence at or near both the 3' and 5' ends of the oligonucleotide, and common sequences that are present at the 5' and 3' ends in each one of the oligonucleotides in the plurality; (ii) incubating the plurality in the presence of an enzyme selected from site-specific nucleases, DNA modifying proteins, and DNA binding domains, under conditions sufficient for cleavage, modification, or binding to occur; (iii) selecting, and optionally enriching for, oligonucleotides that are cleaved, modified, or bound; and (iv) determining the sequences of the selected oligonucleotides that are cleaved, modified, or bound, thereby identifying double stranded DNA sequences that are cleaved, modified, or bound by an enzyme. Also provided herein are methods for identifying double stranded DNA sequences that are cleaved, modified, or bound by an enzyme. The methods include (i) providing an initial plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality in the presence of an enzyme selected from site-specific nucleases, modifying proteins, and DNA binding domains, under conditions sufficient for cleavage, modification, or binding to occur; (iii) selecting oligonucleotides that are not cleaved, modified, or bound; and (iv) determining the sequences of the selected oligonucleotides that are not cleaved, modified, or bound; and (v) comparing the sequences of the selected oligonucleotides that are not cleaved, modified, or bound to the sequences of the initial plurality of pre-enriched linear dsDNA oligonucleotides of known sequences; wherein the linear dsDNA oligonucleotides in the initial plurality that were not selected are identified as being cleaved, modified, or bound by the enzyme. Further, provided herein are methods for identifying double stranded DNA sequences that are modified by a base editing enzyme (e.g., a cytidine deaminase that converts deoxycytidine to deoxyuridine or an adenine base editing enzyme that converts deoxyadenine to deoxyinosine). The methods include (i) providing a plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality linear dsDNA oligonucleotides in the presence of a base editing enzyme under conditions sufficient for modification to occur; (iii) amplifying the oligonucleotides with a polymerase that converts edited base pairs to equal mixtures of canonical base pairs (such as a uracil tolerant polymerase that converts dU:dG base pairs to equal mixtures of dT:dA and dC:dG base pairs, or dI:dT base pairs to equal mixtures of dA:dT and dG:dC base pairs) during DNA synthesis (i.e., wherein a dATP nucleotide is incorporated across from dU or a dCTP nucleotide is incorporated across from dI), such that an oligonucleotide that has been modified by the base editing enzyme will be amplified as a mixture of the original barcode-linked sequence from the pre-treatment library and also a modified sequence that contains substitutions (for example dC→dT or dA→dG); and (iv) determining the sequences of the amplified oligonucleotides, thereby identifying double stranded DNA sequences that are modified by the base editing enzyme.

Additionally, provided herein are methods for identifying double stranded DNA sequences that are modified by a cytidine deaminase base editing enzyme that converts cytidine to uridine and generates a nick on the opposite strand. The methods include (i) providing a plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality of linear dsDNA oligonucleotides in the presence of a base editing enzyme under conditions sufficient for modification to occur, and then incubating the plurality of linear dsDNA oligonucleotides in the presence of enzymes to generate a single-strand break (nick) at sites with uridine nucleotides, thereby creating dsDNA oligonucleotides that contain two nicks with 5' phosphates on opposite strands, thereby creating overhangs; (iii) incubating the dsDNA oligonucleotides with a DNA polymerase that creates 5' phosphorylated blunt ends from the overhangs (e.g., T4 DNA polymerase or PHUSION® DNA polymerase (a high-fidelity thermostable polymerase with 5'→3' polymerase activity and 3'→5' exonuclease activity that generates blunt ends) or PHUSION U DNA polymerase (ThermoFisher, a mutant of PHUSION® that incorporates dUTP and reads through uracil present in DNA templates)); (iv) capturing the phosphorylated blunt ends with double stranded DNA adapters comprising primer sequences; (v) amplifying the sequences using one primer specific to the adapter and one primer specific to the common sequence backbone; (vi) optionally performing an additional selection by performing size selection for smaller, cut fragments before or after amplification; and (vii) determining the sequences of the amplified oligonucleotides, thereby identifying double stranded DNA sequences that are modified by the base editing enzyme.

Further, provided herein are methods for identifying double stranded DNA sequences that are modified by an adenine base editing enzyme that converts deoxyadenine to deoxyinosine and generates a nick on the opposite strand. The methods include (i) providing a plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality of linear dsDNA oligonucleotides in the presence of a base editing enzyme under conditions sufficient for modification to occur, and then incubating the plurality of linear dsDNA oligonucleotides in the presence of endonuclease V enzymes to generate a single-strand break (nick) at sites with inosine nucleotides, thereby creating dsDNA oligonucleotides that contain two nicks with 5' phosphates on opposite strands, thereby creating overhangs; (iii) incubating the dsDNA oligonucleotides with a DNA polymerase that creates 5' phosphorylated blunt ends from the overhangs (e.g., T4 DNA polymerase or PHUSION® DNA polymerase (a high-fidelity thermostable polymerase with 5' →3' polymerase activity and 3'→5' exonuclease activity that generates blunt ends) or PHUSION U DNA polymerase (ThermoFisher, a mutant of PHUSION® that incorporates dUTP and reads through uracil present in DNA templates)); (iv) ligating the phosphorylated blunt ends with double stranded DNA adapters comprising primer sequences; (v) amplifying the sequences using one primer specific to the adapter and one primer specific to the common sequence backbone; (vi) optionally performing an additional selection by performing size selection for smaller, cut fragments before or after amplification; and (vii) determining the sequences of the amplified oligonucleotides; thereby identifying double stranded DNA sequences that are modified by the base editing enzyme.

A method of identifying double stranded DNA sequences that are modified by an adenine base editing enzyme that converts deoxyadenine to deoxyinosine and generates a nick on the opposite strand or a cytidine deaminase base editing enzyme that converts cytidine to uridine and generates a nick on the opposite strand, the method comprising: (i) providing a plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality of linear dsDNA oligonucleotides in the presence of Endonuclease MS from *Thermococcus kodakarensis* (TkoEndoMS) to induce double strand breaks (DSBs) at deamination sites in the substrate DNA to produce DNA fragments with single-stranded, 5 base pair overhanging ends centered at the deamination site; (iii) treating the DNA fragments with uracil DNA glycosylase and endonuclease VIII to remove the deoxyuracil base from the ends of the DNA fragments; (iv) end-repairing and/or A-tailing the ends of the DNA fragments; (v) ligating an adapter oligonucleotide (preferably comprising sequences for use in high throughput sequencing) to the end; and (vi) sequencing the DNA fragments. In addition, provided herein are methods for identifying double stranded DNA sequences that are bound by a catalytically-inactive Cas9 in the presence of a selected gRNA or another DNA-binding domain. The methods include (i) providing a plurality of linear dsDNA oligonucleotides of known sequences, each oligonucleotide having a 5' end and a 3' end and bearing two copies of a unique identifier sequence at or near both the 3' and 5' ends of the oligonucleotide, and a common sequence that is present in each one of the oligonucleotides in the plurality; (ii) incubating the plurality in the presence of a DNA binding domain, e.g., Cas9 enzyme complexed with sgRNAs or another DNA-binding domain, that is attached to magnetic beads (e.g., covalently bound or bound by an affinity handle), under conditions sufficient for binding to occur; (iii) selecting, and optionally enriching for, oligonucleotides that are bound through one or more sets of bead pulldown and washing in an appropriate buffer to promote dissociation into supernatant of unbound molecules, followed by elution of bound DNA either in an appropriate buffer to promote dissociation of any bound DNA or in a buffer containing a protease, such as proteinase K, to degrade bead-bound protein and release bound DNA; and (iv) determining the sequences of the selected oligonucleotides that are cleaved, thereby identifying double stranded DNA sequences that are bound by the DNA binding domain.

In some embodiments, the linear dsDNA oligonucleotides used in methods described herein include (i) a set of all potential off-target sequences in a reference genome bearing up to a certain number of mismatches relative to an identified on-target site (analogous to genomic DNA libraries); (ii) a comprehensive set of potential off-target sites bearing up to a certain number of mismatches (analogous to random base substitution libraries); (iii) a library of potential off-target sequences present in a set of variant genomes from defined populations (i.e., genomic DNA libraries designed to reflect DNA sequence variants present in a population of individuals); or (iv) another relevant defined set of potential off-target sites (for example, oncogene hotspots or sequences from tumor suppressor genes).

In some embodiments, the pre-enriched linear DNA library members are first synthesized as individual single-stranded DNA sequences, e.g., on high-density oligonucleotide arrays; and the single-stranded DNA sequences are converted into double-stranded DNA molecules by priming against the common sequence, optionally before or after being released from the chip.

In some embodiments, the pre-enriched linear DNA library members represent 1) a set of all potential off-target sequences in a reference genome bearing up to a certain number of mismatches relative to the on-target site (analogous to genomic DNA libraries), 2) a comprehensive set of potential off-target sites bearing up to a certain number of mismatches (analogous to random base substitution libraries), 3) a library of potential off-target sequences present in a set of variant genomes from defined populations (i.e., genomic DNA libraries designed to reflect DNA sequence variants present in a population of individuals), or 4) other relevant defined sets of potential off-target sites (for example, oncogene hotspots or sequences from tumor suppressor genes).

In some embodiments, the pre-enriched linear DNA library members comprise at least 1,000, 2500, 5000, or 10,000 and up to $10^6$, $10^7$, $10^8$, $10^9$, $10^{10}$, or $10^{11}$ different sequences, e.g., 10-100 k different sequences.

In some embodiments, the pre-enriched linear DNA library members comprise sequences that are 50-500, e.g., 100-400, e.g., 150 to 300 bp long, e.g., 200 to 280 bp long.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1. Illustration of the differences in library complexity among base substitution library (SEQ ID NOs.: 1-6, 1, and 7-11) and genomic DNA libraries (SEQ ID NOs.: 1 and 12-16). For genomic libraries, the on-target site (in a red box in this example) retains very little similarity to the other roughly ~3 billion genomic sequences. For base substitution libraries, the pre-selection libraries are enriched for sites that are not necessarily present in the genome but that are similar to the intended target site. Substitutions are indicated by lower case letters.

FIG. 5. Identification of on-target sequences through screening of random base substitution library and of genomic DNA library. Substrates with fewer numbers of mutations (indicated by lower m numbers, where (m_d_i) →m=number of mutations, i=number of insertions, d=number of deletions) in the substrate profiling library and in the genome-inspired library where Xm0 denotes m mismatches without any insertions, RNAmd indicates a target site deletion of length d with m mismatches at the remaining base pairs in the site, DNAmi indicates a target site insertion of length I with m mismatches at the remaining base pairs in the site).

FIG. 6. Compositions of representative genomic DNA oligonucleotide libraries are shown. The number of individual genomic sites are listed according to number of mismatches and bulges. Unless otherwise specified, these libraries were utilized in the experiments outlined in the subsequent figures.

FIG. 7. Library characterization. Uniformity metrics and drop out percentages are shown for each of the libraries, after oligonucleotide synthesis, library amplification, and Illumina sequencing. $90^{th}$ percentile sequencing counts refer to the number of sequencing reads obtained for the library member in the $90^{th}$ percentile, when ordered in terms of increasing reads. 90/10 ratio is the ratio of the number of sequencing reads for the $90^{th}$ percentile library member divided by the $10^{th}$ percentile library member and is a metric of library uniformity. Drop out refers to the number of sequences that were not represented in the sequenced, amplified libraries.

FIG. 10. Enrichment of moderately enriched CIRCLE-seq sites. Swarm plots are shown for representative cleavage selections using the ONE-seq method. Each circle represents the aggregate read counts, normalized to the on-target sequence for a given guide RNA selection (listed on top), for an individual library member. The black stars indicate the on-target library member. Filled circles denote sites with 10-99 read counts that were identified by published CIRCLE-seq experiments.

FIG. 11. Enrichment of lowly enriched CIRCLE-seq sites. Swarm plots are shown for representative cleavage selections using the ONE-seq method. Each circle represents the aggregate read counts, normalized to the on-target sequence for a given guide RNA selection (listed on top), for an individual library member. The black stars indicate the on-target library member. Filled circles denote sites with 1-9 read counts that were identified by published CIRCLE-seq experiments.

FIG. 13. Validation results of three FANCF off-target sites identified by ONE-seq but not GUIDE-seq or CIRCLE-seq. Targeted amplicon sequencing was performed on three of the five most highly enriched novel off-target candidates identified by ONE-seq from HEK293T cells sorted for the the top decile of expression of a SpCas9:FANCF sgRNA construct. On the left, total number of indel-containing (edited) sequence reads and total number of reference reads are shown, along with edit percentage and unedited candidate off-target sequence are shown. To the right, individual data from three separate sorting and control (untreated) experiments are shown. (SEQ ID NOs:24-39 appear in order)

FIG. 20. Newly identified and validated BE3 off-target sites. Data from targeted amplicon sequencing from genomic DNA from HEK293T cells expressing the indicated BE3:sgRNA complexes are shown, in comparison to an untreated control. Experiments were performed in three replicates. Only the 28 newly identified and validated BE3 off-target sites compared to Digenome-seq are shown.

FIG. 24. Validated ABE off-target sites. Data from targeted amplicon sequencing from genomic DNA from HEK293T cells expressing the indicated ABEmax:sgRNA complexes are shown, in comparison to an untreated control. Experiments were performed in three replicates.

DETAILED DESCRIPTION

Figure 2:
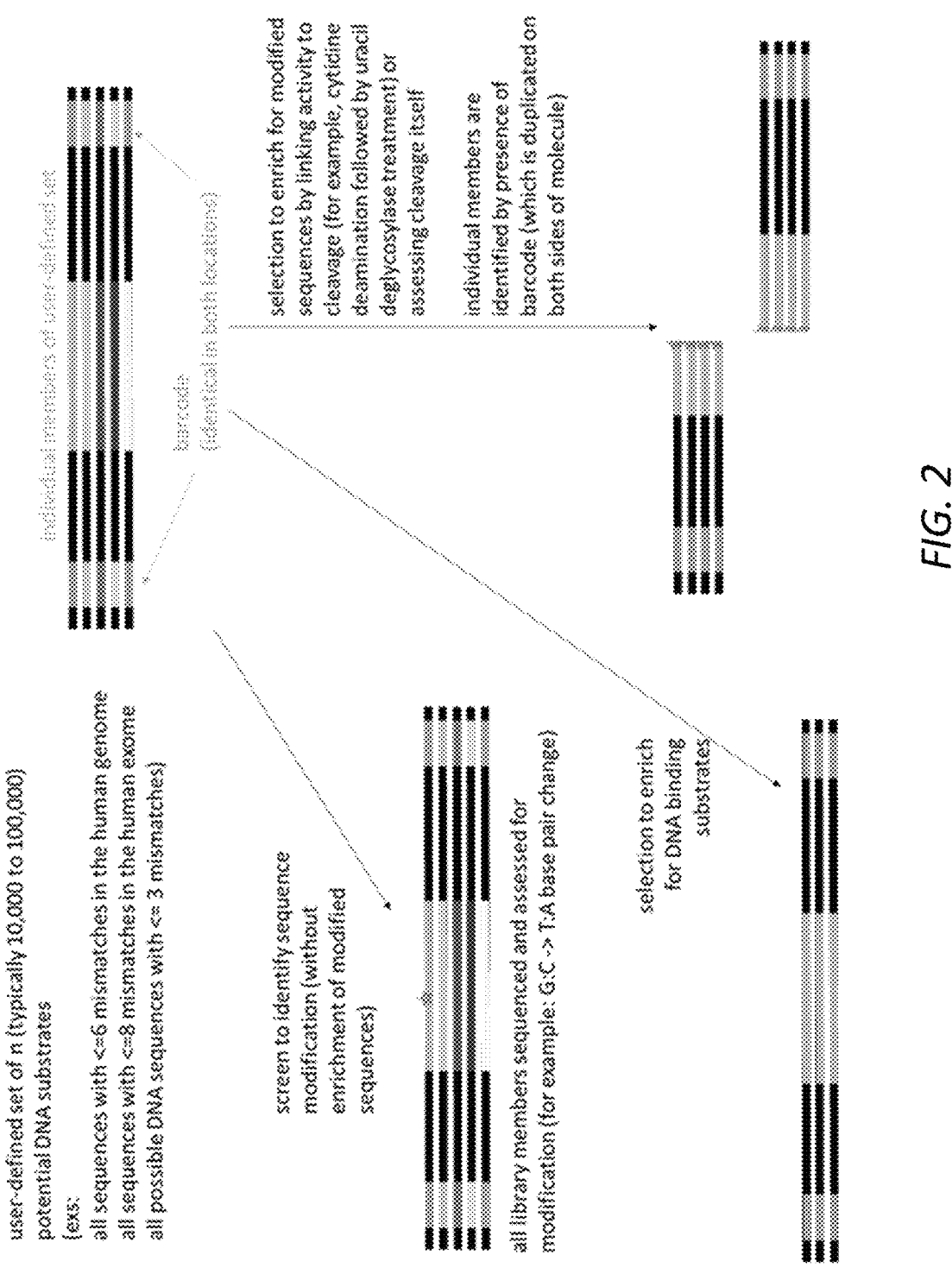
FIG. 2. Illustrative overview of exemplary method. A user-defined set (typically, but not limited to, 10,000 to 100,000 sequences) of potential DNA substrates is generated by synthesis on a high-density oligonucleotide array and then made double-stranded. Three potential examples of sets of sequences to use include the set of all sequences with up to six mismatches in the human genome, eight mismatches in the human exome, or all possible DNA sequences with up to three mismatches. The double-stranded DNA library can then be used in screens for sequence modification, screens for sequence depletion, or selection for sequence modification and/or cleavage. Black lines indicate constant sequence that is present in every member of the library and is used for primer binding sites during amplification steps and in bioinformatic processing.

In vitro/biochemical strategies to understanding on- and off-target activity of DNA binding domains generally fall into two types (FIG. 1): In the first type, a set of DNA sequences in a relevant defined system (for example, the human genome) is interrogated for off-target cleavage events. Examples of methods that utilize this strategy include CIRCLE-seq (Tsai et al., Nat Meth. 14: 607 (2017)], SITE-seq (Cameron et al. Nat Meth. 14: 600 (2017)), and Digenome-seq (Kim et al. Nat Meth. 12: 237 (2015)). The scope of these genome-wide methods is restricted to off-target sites that are present in the particular genomic DNA used in the study. In contrast, in the second type of strategy, the substrate preference of the DNA binding/modifying protein is assayed in a more unbiased fashion by comprehensively interrogating a library of binding sites in which certain base positions are randomly substituted with all potential alternative bases (rather than just a limited set of base substitutions as in the case of the first strategy). These "genomic DNA" and "random base substitution library" approaches have been carried out for various nucleases (ZFNs (Pattanayak et al. Nat Meth. 8: 765 (2011)], TALENs (Guilinger et al. Nat Meth. 11: 429 (2014)), and CRISPR-Cas9 (Pattanayak et al. Nat Biotech. 31: 839 (2013))) in vitro and provide insights into the biochemical function and specificity of these nucleases.

Both types of strategies to study off-target activity have limitations that affect their abilities to identify bona fide off-target sites. In genome-wide selections, the tens to hundreds of cleaved off-target sites must be enriched from a background of billions of other sites that are not cleaved (the human genome has a length of ~3 billion base pairs and therefore contains ~6 billion sites to be assayed). For example, due to noise in the enrichment method and in the sequencing results, the CIRCLE-seq method is limited to detection of sites that have no more than six mismatches relative to the on-target site, which represents only ~0.002% of the genomic material present in the assay. While some methods, such as Digenome-seq, rely on massive over sequencing of nuclease treated DNA libraries, methods like CIRCLE-seq and GUIDE-seq typically incorporate an enrichment step for edited sequences. This enrichment step can be performed in cells (GUIDE-seq) or in vitro (CIRCLE-seq). Although it is substantially more sensitive than other methods for off-target screening, the CIRCLE-seq method requires a very large input of genomic DNA (25 µg) for each experimental sample.

In vitro selections on unbiased base substitution libraries are limited by library size (the set of sequences that can practically be assayed). For example, an SpCas9 target site contains 22 potentially-specified base pairs (20 from hybridization to the guide RNA and two from the PAM sequence). To assay all potential target sites bearing all possible combinations of base substitutions at all positions, at least $4^{22} \sim 10^{13}$ unique molecules of DNA, would need to be generated and interrogated, neither of which is possible using current technologies. For example, library construction methodologies are currently limited to producing $10^{11}$-$10^{12}$ unique molecules of DNA. Furthermore, even if library construction methodologies were improved, it is not feasible to sequence $10^{12}$ molecules of DNA. To overcome this restriction, doped oligonucleotide synthesis is traditionally used to create a library of sites bearing base substitutions that follow a binomial distribution, such that the on-target site is present in more copies than each variant site in the library bearing a single mutation, each of which are present in more copies than each variant site in the library bearing double variant site, and so forth. Therefore, selections performed with these random base substitution libraries are limited by the fact that 1) it is not possible to create a completely unbiased library (i.e., they are heavily biased towards the intended on-target site sequence) and 2) it is not possible to create a library that uniformly represents the potential sequence space. Furthermore, using the outputs from defined libraries assays to predict or identify off-target sites in genomic sequences often requires extrapolation (Sander et al. Nucleic Acids Res. 41: e181 (2013)), because not all relevant genomic sequences are guaranteed to be covered in pre-selection (limited to $10^{12}$ sequences, which corresponds to six or seven substitutions) or post-selection libraries (limited to $10^{7-8}$ sequences by sequencing capacity).

Methods of Identifying DNA Binding, Modification, or Cleavage Sites

Herein, we provide improved methods (FIG. 2) that enable identification of on- and off-target binding, modification, or cleavage sites of DNA modifying proteins/protein complexes (including but not limited to: dCas9 fused to an effector domain, Cas9-based base editors, or active Cas9 proteins) and that overcomes the disadvantages of both the "genomic DNA" and "random base substitution library" approaches. With this method, a pre-enriched library of linear DNAs consisting of particular user-specified sequences is generated by high-density oligonucleotide synthesis and then interrogated for those sequences that can be bound, modified or cleaved by sequence-specific proteins or protein complexes. Minimally, this method allows for the identification of sequences that are potential substrates for any agent whose modifying action can lead to sequence modification, binding, or cleavage of nucleic acid.

The pre-enriched linear DNA library members are initially synthesized on high-density oligonucleotide arrays as individual single-stranded DNA sequences, each bearing a unique identifier/barcode, which is present/duplicated on both sides of the oligonucleotide (FIG. 2). The synthesized oligos are released from the chip and converted into double-stranded DNA molecules by priming against a common sequence present in all DNA molecules synthesized on the chip. This pooled library is then incubated with a site-specific nuclease, modifying protein, or DNA binding domain of interest and either enriched for cleaved, modified, or bound sequences in a selection format (see examples 1, 3, and 4) or screened for modification (see example 2). The DNA sequences of cleaved sites can then be reconstructed from either of the identical barcodes that originally flanked these sites and that are now separated into two molecules.

Synthesized molecules can be specified to represent 1) a set of all potential off-target sequences in a reference genome bearing up to a certain number of mismatches relative to the on-target site (analogous to genomic DNA libraries), 2) a comprehensive set of potential off-target sites bearing up to a certain number of mismatches (analogous to random base substitution libraries), 3) a library of potential off-target sequences present in a set of variant genomes from defined populations (i.e., genomic DNA libraries designed to reflect DNA sequence variants present in a population of individuals), or 4) other relevant defined sets of potential off-target sites (for example, oncogene hotspots or sequences from tumor suppressor genes). This strategy has important advantages for constructing these libraries. For random base substitution libraries, all sequences within a defined number of substitutions can be represented equally and can be easily sampled with current next-generation sequencing methodologies. For genomic or exomic DNA libraries, only the sites that are most likely to be relevant (for example, all potential off-target sites with six or fewer substitutions) are included, which eliminates the noise contributed by the ~99.998% of sites that are not substrates. Importantly, because this method results in the generation of a double-strand DNA (or RNA) library of an enriched set of potential off-target sites of a DNA (or RNA) binding protein, it can be used to define the specificity and off-target sites of not only nucleases but also other proteins that bind or modify nucleic-acid, including but not limited to, customizable base editing enzymes (Komor et al. Nature 533: 420, 2016, Gaudelli et al. Nature. 551: 464 (2017)), transcriptional activators (Mali et al, Nat Biotech. 31: 833 (2013), Chavez et al. Nat Meth. 12: 326 (2015)), transcriptional repressors (Bikard et al, Nucleic Acids Res, 41: 7429 (2013), Thakore et al. Nat Meth. 12: 1143 (2015)), and epigenome editing enzymes (reviewed in Zentner and Henikoff. Nat Biotech. 33: 606 (2015)).

The ability to define identical barcodes flanking a defined recognition site represents a significant advance over previous in vitro profiling methods (U.S. Pat. Nos. 9,322,006, 9,163,284), because the sequence of the library member is encoded in at least three locations on each individual member of a DNA pool. This redundancy of information is particularly advantageous when seeking to define DNA modifying activity (such as base editing) where the target sequence is modified. The original sequence information can be obtained from the information content contained in a flanking barcode, even if the actual DNA sequence of the library member itself is modified. The redundancy of information in two barcodes and a recognition site also allows for an endonuclease cleavage selection (or paired base modification +cleavage selection) to be performed on potential cleavage sites that are present in a single copy per library member, as opposed to multiple copies (U.S. Pat. Nos. 9,322,006, 9,163,284). Without the present barcoding strategy, sequences of library members that get cleaved within a recognition site cannot be reassembled, since the cut separates in space the two sides of the cut site (FIG. 2, bottom right).

EXAMPLES

The invention is further described in the following examples, which do not limit the scope of the invention described in the claims.

Target sites used in following examples:

| target name | Sequence (5'→3') | SEQ ID NO: |
|---|---|---|
| EMX1 | GAGTCCGAGCAGAAGAAGAAGGG | 22 |
| RNF2 | GTCATCTTAGTCATTACCTGAGG | 42 |
| FANCF | GGAATCCCTTCTGCAGCACCTGG | 43 |
| HBB | TTGCCCCACAGGGCAGTAACGG | 44 |
| HEK2 (HEK293_2) | GAACACAAAGCATAGACTGCGGG | 45 |
| HEK3 (HEK293_3) | GGCCCAGACTGAGCACGTGATGG | 46 |
| HEK4 (HEK293_4) | GGCACTGCGGCTGGAGGTGGGGG | 47 |
| ABE14 (ABE_14) | GGCTAAAGACCATAGACTGTGGG | 48 |
| ABE16 (ABE_16) | GGGAATAAATCATAGAATCCTGG | 49 |
| ABE18 (ABE_18) | ACACACACACTTAGAATCTGTGG | 50 |
| VEGFA3 (VEGFA_3) | GGTGAGTGAGTGTGTGCGTGTGG | 51 |

Example 1: DNA Cleavage Selection with SpCas9 and SpCas9-HF1

In this example, a random base substitution library designed for an SpCas9 nuclease programmed with a guide RNA (gRNA) designed against an on-target site in the human EMX1 gene (hereafter referred to as the EMX1 gRNA and EMX1 target site) and a library of potential EMX1 gRNA off-target sites from the human reference genome were selected for cleavage with SpCas9 or SpCas9-HF1.

Figure 3:
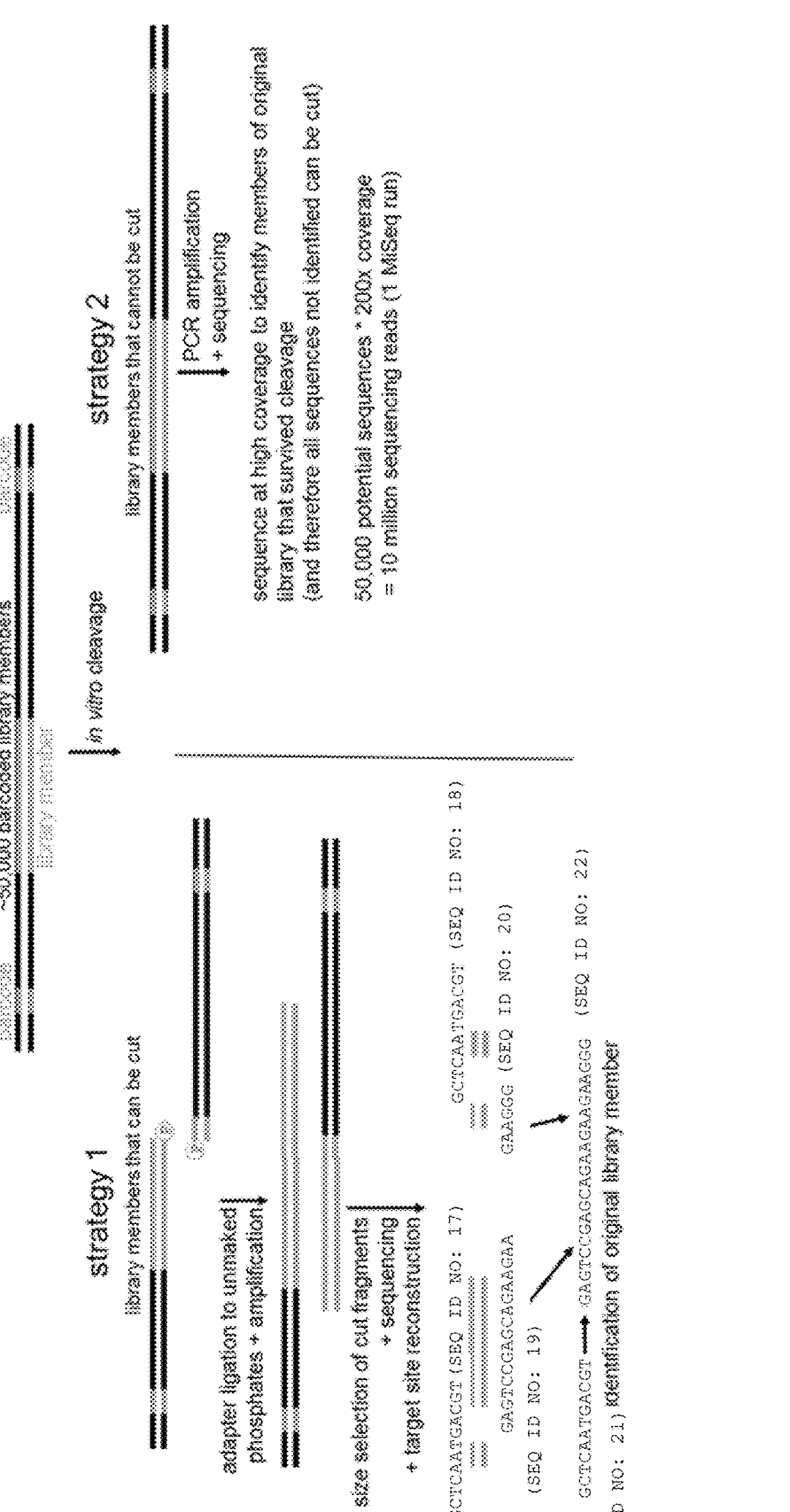
FIG. 3. Target site libraries can be selected for cleavage (strategy 1) or screened for depletion of cleaved sequences (strategy 2). Black lines indicate constant sequence that is present in every member of the library and is used for primer binding sites during amplification steps and in bioinformatic processing. SEQ ID NOs.: 17-22 are shown.
Figure 4:
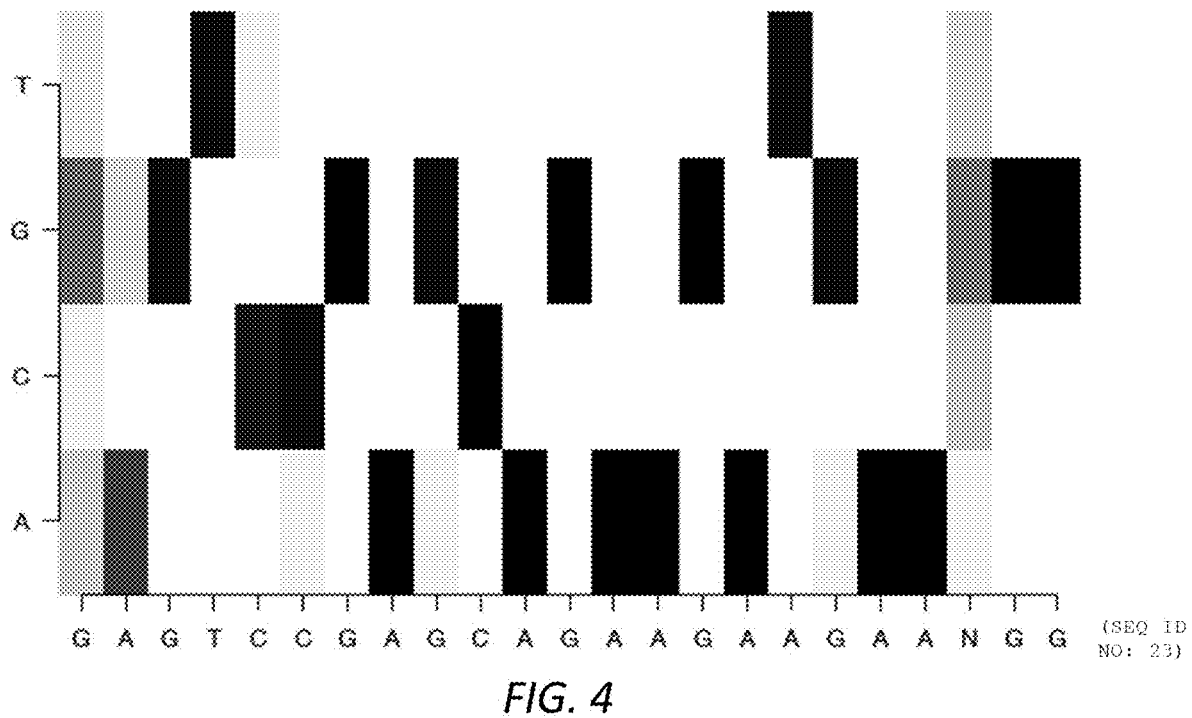
FIG. 4. Enrichment of Cas9 cleavage sites by selection from a random base substitution library. The intended target site (SEQ ID NO:23) is listed below the heat map. Each box represents the abundance of a particular nucleotide (denoted on left) at the position corresponding to the target site nucleotide listed below, on a black to white scale, with black representing the most abundant nucleotides/per position and white representing no abundance.

In this example (FIG. 3), both a selection (strategy 1) and a screen (strategy 2) can be employed. In strategy 1, a pooled library of ~50,000 barcoded library members (either a random base substitution library containing all possible sequences within three mismatches of an EMX1 SpCas9 on-target site or a genomic DNA-inspired library containing all possible sequences from the hg19 human reference genome within six mismatches of an EMX1 SpCas9 on-target site-see Methods for details of libraries.) A selection performed using strategy 1 on the random base substitution library with a 1:1:1 ratio of SpCas9:sgRNA:DNA library (EMX1 target sites) demonstrated enrichment of sequences that could be cleaved (FIG. 4). The positions in the target site are on the horizontal axis (with the on target bases listed below). The possible bases (substitutions or on-target) in the library are indicated on the vertical axis. Data was pooled and summarized in a heatmap, where darker black rectangles indicate a larger proportion of sites in the post-selection library containing the corresponding base from the vertical axis. As a proof of principle, this heatmap agrees with previous studies that demonstrate the N of the NGG PAM sequence is not specified and that specificity at the PAM-distal end of the target site is lower than that of the PAM-proximal end.

A screen performed using strategy 2 with the random base substitution library yielded similar results (FIG. 5). Substrates with fewer numbers of mutations (indicated by lower m numbers, where (m_d_i)→m=number of mutations, i=number of insertions, d=number of deletions) in the substrate profiling library and in the genome-inspired library where Xm0 denotes m mismatches without any insertions, RNAmd indicates a target site deletion of length d with m mismatches at the remaining base pairs in the site, DNAmi indicates a target site insertion of length I with m mismatches at the remaining base pairs in the site).

Genomic libraries are generally composed of all potential off-target sites in the hg19 reference human genome that had zero to six mismatches relative to the on-target sequence, up to four mismatches in combination with a DNA bulge of one or two nucleotides, and up to four mismatches with an RNA bulge of one nucleotide, and up to three mismatches with an RNA bulge of two nucleotides (FIG. 6). Sequencing of pre-selection libraries to assess quality metrics (FIG. 7) demonstrated a low dropout rate (0.20% or less) and high uniformity (90/10 ratio>~2). These metrics have not, to our knowledge, been calculated for other specificity methods, so direct comparison is not possible.

Figure 8:
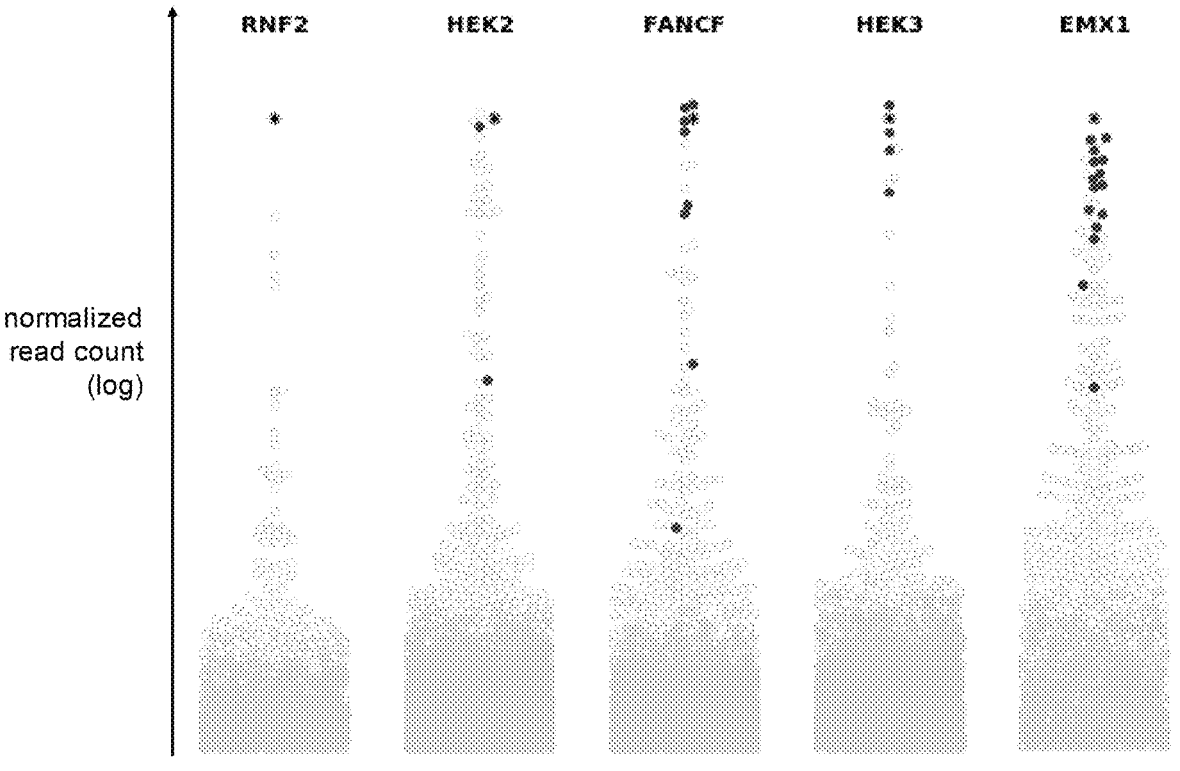
FIG. 8. Enrichment of known GUIDE-seq sites. Swarm plots are shown for representative cleavage selections using a method described herein (an example of which is referred to as the ONE-seq method). Each circle represents the aggregate read counts, normalized to the on-target sequence for a given guide RNA selection (listed on top), for an individual library member. The black stars indicate the on-target library member. Filled circles denote sites that were identified by published GUIDE-seq experiments. There were no published RNF2 GUIDE-seq sites.
Figure 9:
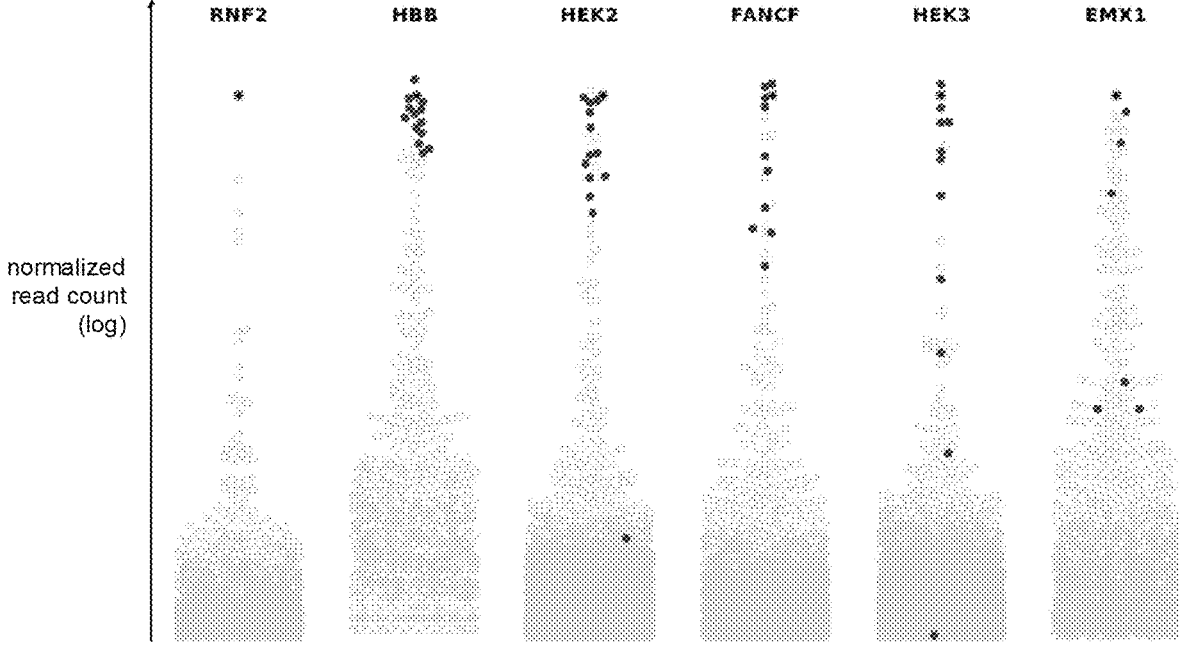
FIG. 9. Enrichment of highly enriched CIRCLE-seq sites. Swarm plots are shown for representative cleavage selections using the ONE-seq method. Each circle represents the aggregate read counts, normalized to the on-target sequence for a given guide RNA selection (listed on top), for an individual library member. The black stars indicate the on-target library member. Filled circles denote sites with >100 read counts that were identified by published CIRCLE-seq experiments. There were no published RNF2 GUIDE-seq sites.

Selections were performed using strategy 1 (referred to as ONE-seq) with genomic DNA-inspired libraries for six non-promiscuous guide RNAs (HBB, RNF2, HEK2, HEK3, FANCF, and EMX1) with relatively few expected off-target sequences. On target sequences (FIG. 8, black stars) were either the most enriched or among the top 3 most enriched library members out of tens of thousands for the six non-promiscuous guide RNAs tested. Summed over the six non-promiscuous guide RNAs, ONE-seq enriched all 163 GUIDE-seq identified off-target sites (FIG. 8, filled circles), with post-selection read counts of ranging from 11% to 120% of the on-target sequences. This method also enriches highly enriched CIRCLE-seq sites (defined here as those with >100 sequence reads, FIG. 9), and appropriately, enriches to a lesser extent CIRCLE-seq sites that are moderately enriched (10-99 reads, FIG. 10), or lowly enriched (1-9 reads, FIG. 11).

Figure 12:
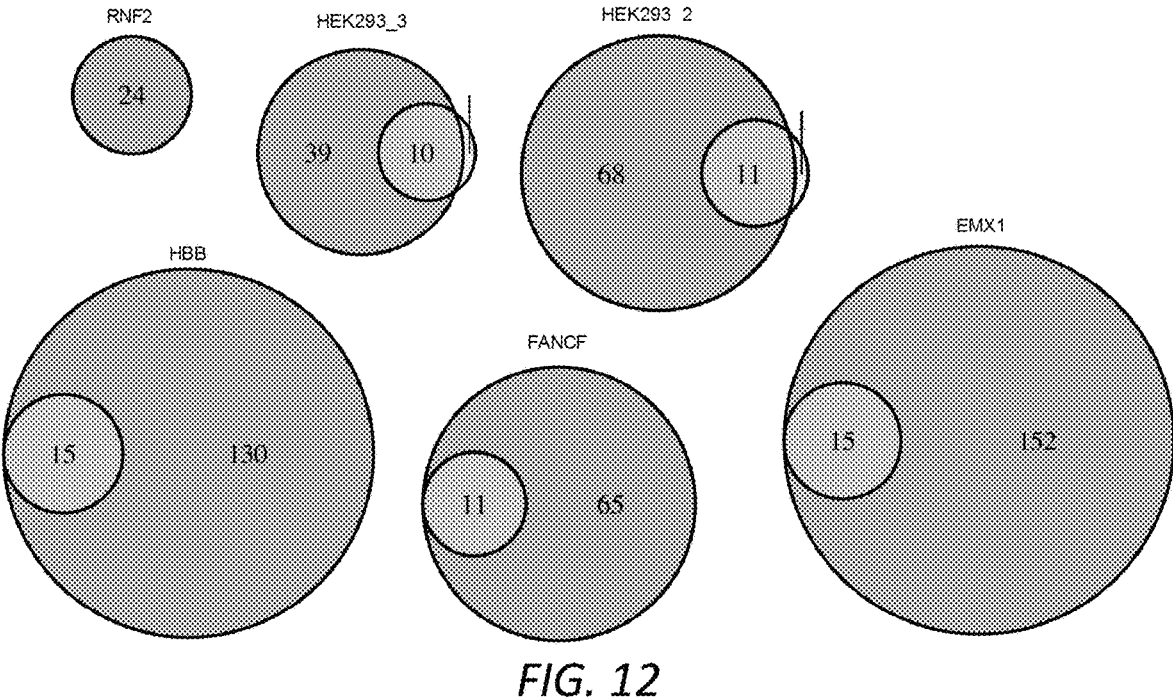
FIG. 12. Venn diagrams showing that the exemplary method (darker circles) identifies all 60 out of 62 highly enriched (>100 reads) CIRCLE-seq sites (lighter circles) of six SpCas9:sgRNA, using a cutoff of 1% of the on-target ONE-seq aggregated read count. The 2 sites that were not above the 1% ONE-seq cutoff do not necessarily represent bona fide off-target sequences and may be false positives in the CIRCLE-seq method. CIRCLE-seq does not identify 478 of the ONE-seq identified sites for these guide RNAs.

If a cutoff of 1% of the on-target enrichment in the ONE-seq method described here, ONE-seq identifies 60 out of 62 highly enriched CIRCLE-seq sites (FIG. 12), while CIRCLE-seq fails to identify 478 highly enriched ONE-seq candidates. Of note, the 2 highly enriched CIRCLE-seq sites that are not highly enriched by ONE-seq may be false positives of the CIRCLE-seq method. Validation of ONE-seq sites that are novel and not identified by GUIDE-seq or CIRCLE-seq was demonstrated by sorting HEK293T cells in the top decile of SpCas9:FANCF sgRNA expression (FIG. 13). These results demonstrate that the method described here is at least as sensitive as existing methods and is likely more sensitive.

Figure 14:
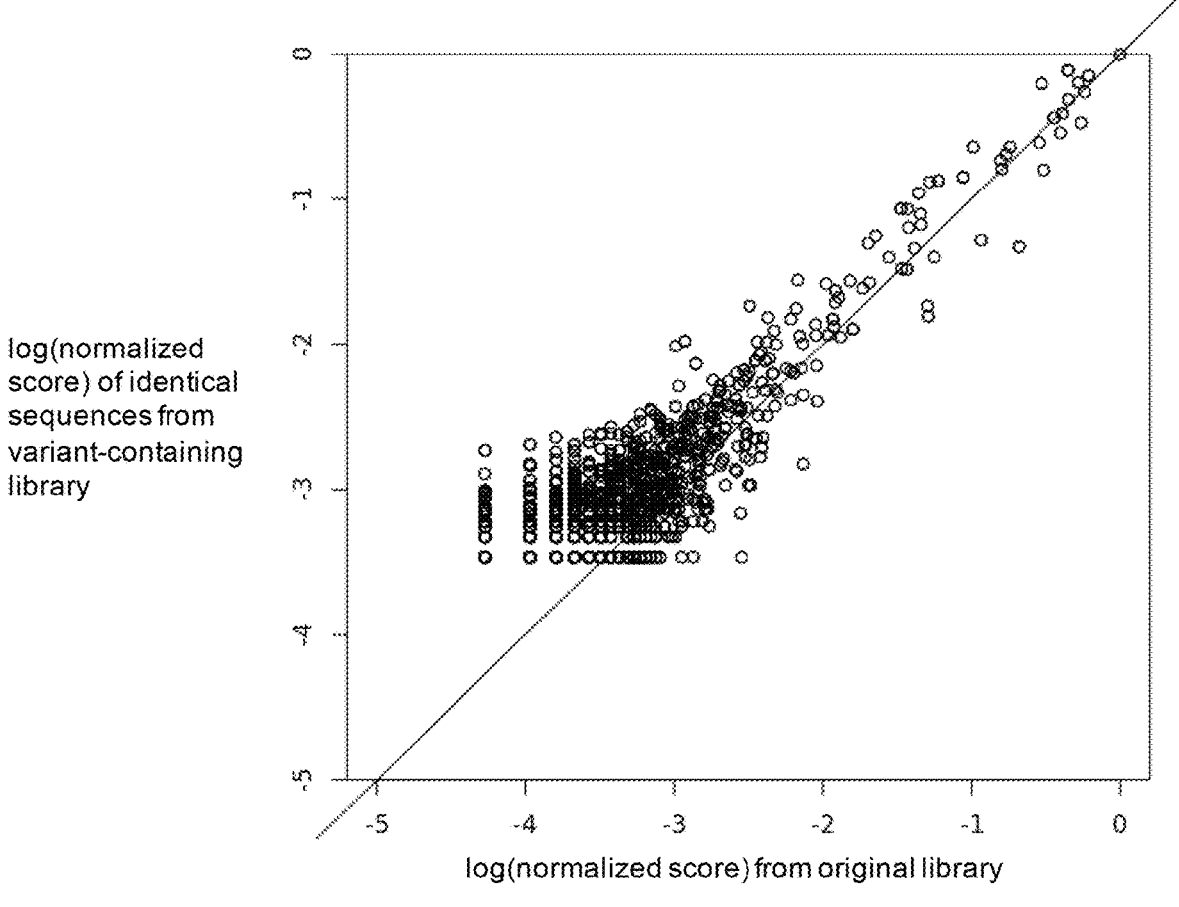
FIG. 14. Reproducibility of enrichment scores in variant libraries. ONE-seq selections were performed on an EMX1 genomic off-target library and an EMX1 genomic variant off-target library. Enrichment scores (relative to the on-target sequence) are shown for the library members that are shared by both libraries. The superimposed line corresponds to equal enrichment scores from both selections.
Figure 15:
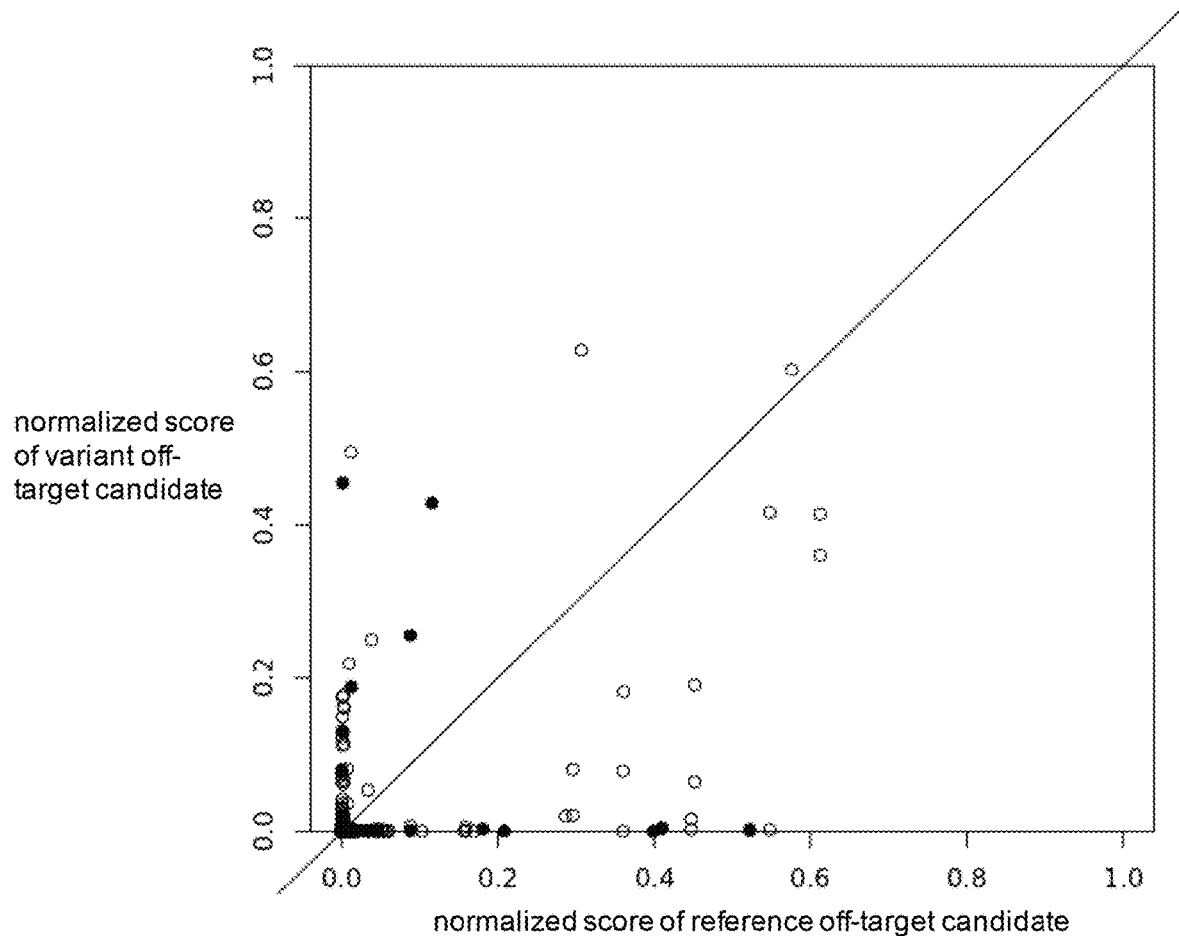
FIG. 15. ONE-seq identifies candidate off-target sites that are present in the population but not in the reference genome. Normalized aggregate read counts (where 1.0 is the on-target site) are shown for off-target candidates identified from the reference genome and paired off-target candidates that contain SNPs found in the 1000 genomes population. Variants that are present in >40% of the population are shown with filled circles. The superimposed line corresponds to equal enrichment scores from both paired library members.
Figure 16:
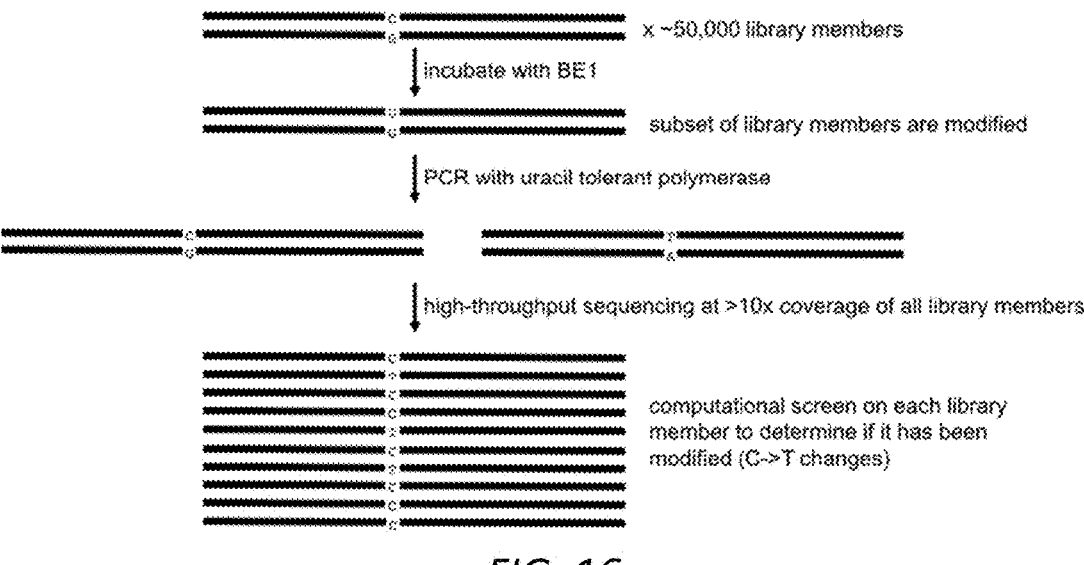
FIG. 16. Base editor screening strategy. A random base substitution library designed for the EMX1 target site was incubated in vitro with BE1, and amplified by PCR with Kapa HiFi Uracil+ DNA polymerase, which converts U:G base pairs to equal mixtures of T:A and C:G base pairs during DNA synthesis (a dATP nucleotide is incorporated across from dU). Therefore, any library member that can be modified by BE1, when sequenced, will sequence as a mixture of the original barcode-linked sequence from the pre-treatment library and also a modified sequence that contains C→T substitutions (and other rarer substitutions).
Figure 17:
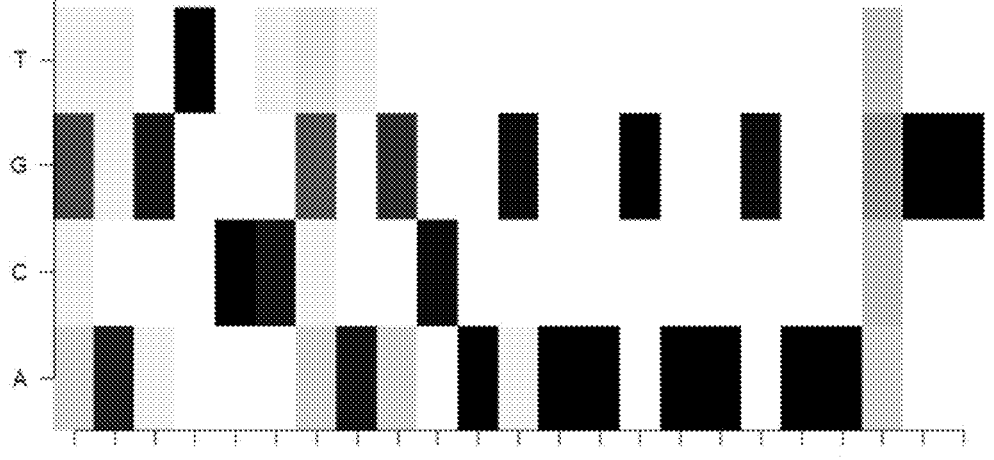
FIG. 17. Base editor screen demonstrates enrichment of sites containing NGG and demonstrates high specificity at the PAM-proximal end of the target site (SEQ ID NO:23) and lower specificity at the PAM distal end. Heat map is interpreted in the same way as in FIG. 4.

In addition, this method can be generalized to any library/defined set of nucleic acid sequences. For example, using publicly available data from the 1000 genomes project, ONE-seq selections were performed on an EMX1 genomic off-target site library that accounts for naturally occurring sequence variation on a population scale. In this example library, all sequences from the reference hg19 human genome assembly that were in the original EMX1 library (FIG. 6) and contained a SNP in the 1000 genomes database were included. In addition, the SNP containing sequences were also included as additional library members to account for the possibility that individuals may have off-target sequences that are not contained in the reference genome. A ONE-seq cleavage selection performed on this SNP-containing EMX1 library provides reproducible enrichment of off-target candidates that are present in the reference hg19 genome (FIG. 14). ONE-seq cleavage selections on the variant library demonstrate assessment of tens of thousands of variants present in the population for a candidate set of off-target sites of the EMX1 guide RNA, identifying several (FIG. 15, black circles) that are differentially enriched.

Example 2: Base Editor Screen with BE1

Figure 18:
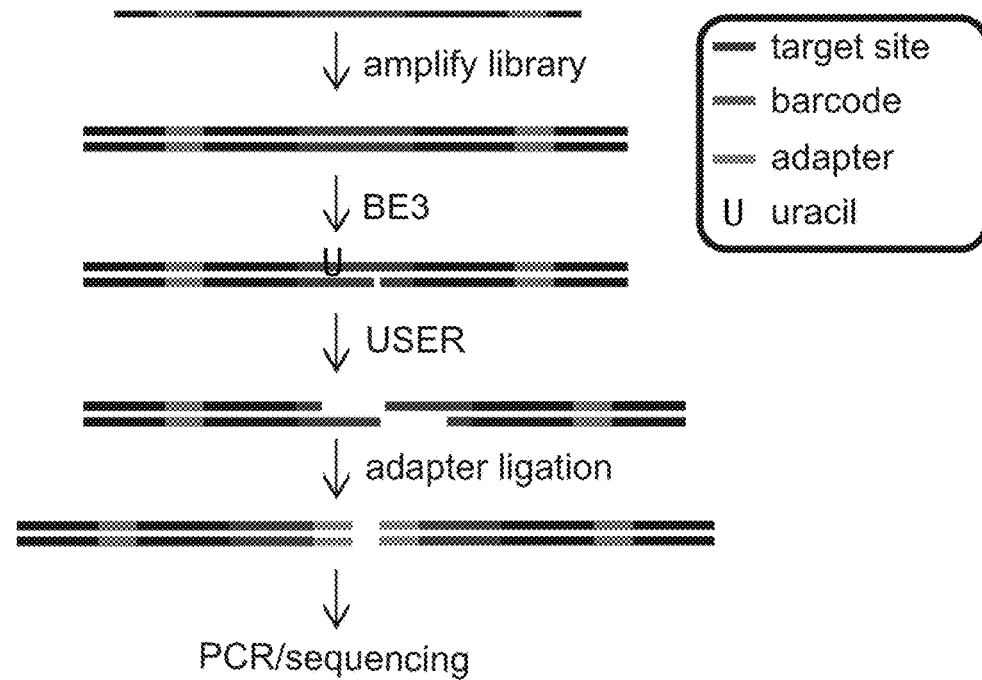
FIG. 18. BE3 selection strategy. In this strategy, target site libraries are exposed to BE3 enzyme and are enriched for modified members through double-strand break creation at sites with uridine nucleotides (through USER®, a mixture of Uracil DNA glycosylates (UDG) and the DNA glycosylate-lyase Endonuclease VIII) and nicks (through BE3).

In this example (FIG. 18), a selection strategy was used to enrich for sites that are modified by the BE3 enzyme. Library members that can be recognized by the BE3 enzyme (Komor et al. Nature 533:420, 2016) should exhibit both C→U modification and a nick on the opposite strand. The USER® enzyme (NEB) (a mixture of Uracil DNA glycosylates (UDG) and the DNA glycosylate-lyase Endonuclease VIII) was used to achieve double stranded cleavage of library members that are BE3 substrates by replacing dU nucleotides with a nick. Resulting modified library members will therefore contain two nicks with 5' phosphates on opposite strands and are incubated with a DNA polymerase that can blunt these DNA overhangs (ex: T4 DNA polymerase or PHUSION® DNA polymerase (a high-fidelity thermostable polymerase with 5'→3' polymerase activity and 3'→5' exonuclease activity that generates blunt ends)). The resulting phosphorylated blunt ends are captured with double stranded DNA adapters prior to amplification/selection using one primer specific to the adapter and one primer specific to the library backbone (as in Example 1). Additional selection stringency can be obtained by performing size selection for smaller, cut fragments before or after amplification.

Example 3: Base Editor Selection with BE3

In this example (FIG. 18), a selection strategy was used to enrich for sites that are modified by the BE3 enzyme. Library members that can be recognized by the BE3 enzyme (Komor et al. Nature 533: 420, 2016) should exhibit both C→U modification and a nick on the opposite strand. The USER enzyme (NEB) was used to achieve double stranded cleavage of library members that are BE3 substrates by replacing dU nucleotides with a nick. Resulting modified library members will therefore contain two nicks with 5' phosphates on opposite strands and are incubated with a DNA polymerase that can blunt these DNA overhangs (ex: T4 DNA polymerase or Phusion DNA polymerase). The resulting phosphorylated blunt ends are captured with double stranded DNA adapters prior to amplification/selection using one primer specific to the adapter and one primer specific to the library backbone (as in Example 1). Additional selection stringency can be obtained by performing size selection for smaller, cut fragments before or after amplification.

Figure 19:
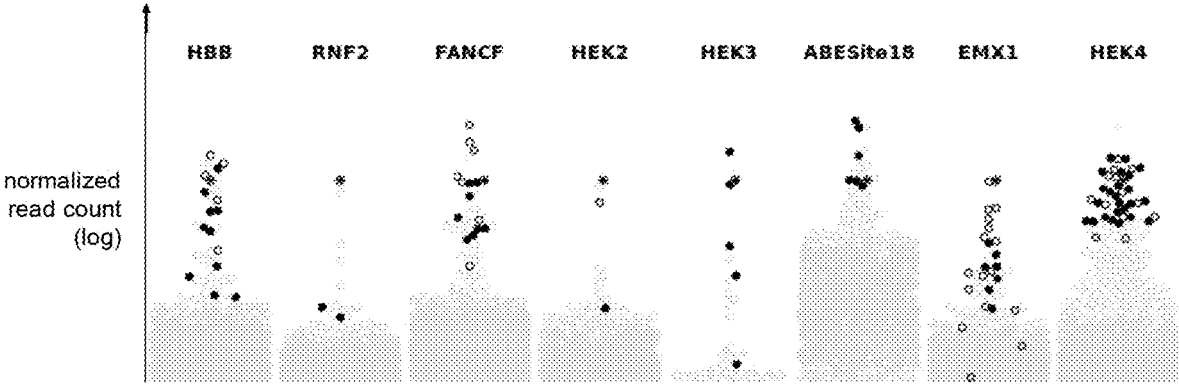
FIG. 19. Enrichment of BE3 off-target sites by ONE-seq. Normalized aggregate read counts (where 1.0 corresponds to the on-target site) are shown for eight ONE-seq selections on genomic DNA-inspired libraries. Only sites with a score of 0.01 or greater (1% of on-target enrichment) are shown. Black stars represent on-target library members. Filled in black circles denote newly validated off-target sites compared to Digenome-seq (with the exception of ABE Site 18, which was not tested by Digenome-seq). Open black circles denote Digenome-seq candidate sites.

Using this approach, we examined BE3 targeting with genomic DNA-inspired libraries for eight target sites, including all seven BE3 targets tested previously by Digenome-seq (Kim et al. Nat. Biotech. 35:475, 2017). ONE-seq selection results revealed enrichment of the intended target sites to the top 13 of tens of thousands of library members for all eight selections (FIG. 19, black stars). For three out of the eight selections, the intended target site was the most enriched site. All 42 previously validated off-target sites by Digenome-seq were present in the enriched, post-selection libraries (FIG. 19, open black circles), and 40 out of the 42 were among the top 61 sites for each selection. To further validate our ONE-seq results, we amplified and sequenced from human HEK293T cells approximately 20-40 highly-ranking sites from each selection. Our results demonstrated 28 validated BE3 off-target sites that were not identified as candidates by Digenome-seq (FIG. 19, solid black circles). Six of the 28 new sites had edit percentages greater than 1% in cells (FIG. 20), with a high of 23.9%, suggesting a higher level of sensitivity of ONE-seq for detecting not only weak off-target sites but also high frequency off-target sites.

Example 4: Base Editor Selection with ABE

Figure 21:
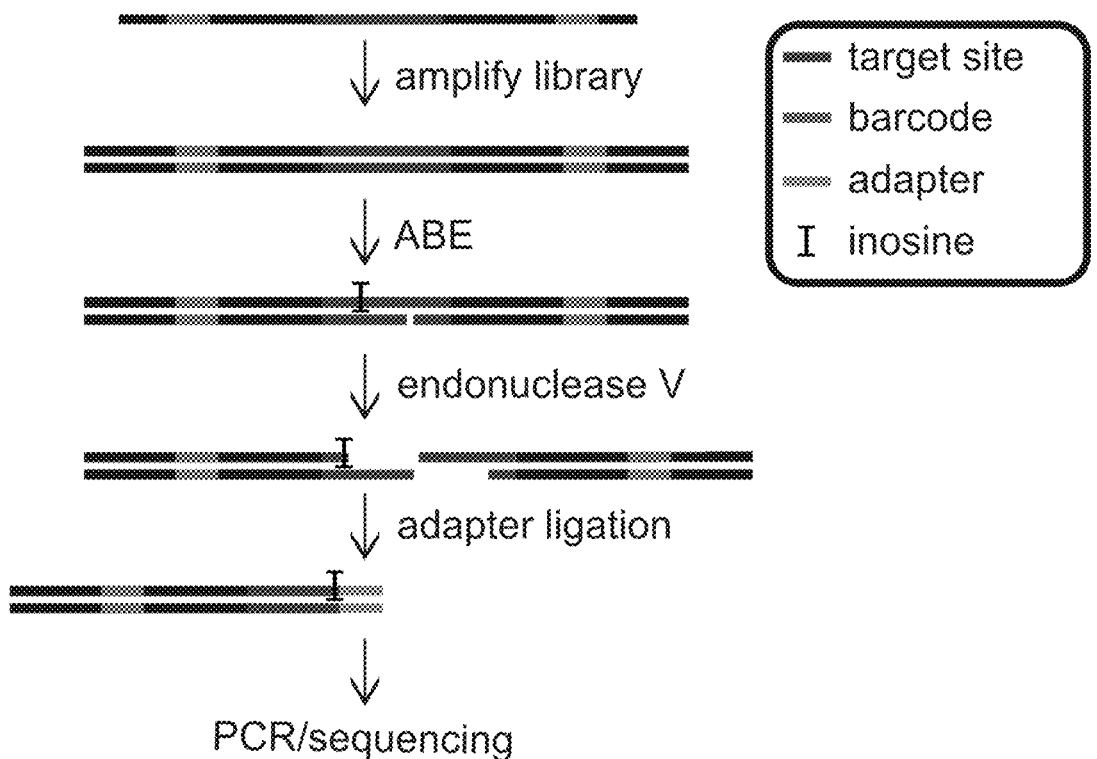
FIG. 21. ABE selection strategy. In this example, the Adenine base editor (ABE) is used. ABE creates A→I changes in DNA. The method we use here to define off-target sites of ABE is similar to that used in Example 3, except a different endonuclease, endonuclease V, is used to create a nick at a deoxyinosine site in DNA.

In this example (FIG. 21), we performed a selection using Adenine base editor (ABE; Gaudelli et al. Nature. 551: 464 (2017)) with the EMX1 gRNA and a base substitution profiling library and the genomic DNA library. ABEs are sgRNA-guided Cas9 nickases fused to a protein domain that can catalyze the conversion of deoxyadenosine to deoxyinosine. In this example, double strand cleavage of the pre-selection library is accomplished in two steps (FIG. 21). First, incubation with ABE enzyme and guide RNA leads to nick formation of the strand of a recognized library member that hybridizes to the guide RNA. Second, subsequent incubation with Endonuclease V, an enzyme that creates a nick to the 3' of deoxyinosines in library members that could result from ABE activity, leads to nick formation on the non-hybridized DNA strand, leading to a double strand break with an overhang. Subsequent fill-in of the double strand break with a DNA polymerase leads to the formation of blunt ends, which can be selected for as described for Cas9 nucleases in Example 1.

Figure 22:
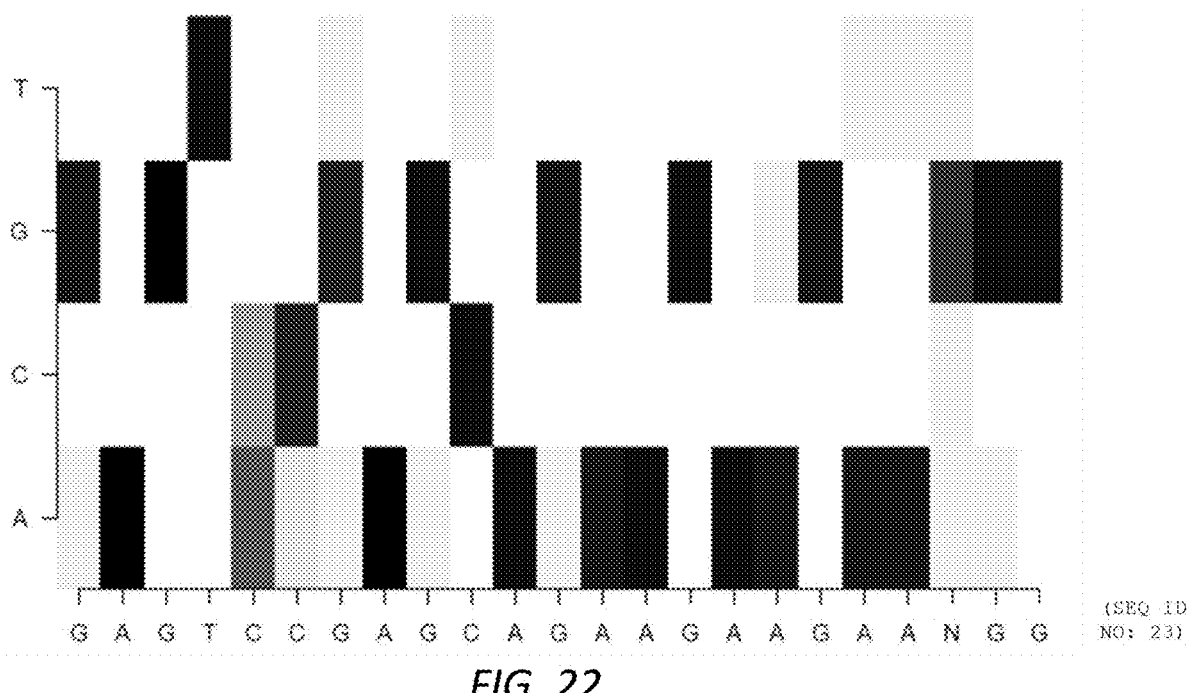
FIG. 22. ABE selection on a base substitution library. Heatmap is interpreted in same way as in FIG. 4. The data from the selection demonstrate enrichment of NGG PAMs, but also enrichment of sequences containing an A at position five, relative to the SpCas9 cleavage selection in FIG. 4 and the BE3 selection in FIG. 8, demonstrating the need for an A in a certain editing window for ABE to demonstrate activity. (SEQ ID NO:23)

Selection of the base substitution library demonstrates enrichment of substrates with an NGG. In addition, as expected, this experiment (FIG. 22) demonstrates enrichment of substrates with an A at position five of the target site (where 1 is the base pair most distal from the PAM), reflecting a preference of ABE for modification of an A more distal to the PAM than is present in the canonical EMX1 target site. Of note, of the 100 most abundant sequences in the post-selection library, 95 had an A at position 5. These results demonstrate that our strategy works to enrich and identify off-target sites of the ABE.

TABLE 1

Enrichment of sequences with an A in position 5 in the ABE selection.

| First five nucleotides of post-selection library member | Number of times observed out of the top 100 most enriched post-selection library members |
|---|---|
| GAGTA | 83 |
| AAGTA | 12 |
| GAGTC (canonical first five nucleotides) | 3 |

TABLE 1-continued

Enrichment of sequences with an A in position 5 in the ABE selection.

| First five nucleotides of post-selection library member | Number of times observed out of the top 100 most enriched post-selection library members |
|---|---|
| GAAGT | 1 |
| GGAGT | 1 |

We have also performed the above selection on the EMX1 genomic DNA library (Table 2), which demonstrates enrichment of the EMX1 on-target site (highlighted; 96th most abundant post-selection library sequence) and the EMX1 off-target site with the highest off-target recognition (bold and asterisk; 9th most abundant post-selection).

TABLE 2

Top 96 most-enriched sites in the post-selection library for an ABE selection on a genomic DNA library of potential EMX1 off-target sites.

| chromo-some | location | target | SEQ ID NO: |
|---|---|---|---|
| chr4 | 33321459 | GTACAGGAGCAGGAGAAGAATGG | 52 |
| chr17 | 72740376 | CAAACGGAGCAGAAGAAGAAAGG | 53 |
| chr10 | 58848711 | GAGCACGAGCAAGAGAAGAAGGG | 54 |
| chr10 | 128080178 | GAGTACAAGCAGATGAAAAACGG | 55 |
| chr6 | 99699155 | GAGTTAGAGCAGAGGAAGAGAGG | 56 |
| chr7 | 141972555 | AAGTCCGGGCAAAAGAGGAAAGG | 57 |
| chr19 | 24250496 | GAGTCCAAGCAGTAGAGGAAGGG | 58 |
| chr11 | 111680799 | CAGTAGTGAGCAGAAGAAGATAGG | 59 |
| chr5 | 45359060\* | GAGTTAGAGCAGAAGAAGAAAGG | 60 |
| chr7 | 17446431 | GTCCAAGAGCAGGAGAAGAAGGG | 61 |
| chr12 | 106646073 | AAGTCCATGCAGAAGAGGAAGGG | 62 |
| chr15 | 22366604 | GGAGTAGAGCAGAGGAAGAAGGG | 63 |
| chr10 | 109561613 | GGAACTGAGCAAAAGAAGATAGG | 64 |
| chr11 | 62365266 | GAATCCAAGCAGAAGAAGAGAAG | 65 |
| chr2 | 21489994 | GCGACAGAGCAGAAGAAGAAGGG | 66 |
| chr1 | 234492858 | GAAGTAGAGCAGAAGAAGAAGCG | 67 |
| chr2 | 218378101 | GAGTCTAAGCAGGAGAATAAAGG | 68 |
| chr18 | 32722283 | TGTCCAGAGCAGATGAAGAATGG | 69 |
| chr22 | 22762518 | GAACATGAGCAGAAGAAGAGGAG | 70 |
| chr11 | 34538379 | AGGCCAGAGCAAAAGAAGAGAGG | 71 |
| chr11 | 106142352 | GTACAAGAGCAGGAGAAGAAGGG | 72 |
| chr15 | 91761953 | GAGTCAGGGCAGAAGAAGAAAAT | 73 |
| chr4 | 87256685 | GAGTAAGAGAAGAAGAAGAAGGG | 74 |
| chr4 | 21141327 | AAGCCCGAGCAGAAGAAGTTGAG | 75 |

TABLE 2-continued

Top 96 most-enriched sites in the post-selection
library for an ABE selection on a genomic DNA
library of potential EMX1 off-target sites.

| chromo-some | location | target | SEQ ID NO: |
|---|---|---|---|
| chr8 | 128801241 | GAGTCCTAGCAGGAGAAGAAGAG | 76 |
| chr7 | 106584579 | GAGGGGAGCAAAAGAAGGAGGG | 77 |
| chr1 | 117139004 | CAGGGAGAGCAAAAGAAGAGAGG | 78 |
| chr1 | 231750724 | GAGTCAGAGCAAAAGAAGTAGTG | 79 |
| chr15 | 44109746 | GAGTCTAAGCAGAAGAAGAAGAG | 80 |
| chr21 | 23586410 | CAGGGAGAAGAAGAAGAAGGG | 81 |
| chr7 | 2127682 | GAGTTAGAGAAGAAGAAGACTGG | 82 |
| chr10 | 98718174 | ACAATCGAGCAGCAGAAGAATGG | 83 |
| chr1 | 221020698 | GAGTAGGAGCAGATGAAGAGAGG | 84 |
| chr9 | 115729750 | CAGTATGAGCAAAAGAAGAAAGA | 85 |
| chr11 | 102753237 | GAGTCCATACAGAGGAAGAAAAG | 86 |
| chr1 | 48581991 | GAATGAGCAAAAGAAGAAAGC | 87 |
| chr12 | 73504668 | GAGTTAGAGCAGAAAAAAAATGG | 88 |
| chr1 | 184236226 | AATACAGAGCAGAAGAAGAATGG | 89 |
| chr11 | 119322554 | TAGTGAGCAGAAGAAGAGAGA | 90 |
| chr1 | 151027591 | TTCTCCAAGCAGAAGAAGAAGAG | 91 |
| chr11 | 68772640 | GAGTCCATACAGGAGAAGAAAGA | 92 |
| chr2 | 9821536 | AGGTGGGAGCAGAAGAAGAAGGG | 93 |
| chr2 | 54284994 | AAGGCAGAGCAGAGGAAGAGAGG | 94 |
| chr1 | 99102020 | GAGGCACAAGCAAAAGAAGAAAAG | 95 |
| chr19 | 1438808 | GAAGTAGAGCAGAAGAAGAAGCG | 96 |
| chr2 | 73160981 | GAGTCCGAGCAGAAGAAGAAGGG | 22 |

The two sequences highlighted are the most active cleavage off-target site (chr5: 45359060), asterisked, and the on-target site (chr2: 73160981). It is expected for the off-target site to be more enriched in the selection due to presence of an A in a more favorable position in the editing window.

Figure 23:
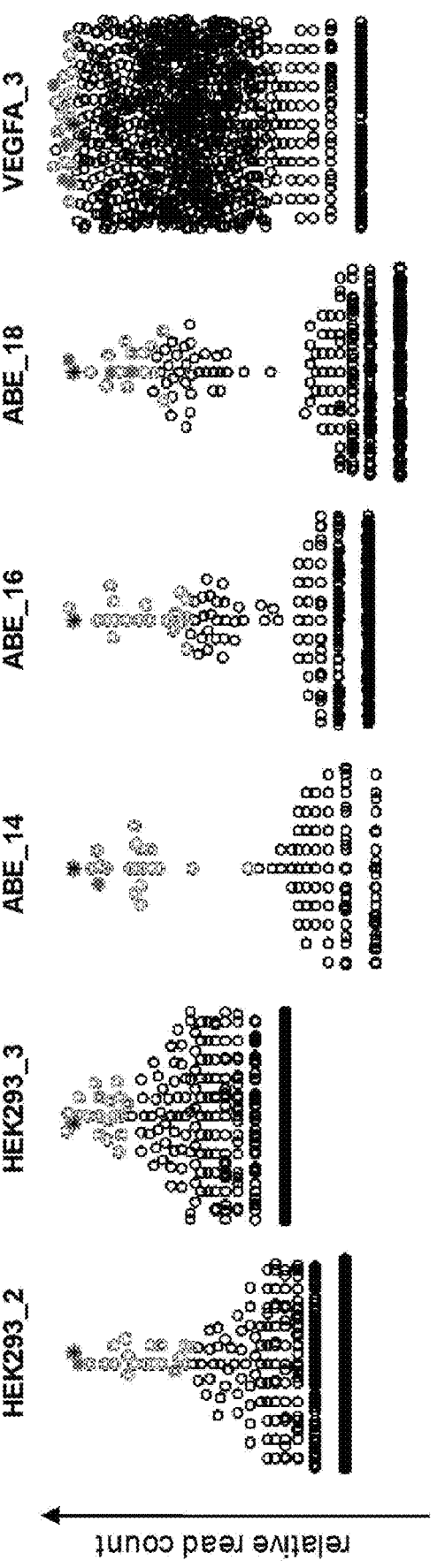
FIG. 23. Enrichment of ABE7.10 off-target sites by ONE-seq. Normalized aggregate read counts (where 1.0 corresponds to the on-target site) are shown for eight ONE-seq selections on genomic DNA-inspired libraries. Black stars represent on-target library members. Filled circles denote validated off-target sites. Open dark circles denote off-target candidates that were sequenced in the validation study.

We have additionally performed the above selection on genomic DNA libraries designed to identify off-target sequences of six guide RNAs (FIG. 23). Application of the modified ONE-seq selection protocol to six ABE targets revealed enrichment of the intended, on-target site to the top 3 of the post-selection libraries for the five non-promiscuous guides tested (HEK4 is a known promiscuous guide RNA). Validation by amplicon sequencing of DNA from human HEK293T cells individually transfected with the appropriate ABE7.10:sgRNA pairs of top candidate sites (approximately 20 each from each selection) identified 12 total confirmed cellular off-target sites across six target sites. This set includes the three validated off-target sites identified for the two guide RNAs that were tested by both ONE-seq and EndoV-seq (Liang et al. Nature Communications. 10: 67 (2019)) or Digenome-seq (Kim et al. Nature Biotechnology.

Figure 24:
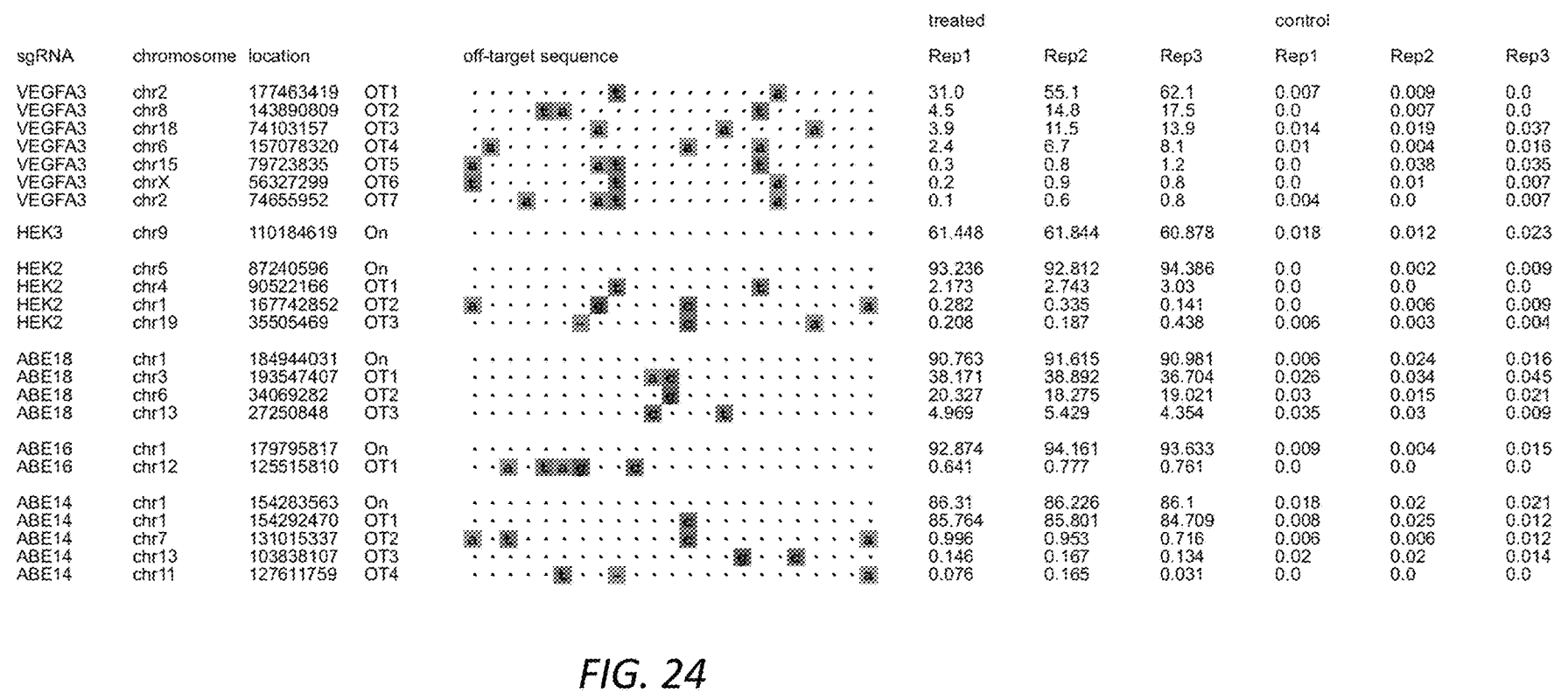

37: 430 (2019)) as well as nine newly validated off-target sites that were not identified as potential candidates by either of those methods. Nine of the 12 sites either had off-target modification rates below one percent or only showed evidence of a single nucleotide substitution, either of which could be caused by sequencing error despite stringent quality filtering of sequencing reads (all positions in paired reads must have quality score>Phred 30) and triplicate validation. To improve our confidence that these sites are bona fide off-target sites, we performed a second round of validation experiments with cells transfected with a plasmid expressing both ABEmax, a codon-optimized version of ABE7.10, and GFP and sorted the cells to enrich for the top decile of GFP, and therefore ABE, expression (FIG. 24). Genomic DNA extraction was performed immediately after sorting, without further expansion. In the sorted validation set, on target modification frequencies ranged from 61%-94%, compared to 31%-56% in the unsorted validation set. All 12 of the off-targets from the unsorted validation set were modified at higher frequencies in the sorted validation set, confirming that they are bona fide off-targets, and five additional off-target sites were identified at modification frequencies of less than one percent. One ABE_14 off-target site, containing a single mismatch relative to the on-target site, was modified in 85% of the DNA in the sorted validation (18% in the unsorted validation), suggesting that some ABE off-target sites can be modified at high frequencies.

Example 5: Base Editor Selections with ABE or BE3 Using an Enzyme that Creates a Double-Strand Break at Positions That Have Been Modified In this example, modified library members containing a deoxyinosine could be made to have blunt, double-stranded ends through the action of the TkoEndoMS protein (Ishino et al, Nucleic Acids Res. 44:2977 (2016)). TkoEndoMS can be used to create a doublestrand breaks at the dI: dT base pairs that result from dA→dI editing by ABE. DNA with a double strand break is then subject to the same downstream steps as in Example 1, with ligation of adapters to phosphorylated, blunt ended DNA if a base editing enzyme without nicking activity is used. If a base editing enzyme with nicking activity is used, end polishing with a blunt-end creating DNA polymerase (such as T4 or PHUSION® DNA polymerase (a high-fidelity thermostable polymerase with 5'→3' polymerase activity and 3'→5' exonuclease activity that generates blunt ends))), such as in Example 4, is used to allow for enrichment of both sides of a cut library member.

Figure 25:
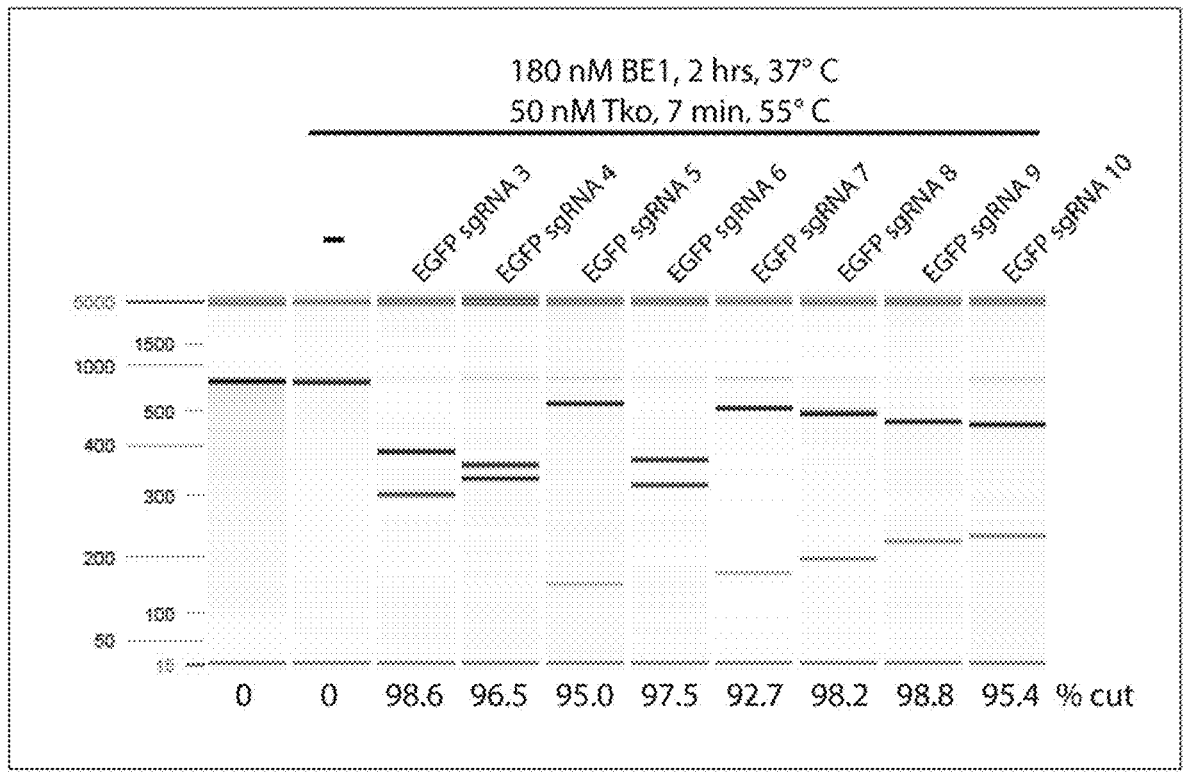
FIG. 25. Capillary electrophoresis data from an experiment demonstrating the specificity of TkoEndoMS' endonuclease activity for G:U DNA mismatches in vitro. An 800 base pair PCR amplicon was incubated with purified BE protein and a variable sgRNA for two hours to induce site-specific deamination. After purification, the deaminated PCR amplicon was incubated with purified TkoEndoMS protein for 7 minutes to induce double strand breaks at G:U mismatches. The DNA was then separated by size by capillary electrophoresis and imaged.

We have demonstrated that TkoEndoMS can also create double-strand breaks at dG:dU mismatched base pairs that result from dC→dU editing (in this example by BE1), demonstrating its additional applicability to BE1, BE3 and other enzymes that cause dC→dU changes after DNA binding (see U.S. Ser. No. 62/571,222 and FIG. 25). This strongly suggests that we can use TkoEndoMS on our synthesized DNA site libraries to identify off-target base edits caused by the various base editors that induce dC to dU edits, regardless of whether a Cas9-induced nick is also present.

Example 6: Enrichment of DNA Binding Sites by Pulldown

Figure 26:
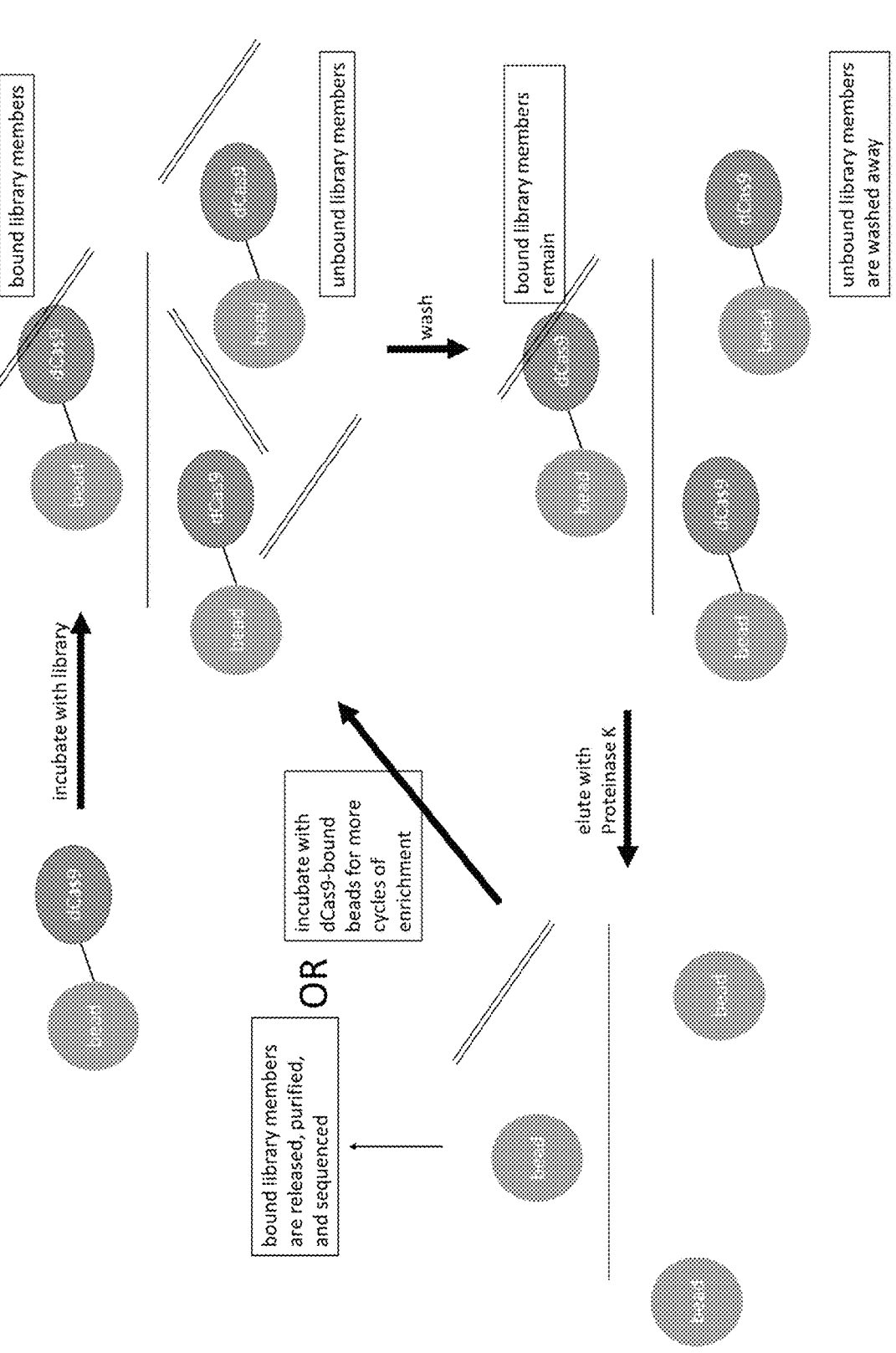
FIG. 26. Overview of enrichment for binding sites by pulldown. In this method, dCas9 coated beads are incubated with a library of potential off-target sites. Library members that are not bound are washed into supernatant, and bound library members are eluted by digesting bead-bound protein with Proteinase K. The resulting eluted library can either be amplified and subjected to additional rounds of pulldown or subjected to analysis by high throughput sequencing.
Figure 27:
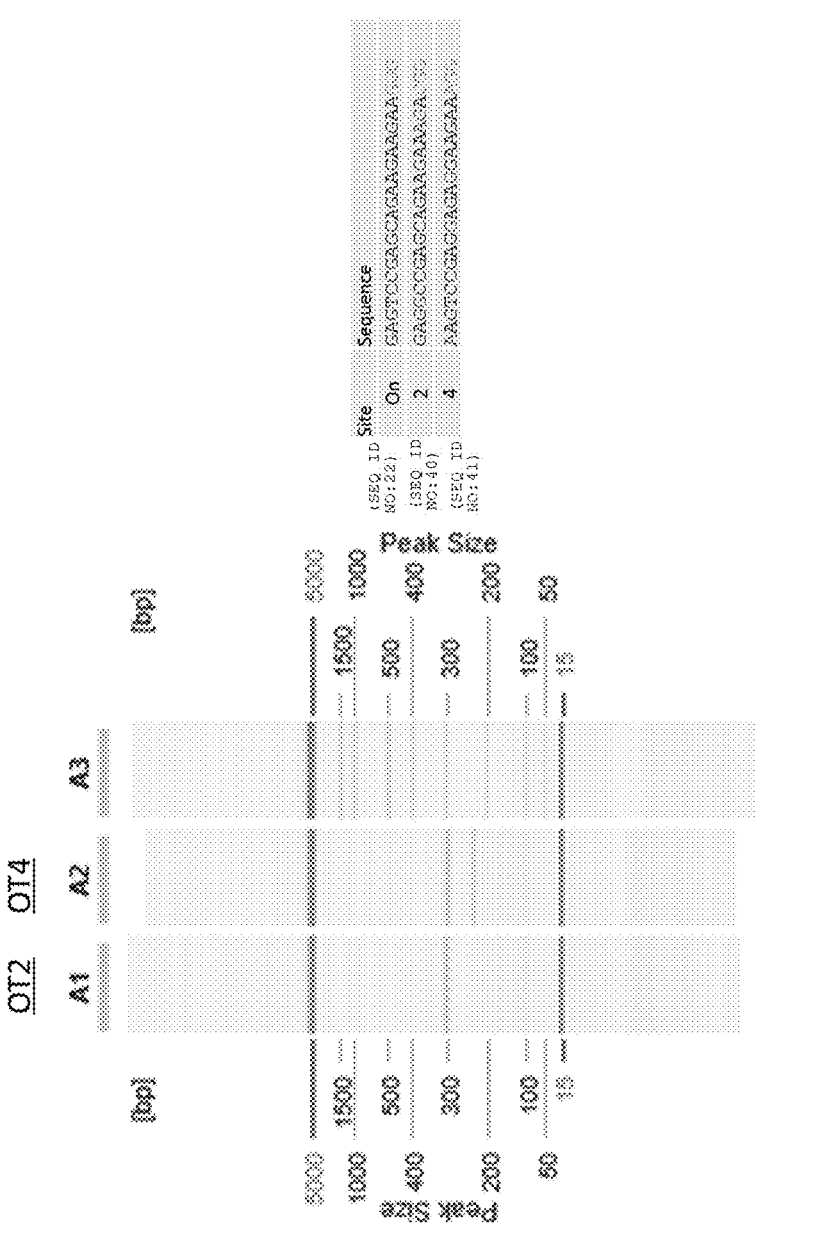
FIG. 27. Pulldown conditions can discriminate between on and off target sites. A mixture of three double stranded DNAs with differing lengths was subjected to binding site pulldown with dCas9: EMX1 sgRNA-coated beads. The on target site was present on a 280 base pair DNA, and one of two off target sites (OT2 or OT4) were present on a 220 base pair DNA. A third 200 bp ("random") DNA containing neither on nor off-target site was also in the mixture. Enriched DNA was run on a QIAxcel. Lane A3 denotes a size ladder. Lane A1 shows selective pulldown of the 280 base pair on target site, but no pull down of the OT2 site or the 200 bp DNA. Lane A2 shows that the OT4 site can still be bound in the method, demonstrating that the conditions used in the pulldown are able to enrich for off target sequences that are capable of being bound by a dCas9: EMX1 sgRNA. (SEQ ID NOs: 22, 40-41 appear in order)
Figure 28:
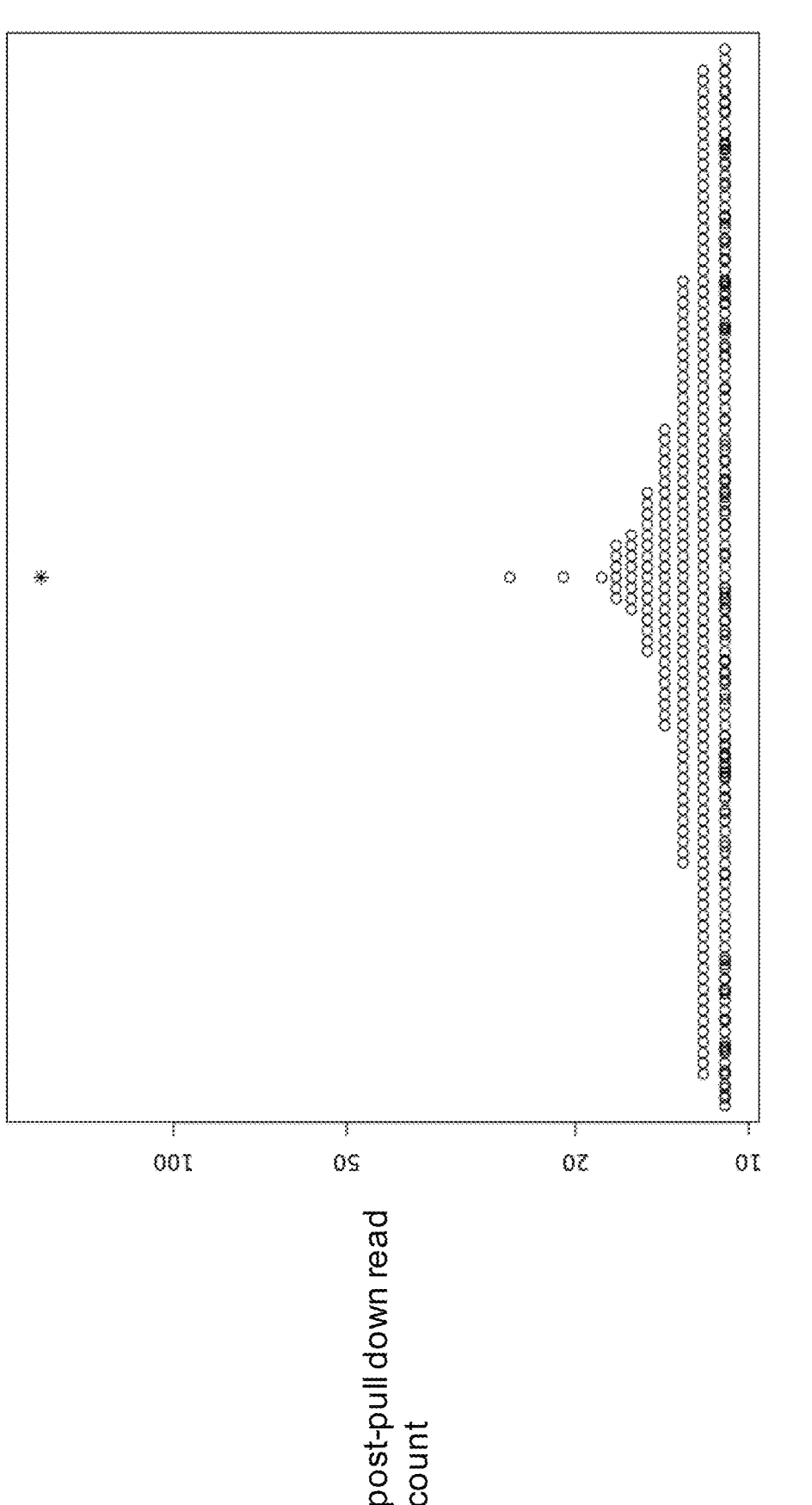
FIG. 28. Enrichment of genomic DNA-inspired library by pulldown. A pulldown conducted in the presence of 50 ug/ml heparin on the FANCF library leads to enrichment of the on-target site (black star) to the most abundant post-pull-down library member.

SELEX (selective evolutions of ligands by exponential enrichment) has been used to define the DNA-binding specificity of DNA-binding domains (originally by Oliphant et al., Mol Cell Biol. 9:2944, 1989). In the SELEX method, libraries of randomized DNA sequences are subjected to multiple rounds of pulldown and enrichment with an immobilized DNA binding domain of interest to identify the sequences in the initial pool that can bind to a DNA of interest. The SELEX method has been applied to the zinc finger and TALE moieties of ZFNs (Perez et al., Nat Biotech. 26:808 (2008)) and TALENs (Miller et al. Nat Biotech. 29:143 (2011)), however, there are no reports of SELEX studies on Cas9 proteins. We speculated that SELEX studies on Cas9 proteins are difficult due to the need to selectively enrich a 22 base pair target site from a large library, which would have to contain >1013 unique molecules, or at minimum 1012 molecules, corresponding to a 20 base pair target site, if an NGG PAM is fixed. In this example, we took advantage of pre-enriching our pre-selection libraries for sites that are most likely to be bound by a given Cas9: sgRNA complex (or other DNA-binding domain with predictable binding motifs). We assessed Cas9 DNA binding preferences and specificity by performing sequential rounds of DNA pull down experiments on the pre-enriched libraries (FIG. 26). This was achieved by tethering inactivated Cas9 (dCas9) to magnetic beads. To chemically bind dCas9 to magnetic beads we employed Cas9 protein harboring a so called SNAP-tag. Proteins with a SNAP-tag can be covalently bound to a benzylguanine-carrying substrate molecule, such as a magnetic bead. We envision incubating either type of oligonucleotide library with bead-bound SNAP-tagged dCas9 and enriching for DNA substrates with a high binding affinity to Cas9 by magnetic bead capture of bound sequences and washing away unbound sequences. This process could be repeated in multiple cycles by amplifying eluted library members and using the resulting enriched DNA library as a starting library for bead based selection. Using this method, with a single cycle, we have demonstrated conditions that could lead to selective pulldown with a dCas9: EMX1 sgRNA of the on target site compared to an off target site (FIG. 27). Furthermore, pulldown of a FANCF genomic DNA-inspired library, leads to maximal enrichment of the on-target site relative to other sites (FIG. 28). Detailed knowledge of Cas9 binding will be especially valuable to mechanistically study improved properties of genetically engineered Cas9 variants, such as high fidelity Cas9. Importantly, off-target patterns of Cas9 fusion proteins (or fusion patterns with other DNA binding domains) with limited interdependence of effector domain and DNA binding domain might be mainly defined by the DNA binding properties of the fusion protein. Performing DNA pulldown experiments on pre-enriched oligonucleotide libraries might therefore contribute to our understanding of fusion protein off-target distributions. Furthermore, by conducting DNA binding studies of Cas9 (or other DNA binding protein domains) on a library with limited complexity, high quality binding data with little background noise can be obtained that could be subsequently used to extrapolate and predict binding of more complex libraries, such as the genome of a cell.

Example 7: Homing Endonuclease Selections

Figure 29:
FIG. 29. Post-selection library composition for I-PpoI. A sequence logo is shown for sequences with at least 1% of the normalized read counts of the intended I-PpoI target site. Position in the site from 5' to 3' end is shown on the horizontal axis, and the height of the stack of letters denotes information content (in bits) for each position. The height of each individual nucleotide highlights the relative contribution of that nucleotide to the information content of that position. Positions 2, 13, and 14 are the most highly specified (highest information content). Position 15 is the least specified (lowest information content).

Homing endonucleases, such as I-PpoI, represent a group of naturally occurring nucleases that have longer base recognition motifs than the majority of restriction enzymes. Though homing endonucleases (also called meganucleases) do not have specificities that can be easily reprogrammed, if they target a genomic sequence of interest, they could be of research, commercial, or clinical use. Here, we show that we could adapt our in vitro selection to analyze the specificity profile of the I-PpoI homing endonuclease. We created an unbiased library of potential I-PpoI off-targets including all sites with up to 3 mismatches and single DNA/RNA bulges. The I-PpoI library contained 15533 members. I-PpoI selections enriched 501 of the 15533 library members (Table 3) while the intended, on-target site was ranked close to the top of the selection (28 out of 15533). Sequences with one mismatch or one insertion were the most enriched library members. Analysis of mismatch positions among top scoring I-PpoI off-target candidates revealed that certain positions within the recognition motif were more important for I-PpoI cleavage than others (FIG. 29). Especially positions 2, 13 and 14 seemed to be highly conserved and most important for I-PpoI mediated DNA cleavage. The adaptation of the in vitro selections to homing endonucleases demonstrates that the selections are broadly usable to analyze the off-target profiles of a variety of nucleases, including those that get cut to reveal sticky ends (like I-PpoI and Cas12a). I-PpoI leaves a 4 bp 3'-overhang, a DNA end configuration that is known to decrease the efficiency of off-target detection by existing methods such as GUIDE-seq or CIRCLE-seq. We therefore demonstrate that the in vitro selections can be used to analyze nucleases inducing staggered DNA breaks.

TABLE 3

Top 30 most-enriched sites in the post-selection library for I-PpoI on a unbiased DNA library.

| Align-ment | target | # | Found seqs_ cleaved | Found seqs_ cleaved_rmv |
|---|---|---|---|---|
| 1_0_1 | CTATCTTAAGGTAGTC | 97. | 1507 | 1459 |
| 1_0_1 | ACTCTCTTAAGGTAGC | 98. | 1329 | 1294 |
| 1_0_1 | CTATCTTAAGGTAGCC | 99. | 1264 | 1235 |
| 3_0_0 | CTACCTTAAGGTAGT | 100. | 1100 | 1071 |
| 3_0_0 | CTACCTTAAGGGAGC | 101. | 1017 | 989 |
| 2_0_0 | CTATCTTAAGGGAGC | 102. | 967 | 951 |
| 2_0_0 | CTCCCTTAAGGGAGC | 103. | 960 | 923 |
| 1_0_1 | CTATCTTAAGGTAGGC | 104. | 947 | 919 |
| 1_0_1 | CTCTCTTAAGGGAGCC | 105. | 920 | 896 |
| 1_0_1 | CTCTCTTAAGGTAGCT | 106. | 913 | 883 |
| 2_0_0 | CTCCCTTAAGGTAGT | 107. | 885 | 866 |
| 0_0_1 | CTCTCTTAAGGTAGTC | 108. | 865 | 842 |
| 1_0_1 | CTCTCTTAAGATAGCC | 109. | 858 | 836 |
| 2_0_0 | CTACCTTAAGGTAGC | 110. | 829 | 799 |
| 1_0_1 | CTCCCTTAAGGTAGTC | 111. | 781 | 765 |
| 1_0_1 | CTCTCATAAGGTAGTC | 112. | 744 | 724 |
| 1_0_1 | CTCTCATAAGGTAGCC | 113. | 744 | 722 |
| 1_0_1 | CTCTGTTAAGGTAGTC | 114. | 729 | 710 |
| 3_0_0 | CTCCCTTAAGAGAGC | 115. | 732 | 702 |
| 1_0_1 | CTCCCTTAAGGTAGCC | 116. | 713 | 694 |

TABLE 3-continued

Top 30 most-enriched sites in the post-selection
library for I-PpoI on a unbiased DNA library.

| Align-ment | target | # | Found seqs_ cleaved | Found seqs_ cleaved_rmv |
|---|---|---|---|---|
| 1_0_1 | CTCCCTTAAGGTAGAC | 117. | 709 | 689 |
| 1_0_0 | CTCTCTTAAGGTAGT | 118. | 679 | 670 |
| 2_0_0 | CTATCTTAAGGTAGT | 119. | 687 | 670 |
| 1_0_0 | CTCTCTTAAGGGAGC | 120. | 673 | 653 |
| 3_0_0 | CTATCTTAAGGGAGT | 121. | 651 | 639 |
| 1_0_1 | CTCTGTTAAGGTAGCC | 122. | 650 | 636 |
| 0_0_1 | CTCTCTTAAGGTAGGC | 123. | 650 | 633 |
| 0_0_0 | CTCTCTTAAGGTAGC | 124. | 643 | 628 |
| 1_0_0 | CTATCTTAAGGTAGC | 125. | 629 | 620 |
| 2_0_0 | CTCTCTTAAGAGAGC | 126. | 634 | 620 |

, SEQ ID NO:
Mostly closely matched off-target candidates were enriched to
the top of the selection. However, the selections demonstrated
that I-PpoI off-target candidates are exitent in abundance Methods: Library Generation Oligonucleotide library synthesis on high density chip arrays were purchased from Agilent.

Substrate Profiling Library:

1) An oligonucleotide backbone was developed that had 50% GC content and no potential canonical PAM sequences (NGG for *S. pyogenes* Cas9).

2) 13-14 base pair barcodes were generated that were at least two substitutions away from all other barcodes, were 40-60% GC, and did not contain any canonical PAM sequences for the minimally unbiased libraries:

3) potential off-target sites were generated for all possible combinations of substitutions, insertions, and deletions for an SpCas9 target site (these parameters can vary):

| substitutions | single base pair deletions | single base pair insertions |
|---|---|---|
| <=3 | 0 | 0 |
| <=1 | 1 | 0 |
| 0 | 2 | 0 |
| <=1 | 0 | 1 |

4) barcodes/potential off-target sites for all i off target sites (I~50,000) were combined into the backbone:

```
                              (SEQ ID NO: 127)
GACGTTCTCACAGCAATTCGTACAGTCGACGTCGATTCGTGCT (barcode_i) TTTGACATTCTGCAATTGCACACAGCGT (potential_ off_target_site_i) TGCAGACTGTAAGTATGTATGCTTCGCGCAGT

GCGACTTCGCAGCGCATCACTTCA (barcode_i) AGTAGCTGCGAGTCT

TACAGCATTGC
```

Genome-Inspired Library:

1) Potential off-target sites were generated with CasOffFinder according to the table below (these parameters can vary) and 20-113 bp (this parameter can vary) of genomic flanking sequence was added:

| substitutions | single base pair deletions | single base pair insertions |
|---|---|---|
| <=6 | 0 | 0 |
| <=4 | <=2 | 0 |
| <=3 | 0 | <=2 |
| 4 | 0 | 1 |

For an EMX1 site, here is an example of the number of sequences present given the above parameters.

| mismatches | insertion (DNA bulge) length | deletion (RNA bulge length) | # of sequences |
|---|---|---|---|
| 0 | 0 | 0 | 1 |
| 2 | 0 | 0 | 1 |
| 3 | 0 | 0 | 25 |
| 4 | 0 | 0 | 378 |
| 5 | 0 | 0 | 3903 |
| 6 | 0 | 0 | 30213 |
| 1 | 0 | 2 | 1 |
| 2 | 1 | 0 | 6 |
| 2 | 2 | 0 | 7 |
| 2 | 0 | 1 | 17 |
| 2 | 0 | 2 | 161 |
| 3 | 1 | 0 | 130 |
| 3 | 2 | 0 | 126 |
| 3 | 0 | 1 | 566 |
| 3 | 0 | 2 | 7579 |
| 4 | 1 | 0 | 2214 |
| 4 | 2 | 0 | 1942 |
| 4 | 0 | 1 | 8279 |
| | | Total | 55549 |

2) barcodes/potential off-target sites for all i off target sites (i~50,000) were combined into the backbone as for the minimally unbiased library with maximal genomic flanking context:

```
                              (SEQ ID NO: 128)
GACGTTCTCACAGCAATTCGT (barcode_i) (flanking genomic context_i) (potential_off_target_site_i)

(flanking_genomic_context_i) (barcode_i) TGCGAGTCTTACAG

CATTGC
```

Constant backbone sequence can be increased as the flanking genomic context is varied. For example, with 10 bp genomic flanking sequence on both sides:

```
                              (SEQ ID NO: 129)
GACGTTCTCACAGCAATTCGTACAGTCGACGTCGATTCGTGCT (barcode_i) TTTGACATTCTGCAATGT (flanking_genomic_context_i)

(potential_off_target_site_i)

(flanking_genomic_context_i) (AAGTATGTATGCTTCGCGCAGTG

CGACTTCGCAGCGCATCACTTCA (barcode_i) AGTAGCTGCGAGTCTTAC

AGCATTGC
```

Other Library Generation Strategies:

incorporate population based SNPs into genomic sequences generate libraries based on only coding DNA sequences generate libraries of sites that are oncogene hotspots or tumor suppressor genes

The following are examples of methods using off-target libraries constructed using the above principles.

Method for In Vitro Selection of Cleaved Library Members

1. Library Amplification

We amplify the oligonucleotide libraries using primers that bind to the constant flanking regions that are found in all library members. These primers contain 5'prime overhangs that introduce additional length and a unique molecular identifier. The libraries are amplified using the following protocol using 2 μl of the library at 5 nM concentration.

| | |
|---|---|
| SV (2l of 5 nM input library) | 2 |
| Thermopol buffer | 5 |
| Taq Polym. | 0.25 |
| dNTP 10 mM | 1 |
| KP_extension_new_fw* | 1 |
| KP_extension_new_rev* | 1 |
| H2O | 39.75 |
| RV | 50 |
| PCR program | |
| | |
| cycles | 12 |
| ID 95 | 30 |
| D 95 | 20 |
| A 50 | 15 |
| E 68 | 1 |
| FE 68 | 30 min |

SV—Samples Volume
RV—Reaction Volume
*KP_extension_new_fw, Primer Sequence: GCTGACTAGACACTGCTAT-CACACTCTCTCANNNNNNNNNAGACGTTCTCACAGCAATTCG (SEQ ID NO: 130)
*KP_extension_new_rev, Primer Sequence: GCGTAATCACT-GATGCTTCGTAAATGAGACANNNNNNNNTGCAATGCTGTAAGACTCGCA (SEQ ID NO: 131)

2. DNA Purification:

DNA purification with AMPure magnetic beads at a sample:bead ratio of 0.9× according to manufacturer's protocol.

3. Enzymatic Incubation:

Incubation of 300 ng of the chip-synthesized library with protein of interest at varying enzyme concentrations and incubation times. In most cases (Cas9, Cas9HF, BE3, ABE) it is sufficient to perform an 1-2 h incubation of the enzyme in activity buffer on 300 ng of oligonucleotide library at a molar ratio of 10:10:1 for protein, sgRNA and DNA substrate, respectively. Depending on the specific protein function, these parameters may need to be optimized.

4. Optional DNA Nicking:

Depending on the analyzed protein, enzymatic incubation may not result in the creation of a DNA double strand break (DSB). In the case of BE3 and ABE both enzymes merely nick on strand of DNA while base editing the other. By employing USER® enzyme (a mixture of Uracil DNA glycosylates (UDG) and the DNA glycosylate-lyase Endonuclease VIII) or Endonuclease V for BE3 and ABE, repectively, it is possible to convert this DNA nick into a staggered DSB (see FIGS. 8 and 9). To achieve this, bead-purified DNA is incubated with USER® enzyme (a mixture of Uracil DNA glycosylates (UDG) and the DNA glycosylate-lyase Endonuclease VIII) or Endonuclease V for one hour at 37° C. in their respective activity buffer.

5. DNA Purification:

DNA purification with AMPure magnetic beads at a sample:bead ratio of 1.5× according to manufacturer's protocol.

6. Optional DNA Blunting:

If an additional nicking step was required, the staggered DSB will be blunted by incubation with PHUSION® DNA polymerase (a high-fidelity thermostable polymerase with 5'→3' polymerase activity and 3'→5' exonuclease activity that generates blunt ends) for 20 min at 72° C. and then cooled to 4° C.

7. DNA Purification:

DNA purification with AMPure magnetic beads at a sample:bead ratio of 1.5× according to manufacturer's protocol.

8. Adapter Ligation:

Next, half functional Y-shape adapters are ligated to the blunted DNA from step 7. To achieve this, we supply adapter in 10-fold molar excess over library fragments and ligate using the NEB quick ligation kit, incubating the reaction at 25° C. for 10 min.

9. Gel Purification:

Next, we perform a gel purification of the ligation reaction by employing a 2.5% Agarose gel. The electrophoresis is performed at 120 Volt for 1 hour. After 1 hour the sample containing lanes are excised at around 180 bp fragment size and DNA is extracted using the Qiagen gel extraction kit according to manufacturer's protocol.

10. PCR-Amplification:

The eluate from step 9 is subsequently used as input for two PCR reactions that amplify the Protospacer-adjacent sequence and the PAM-adjacent sequence of library members cut by step 3 and optional step 4. The primers used in this PCR contain 5'overhangs that can be subsequently used to append Illumina sequencing barcodes. Optionally, QPCR can be performed to determine the minimum number of PCR cycles required. The PCRs are performed using the following parameters:

| | |
|---|---|
| Sample Volume | 6 |
| Phusion High Fidelity Buffer 5X | 10 |
| Phusion Polymerase | 0.5 |
| dNTP 10 mM | 1 |
| PrimerA | 2.5 |
| PrimerB | 2.5 |
| H2O | 27.5 |
| PCR program | |
| | |
| cycles | 25-35 |
| ID 98 | 30 |
| D 98 | 10 |
| A 65 | 20 |
| E 72 | 5 |
| FE 72 | 5 min |

11. DNA Purification:

DNA purification with AMPure magnetic beads at a sample:bead ratio of 1.5× according to manufacturer's protocol.

12. Quality Control Using Capillary Electrophoresis:

Quality control is performed by examining the PCR products via capillary electrophoresis.

13. PCR-Based NGS Library Preparation:

Sequencing adapters are appended to the PCR products from step 12 by performing a PCR with primers containing Illumina sequencing adapters. The PCRs are performed using the following parameters:

| | |
|---|---|
| Sample Volume | 50 ng total |
| Phusion High Fidelity Buffer 5X | 10 |
| Phusion Polymerase | 0.5 |
| dNTP 10 mM | 1 |

-continued

| | |
|---|---|
| IndexPrimerA | 2.5 |
| IndexPrimerB | 2.5 |
| H2O | Ad 50 |
| PCR program | |
| | |
| cycles | 10 |
| ID 98 | 30 |
| D 98 | 10 |
| A 65 | 30 |
| E 72 | 35 |
| FE 72 | 10 min |

14. DNA Purification:

DNA purification with AMPure magnetic beads at a sample:bead ratio of 1.5× according to manufacturer's protocol.

15. Next Generation Sequencing on Illumina Sequencers:

The DNA libraries from step 14 are quantified via digital droplet PCR and sequenced on Illumina sequencer's according to the manufacturer's protocol.

Method for Enrichment of DNA Binding Sites by Pulldown

1) Resuspend Snap Capture Beads (NEB)
2) Pipette 80 uL of the beads to a new 1.5 mL Eppendorf tube
3) Place tube in a magnetic particle separator and discard the supernatant
4) Add 1 mL of Immobilization Buffer (20 mM HEPES, 150 mM NaCl, 0.5% Tween20, 1 mM DTT, pH 6.5) and vortex gently
5) Place tube in a magnetic particle separator and discard the supernatant
6) Prepare the protein: Add Engen Spy dCas9 (SNAP-tag) (NEB) (4.5 uL of 20 uM per pull down reaction) to 500 uL of Immobilization Buffer
7) Add the diluted protein to the beads and mix well via pipetting
8) Incubate for 1 hour shaking at room temperature
9) Place tube in a magnetic particle separator and discard the supernatant
10) Wash the beads. Add 1 mL of Immobilization Buffer, pipette mix well, and then place the tube in a magnetic particle separator and discard the supernatant 11) Repeat step 10 twice more for a total of 3 washes. Perform the last wash with Immobilization Buffer with 10 ug/mL Heparin
12) Resuspend the beads in 45 uL of immobilization buffer per pull down
13) Mix the following:

| Component | Amount for 1 Pull Down Reaction |
|---|---|
| Water | Add enough to make the final volume 60 uL after adding everything including 0.9 pmol of Library |
| 10X Immobilization Buffer + 100 ug/mL Heparin | 6 uL |
| gRNA | 3500 ng |
| Engen Spy dCas9 (SNAP-tag) + Magnet Beads | 45 uL |

14) Incubate for 25 deg C. for 10 min
15) Add 0.9 pmol of library
16) Incubate at 37 deg C. for 30 min
17) Place the tube on a magnetic bead separator and discard the supernatant
18) Wash the beads 5 times with 200 uL of Immobilization Buffer with 10 ug/mL Heparin
19) Add 50 uL of water and 2 uL of Proteinase K and incubate at room temperature for 10 min while shaking
20) Clean up the pulled down product with DNA purification beads (for example, Ampure) and elute in 10 uL of 0.1× Buffer EB (QIAgen)

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An in vitro method of identifying double stranded DNA sequences that are cleaved by a nuclease, the method comprising:
   (i) providing a library of defined linear dsDNA oligonucleotides of known sequences, each library member having a known sequence comprising, in order:
   a first sequence common to each of the oligonucleotides in the library;
   a first barcode sequence unique to the library member;
   a potential DNA substrate sequence for the nuclease;
   a second copy of the barcode sequence; and
   a second sequence common to each of the oligonucleotides in the library;
   (ii) incubating the library in the presence of a site-specific nuclease under conditions sufficient for cleavage of one or more of the linear dsDNA oligonucleotides to occur;
   (iii) ligating DNA adapters comprising primer sequences to the cleaved ends of the dsDNA oligonucleotides;
   (iv) amplifying at least one of the cleaved dsDNA oligonucleotides using a primer specific to a primer sequence of the DNA adapter and a primer specific to at least one of the common sequences to generate amplified fragments; and
   (v) determining the barcode sequence(s) of the amplified fragments, thereby identifying double stranded DNA sequences that are cleaved by a nuclease.

2. The method of claim 1, wherein the linear dsDNA oligonucleotides comprise:
   (i) a set of all potential off-target sequences in a reference genome bearing mismatches relative to an identified on-target site;
   (ii) a comprehensive set of potential off-target sites bearing mismatches;
   (iii) a library of potential off-target sequences present in a set of variant genomes from defined populations; or
   (iv) another relevant defined set of potential off-target sites.

3. The method of claim 1, wherein:
   the library members are first synthesized as individual single-stranded DNA sequences; and the single-stranded DNA sequences are converted into double-stranded DNA molecules by priming against the first and/or second common sequence.

4. The method of claim 1, wherein the library members comprise 1,000 to $10^{11}$ different sequences.

5. The method of claim 1, wherein the library members comprise sequences that are 50 to 500 bp long.

6. The method of claim 1, wherein the nuclease is a Cas9 nuclease.

* * * * *